United States Patent
Wille et al.

(10) Patent No.: US 12,098,173 B2
(45) Date of Patent: Sep. 24, 2024

(54) INNOCUOUS, STRUCTURED SCAFFOLDS FOR STRUCTURE-BASED AMYLOID DISEASE VACCINES AND ANTIGENS

(71) Applicant: The Governors of the University of Alberta, Edmonton (CA)

(72) Inventors: Holger Wille, Edmonton (CA); Jiarui Fang, Lethbridge (CA); José Miguel Flores-Fernández, Edmonton (CA); Vineet Rathod, Edmonton (CA); Xinli Tang, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 370 days.

(21) Appl. No.: 17/057,418

(22) PCT Filed: May 22, 2019

(86) PCT No.: PCT/CA2019/050691
§ 371 (c)(1),
(2) Date: Nov. 20, 2020

(87) PCT Pub. No.: WO2019/222840
PCT Pub. Date: Nov. 28, 2019

(65) Prior Publication Data
US 2022/0064233 A1 Mar. 3, 2022

Related U.S. Application Data

(60) Provisional application No. 62/674,916, filed on May 22, 2018.

(51) Int. Cl.
| | | |
|---|---|---|
| *C07K 14/47* | (2006.01) |
| *A61K 39/00* | (2006.01) |
| *A61K 39/385* | (2006.01) |
| *A61P 25/16* | (2006.01) |
| *A61P 25/28* | (2006.01) |
| *A61P 37/04* | (2006.01) |
| *C07K 14/195* | (2006.01) |
| *C07K 14/285* | (2006.01) |
| *C07K 14/37* | (2006.01) |
| *C07K 14/705* | (2006.01) |
| *C07K 16/12* | (2006.01) |
| *C07K 16/14* | (2006.01) |
| *C07K 16/18* | (2006.01) |
| *C07K 16/28* | (2006.01) |
| *C12N 9/88* | (2006.01) |

(52) U.S. Cl.
CPC .......... *C07K 14/47* (2013.01); *A61K 39/0007* (2013.01); *A61K 39/385* (2013.01); *A61P 25/16* (2018.01); *A61P 25/28* (2018.01); *A61P 37/04* (2018.01); *C07K 14/195* (2013.01); *C07K 14/285* (2013.01); *C07K 14/37* (2013.01); *C07K 14/70596* (2013.01); *C07K 16/1203* (2013.01); *C07K 16/1242* (2013.01); *C07K 16/14* (2013.01); *C07K 16/18* (2013.01); *C07K 16/2872* (2013.01); *C12N 9/88* (2013.01); *C12Y 402/02002* (2013.01); *A61K 2039/6031* (2013.01); *A61K 2039/6068* (2013.01); *C07K 2319/33* (2013.01)

(58) Field of Classification Search
None
See application file for complete search history.

(56) References Cited

FOREIGN PATENT DOCUMENTS

WO   WO-2008124646 A2 * 10/2008 ........... A61K 38/164

OTHER PUBLICATIONS

Edwards et al. J. Mol. Biol. (2003) 334, 103-118.*
Ferrara et al. mAbs, 7:1, 32-41, 2015.*

* cited by examiner

*Primary Examiner* — Oluwatosin A Ogunbiyi
(74) *Attorney, Agent, or Firm* — Clark & Elbing LLP

(57) ABSTRACT

The present disclosure relates generally to polypeptides, which may be used of the treatment of neurological diseases or disorders.

14 Claims, 43 Drawing Sheets
Specification includes a Sequence Listing.

HET-2s
((218-289)-linker-(227-289))

HET-2s sequence

MKIDAIVGRNSAKDIRTEERARVQLGNVVTAAALHGGIRISDQTTNSVETVVGKGESRVLIGNEYGGKGFWDN
GGGGGGGAAGGGGG
NSAKDIRTEERARVQLGNVVTAAALHGGIRISDQTTNSVETVVGKGESRVLIGNEYGGKGFWDN
HHHHHH

(SEQ ID NO: 1)

Deer PrP structure: residues for HET-2s_14R1 highlighted

MVKSHIGSWILVLFVAMWSDVGLCKKRPKPGGGWNTGGSRYPG
QGSPGGNRYPPQGGGGWGQPHGGGWGQPHGGGWGQPHGGGWGQ
PHGGGGWGQGGTHSQWNKPSKPKTNMKHVAGAAAAGAVVGG<u>L</u>
<u>GGYMLGSAMSRPLIHFGNDYEDRYYRENMYRYPNQVYYRPVD</u>
<u>QYNNQNTFVHDCVNITVKQHTVTTTTKGENFTETDIKMMERVV</u>
<u>EQMCITQYQRESQAYY</u>QRGASVILFSSPPVILLISFLIFLIVG (SEQ ID NO: 2)

FIG. 4

Deer PrP structure (93-233 – MD expanded) with 14R1 residues in black

HET-2s 14R1 vaccine candidate

MKIDAIVGRNSAKYIDtEDRAEVQLGNVVTAAALHGGIRISDQTTNSVEKvNgKHESRVLIGNEYGGKGFWDN
GGGGGGGAAGGGGG
NSAKYIDtEDRAEVQLGNVVTAAALHGGIRISDQTTNSVEKvNgKHESRVLIGNEYGGKGFWDN
HHHHHH

(SEQ ID NO: 3)

HET-s structure with
14R1 in the middle only
(PrP-based residues K_N_KH & D_ED in black)

HET-s structure with 14R1 changes in black
(PrP-based residues K_N_KH & D_ED)

FIG. 9

Primary structure of IgG 61D8: CDRs

Heavy Chain

CKASGYSFTSYWMHWVKQRPGQGLEWIGMIDPSDSETKLNQQFKDKATLTVD
TSSSTAYMQLTSPTSEDSVVYYCARGKMGGRFYFDYLGQGTTLTVSSAKTTPPSVYPLA
(SEQ ID NO: 4)

| Antibody | HCDR1 | HCDR2 | HCDR3 |
|---|---|---|---|
| 61D8 | YSFTSYWMH | MIDPSDSETKLNQQFKD | GKMGGRFYFDY |

(SEQ ID NO: 5)    (SEQ ID NO: 6)    (SEQ ID NO: 35)

Light Chain

ITCKASQDVGTAVVWYQQKPGQSPKLLIYWASTRHTGVPDRFTGSGFGTDFTL
TISNVQSEDLADYFCQQFSSYPYTFGGGTKLEIKRADAAPTVS (SEQ ID NO: 7)

| Antibody | LCDR1 | LCDR2 | LCDR3 |
|---|---|---|---|
| 61D8 | KASQDVGTAVV | WASTRHT | QQFSSYPYT |

(SEQ ID NO: 8)    (SEQ ID NO: 9)    (SEQ ID NO: 10)

FIG. 15

14R1 model with
the 61D8 epitope in black

PrP^Sc model (Spagnolli et al., 2018) with the 61D8 epitope in black

PrP$^{Sc}$ tetramer model (Spagnolli et al., 2018) with the 61D8 epitope in black

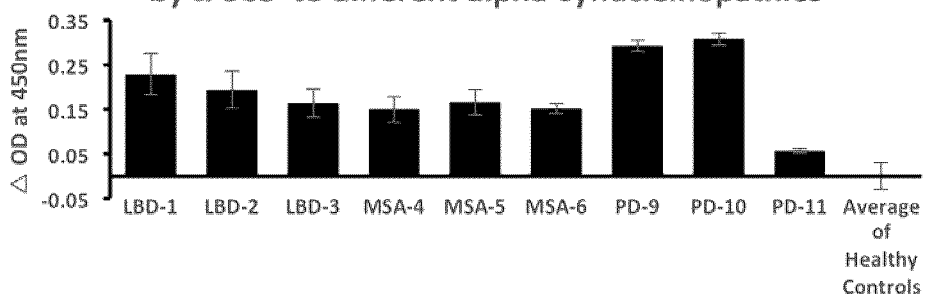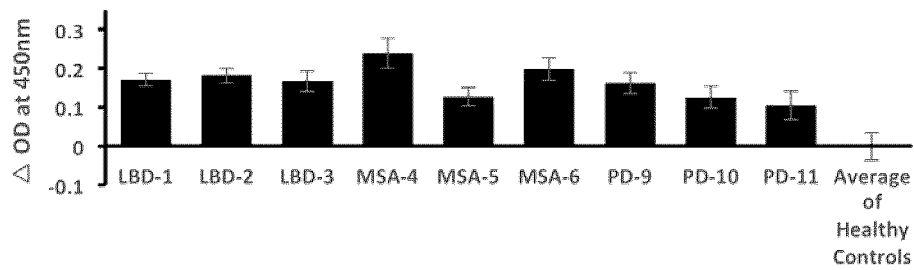
FIG. 28

Vaccine scaffold protein: HET-2s

MKIDAIVGRNSAKDIRTEERARVQLGNVVTAAALHGGIRISDQTTNSVETVVGKGESRVLIGN
EYGGKGFWDNGGGGGGGAAGGGGGNSAKDIRTEERARVQLGNVVTAAALHGGIRISDQT
TNSVETVVGKGESRVLIGNEYGGKGFWDNHHHHHH (SEQ ID NO: 1)

FIG. 32

Vaccine scaffold protein: HET-s

MKIDAIVGRNSAKDIRTEERARVQLGNVVTAAALHGGIRISDQTTNSVETVVGKGESRVLIGN
EYGGKGFWDNHHHHHH (SEQ ID NO: 11)

FIG. 33

Vaccine candidate: 14R1 (prion disease)

<u>Deer PrP sequence:</u> residues for HET-2s_14R1 in taller, bold font

MVKSHIGSWILVLFVAMWSDVGLCKKRPKPGGGWNTGGSRYPGQGSPGGNRYPPQGGG
GWGQPHGGGWGQPHGGGWGQPHGGGWGQPHGGGGWGQGGTHSQWNKPSKPKTN
MKHVAGAAAAGAVVGG<u>LGGYMLGSAMSRPLIHFGNDYEDRYYRENMYRYPNQVYYR</u>
<u>PVDQYNNQNTFVHDCVNITVKQHTVTTTTKGENFTETDIKMMERVVEQMCITQYQRESQAY</u>
<u>YQRGASVILFSSPPVILLISFLIFLIVG</u> (SEQ ID NO: 2)

<u>Adapted HET-2s sequence for 14R1:</u> residues from deer PrP in taller, bold font MKIDAIVGRNSAKYIDTEDRAEVQLGNVVTAAALHGGIRISDQTTNSVEKVNGKHESR
VLIGNEYGGKGFWDNGGGGGGGAAGGGGGNSAKYIDTEDRAEVQLGNVVTAAALHGGI
RISDQTTNSVEKVNGKHESRVLIGNEYGGKGFWDNHHHHHH (SEQ ID NO: 3)

FIG. 34

Vaccine candidate: AβC3 (Alzheimer's disease)

<u>Aβ(1-42) sequence:</u> residues for HET-s_ AßC3 in taller, bold font

DAEFRHDSGYEVHHQKLVFFAEDvGSNKGAIIGLMVGGVVIA (SEQ ID NO: 12)

<u>Adapted HET-s sequence for AβC3:</u> residues from Aβ(1-42) in taller, bold font MKIDAIVGRNSAVFIETDGSAKVQLGNVVTAAALHGGIRISDQTTNSVVFVEGDGSSKVLIGNEYGGKGFWDNHHHHHH (SEQ ID NO: 13)

FIG. 35

Vaccine candidate: AβC4 (Alzheimer's disease)

<u>Aβ(1-42) sequence:</u> residues for HET-s_ AßC4 in taller, bold font

DAEFRHDSGYEVHHQKLVFFAEDVGSNKGAIIGLMVGGVVIA (SEQ ID NO: 12)

<u>Adapted HET-s sequence for AβC4:</u> residues from Aβ(1-42) in taller, bold font MKIDAIVGRNRADDIYTVEHAKVQLGNVVTAAALHGGIRISDQTTNRVDTVYGVGHSKVLIGNEYGGKGFWDNHHHHHH **(SEQ ID NO

Vaccine candidate: TauC3 (Alzheimer's disease & tauopathies)

<u>partial Tau sequence:</u> residues for HET-s_ TauC3 in taller, bold font

VQIVYKPVDLSKVTSKCGSLGNIHHKPGGGQVEVKSEKLDFKDRVQSKIGSLDNITHV PGGGNKKIETHKLTF (SEQ ID NO: 15)

<u>Adapted HET-s sequence for TauC3:</u> residues from tau in taller, bold font

MKIDAIVGRNKAEKIDTKDRAQVKLGNVVTAAALHGGIRISDQTTNKVEKVDGKD RSQVKIGNEYGGKGFWDNHHHHHH (SEQ ID NO: 16)

FIG. 37

Vaccine candidate: TauC4 (Alzheimer's disease & tauopathies)

<u>partial Tau sequence:</u> residues for HET-s_ TauC4 in taller, bold font

VQIVYKPVDLSKVTSKCGSLGNIHHKPGGGQVEVKSEKLDFKDRVQSKIGSLDNITHVP GGGNKKIETHKLTF (SEQ ID NO: 15)

<u>Adapted HET-s sequence for TauC4:</u> residues from tau in taller, bold font

MKIDAIVGRNKAEKIDTKEDARVQLGNVVTAAALHGGIRISDQTTNKVEKVDGKDS RVQIGNEYGGKGFWDNHHHHHH (SEQ ID NO: 17)

FIG. 38

Vaccine candidate: α-SC3 (Parkinson's disease and synucleinopathies)

<u>Alpha-synuclein sequence:</u> residues for HET-s_ α-SC3 in taller, bold font

MDVFMKGLSKAKEGVVAAAEKTKQGVAEAAGKTKEGVLYVGSKTKEGVVHGVATVAEKTK EQVTNVGGAVVTGVTAVAQKTVEGAGSIAAATGFVKKDQLGKNEEGAPQEGILEDMPV DPDNEAYEMPSEEGYQDYEPEA  (SEQ ID NO: 18)

<u>Adapted HET-s sequence for α-SC3:</u> residues from alpha-synuclein in taller, bold font MKIDAIVGRNSAQVINTGGRARVQLGNVVTAAALHGVATIAEQTTNSVQVVNGGGE SRVLIGNEYGGKGFWDNHHHHHH  (SEQ ID NO: 19)

FIG. 39

Vaccine candidate: α-SC6 (Parkinson's disease and synucleinopathies)

<u>Alpha-synuclein sequence:</u> residues for HET-s_α-SC6 in taller, bold font

MDVFMKGLSKAKEGVVAAAEKTKQGVAEAAGKTKEGVLYVGSKTKEGVVHGVATVAEKTK EQVTNVGGAVVTGVTAVAQKTVEGAGSIAAATGFVKKDQLGKNEEGAPQEGILEDMPVD PDNEAYEMPSEEGYQDYEPEA  (SEQ ID NO: 18)

<u>Adapted HET-s sequence for α-SC6:</u> residues from alpha-synuclein in taller, bold font MKIDAIVGRNSAKDIKTVEGARVQLGNVVTAAALHGGIRISDQTTNSVETVKGVEGSRV LIGNEYGGKGFWDNHHHHHH  (SEQ ID NO: 20)

FIG. 40

Vaccine candidate: α-SC8 (Parkinson's disease and synucleinopathies)

Alpha-synuclein sequence: residues for HET-s_α-SC8 in taller, bold font

MDVFMKGLSKAKEGVVAAAEKTKQGVAEAAGKTKEGVLYVGSKTKEGVVHGVATVAEKTKEQVTNVGGAVVTGVTAVAQKTVEGAGSIAAATGFVKKDQLGKNEEGAPQEGILEDMPVDPDNEAYEMPSEEGYQDYEPEA (SEQ ID NO: 18)

Adapted HET-s sequence for α-SC8: residues from alpha-synuclein in taller, bold font MKIDAIVGKNQATDIRTEERARVQLGNVVTAAALHGGIRISDQTKNQVTVVGKGESRVLIGNEYGGKGFWDNHHHHHH (SEQ ID NO: 21)

FIG. 41

Vaccine candidate: α-SC9 (Parkinson's disease and synucleinopathies)

Alpha-synuclein sequence: residues for HET-s_α-SC9 in taller, bold font

MDVFMKGLSKAKEGVVAAAEKTKQGVAEAAGKTKEGVLYVGSKTKEGVVHGVATVAEKTKEQVTNVGGAVVTGVTAVAQKTVEGAGSIAAATGFVKKDQLGKNEEGAPQEGILEDMPVDPDNEAYEMPSEEGYQDYEPEA (SEQ ID NO: 18)

Adapted HET-s sequence for α-SC9: residues from alpha-synuclein in taller, bold font MKIDAIVGRNKAVEIATEERARVQLGNVVTAAALHGGIRISDQTTNKVVEVAGKGESRVLIGNEYGGKGFWDNHHHHHH (SEQ ID NO: 22)

FIG. 42

Vaccine scaffold protein: 3P4G-Vac

Antifreeze protein sequence: residues that were used to create a four-rung, right-handed β-solenoid vaccine scaffold are shown in taller, bold font MNVSQSNSFGFWDGTSTQAEITHSFDHYIGSAFDASNNNVAVTGNVSATLNVLAGD DKVSIDGNVEDVLVAANVAVLDMGTGNDQLYVAGDVLGKIDAGT GNDEIYIKGDVSAAVDAGTGNDEVYIGGNLSGDLDAGTDNDNIQIGG DVNAALNAGTGNDNLIIGHDVSGIVNMGTDNDTVEVGRTINASGKVLLDTGDDSLLVSGDLF GEVDGGTGNDTIIIAGKVSGNIQGGTGNDIVRVQSQVWAEANISLGTGDDVLIVEHELHGTV AGNEGDDSIYLKFYTKEQYNNNSDLRNRVANFEHIRVSDGVVKGSPADFADY (SEQ ID NO: 23)

3P4G-Vac: a four-rung, right-handed β-solenoid vaccine scaffold:

MAHHHHHHVGT*ENLYFQG*DLKVLAGDDKVSIDGNVSGALDMGTGNDQLYVA GDVLGKIDAGTGNDEIYIKGDVSAAVDAGTGNDEVYIGGNLSK (SEQ ID NO: 24)

FIG. 43

Vaccine candidate: 3P4G-C7 (prion disease)

Deer PrP sequence: residues for 3P4G-C7 in taller, bold font

MVKSHIGSWILVLFVAMWSDVGLCKKRPKPGGGWNTGGSRYPGQGSPGGNRYPPQGGG
GWGQPHGGGWGQPHGGGWGQPHGGGWGQPHGGGGWGQGGTHSQWNKPSKPKTN
MKHVAGAAAAGAVVGGLGGYMLGSAMSRPLIHFGNDYEDRYYRENMYRYPNQVYYRP

VDQYNNQNTFVHDCVNITVKQHTVTTTTKGENFTETDIKMMERVVEQMCITQYQRESQA
YYQRGASVILFSSPPVILLISFLIFLIVG   (SEQ ID NO: 2)

Adapted 3P4G-Vac sequence for 3P4G-C7: residues from deer PrP in taller, bold font MAHHHHHHVGTENLYFQGDLKVLAGDDKVSIDGNVSGALDMGTGNDQLYVAGDVLGKIDA
GTGLDSIMIKGDVSAAVDAGTGQDNVQIGGNLSK   (SEQ ID NO: 25)

FIG. 44

Vaccine scaffold protein: PL3-Vac

Pectate lyase sequence from family 3 (PDB: 4Z05): protein used in full-length as a right-handed β-solenoid vaccine scaffold.

MAHHHHHHVGTNTGGVLVITDTIIVKSGQTYDGKGIKIIAQGMGDGSQSENQKPIFKLEKG
ANLKNVIIGAPGCDGIHCYGDNVVENVVWEDVGADALTVKSEGVVEVIGGSAKEAADKVF
QLNAPCTFKVKNFTATNIGKLVRQNGNTTFKVVIYLEDVTLNNVKSCVAKSDSPVSELWY
HNLNVNNCKTLFEFPSQSQIHQY   (SEQ ID NO: 26)

FIG. 45

Vaccine candidate: PL3C1 (prion disease)

Deer PrP sequence: residues for PL3C1 in taller, bold font

MVKSHIGSWILVLFVAMWSDVGLCKKRPKPGGGWNTGGSRYPGQGSPGGNRYPPQGGG

GWGQPHGGGWGQPHGGGWGQPHGGGWGQPHGGGGWGQGGTHSQWNKPSKPKTN

MKHVAGAAAAGAVVGGLGGYMLGSAMSRPLIHFGNDyEDRYYRENMYRYPNQVYYR

PVDQYNNQNTFVHDCVNITVKQHTVTTTTKGENFTETDIKMMERVVEQMCITQYQRESQAY

YQRGASVILFSSPPVILLISFLIFLIVG   (SEQ ID NO: 2)

Adapted PL3-Vac sequence for PL3C1: residues from deer PrP in taller, bold font

MAHHHHHHVGTNTGGVLVITDTIIVKSGQTYDGKGIKIIAQGMGDGSQSENQKPIFKLEKGA

NLKNVIIGAPGCDGIHCYGDNVVENVVWEDVGADALTVKSEGVVEVIKGNAKHAADKVF

QLNAPCTFKVKNFDAEDIGKLVRQNGNTTFKVVIYLEKVNL KHVKSCVAKSDSPVSEL

WYHNLDvEDCKTLFEFPSQSQIHQY   (SEQ ID NO: 27)

FIG. 46

Vaccine candidate: PL3C2 (prion disease)

Deer PrP sequence: residues for PL3C2 in taller, bold font

MVKSHIGSWILVLFVAMWSDVGLCKKRPKPGGGWNTGGSRYPGQGSPGGNRYPPQGGG GWGQPHGGGWGQPHGGGWGQPHGGGWGQPHGGGGWGQGGTHSQWNKPSKPKTN mKHVAGAAAAGAVVGGLGGYMLGSAMSRPLIHFGNDYEDRYYRENMYRYPNQVYYR PVDQYNNQNTFVHDCVNITVKQHTVTTTTKGENFTETDIKMMERVVEQMCITQYQRESQAY YQRGASVILFSSPPVILLISFLIFLIVG  (SEQ ID NO: 2)

Adapted PL3-Vac sequence for PL3C2: residues from deer PrP in taller, bold font MAHHHHHHVGTNTGGVLVITDTIIVKSGQTYDGKGIKIIAQGMGDGSQSENQKPIFKLEKGA NLKNVIIGAPGCDGIHCYGDNVVENVVWEDVGADALTVKSEGVVEVIGGDAEDAADKVF QLNAPCTFKVKKFNAKHIGKLVRQNGNTTFKVVIYLEDVDL EDVKSCVAKSDSPVSEL WYHKL NVKHCKTLFEFPSQSQIHQY  (SEQ ID NO: 28)

FIG. 47

Vaccine scaffold protein: 2ODL-Vac

<u>HMW1 secretion domain sequence from *Haemophilus influenzae* (PDB#: 2ODL):</u>
residues that were selected to create a for 4-rung, right-handed β-solenoid vaccine scaffold are shown in taller, bold font.

SGLQGMDVVHGTATMQVDGNKTIIRNSVDAIINWKQFNIDQNEMVQFLQENNNSAVFNRVT SNQISQLKGILDSNGQVFLINPNGITIGKDAIINTNGFTASTLDISNENIKARNFTFEQTKDKAL AEIVNHGLITVGKDGSVNLIGGKVKNEGVISVNGGSISLLAGQ KITISDIINPTITYSIAAPENEAVNLGDIFAKGGNINVRAATIRNQGKLSA DSVSKDGSGNIVLSAKEGEAEIGGVISAQNQQAKGGKLMITGDKVTLKTGAVIDLSG KEGGETYLGGDERGEGKNGIQLAKKTSLEKGSTINVSGKEKGGRAIVWGDIALIDGNINAQG SGDIAKTGGFVETSGHDLFIKDNAIVDAKEWLLD (SEQ ID NO: 29)

<u>Sequence of 2ODL-Vac: a four-rung, right-handed β-solenoid vaccine scaffold:</u>

MAHHHHHHVG*TENLYFQG*<u>K</u>EIVNHGLITVGDGSVNLIGGKVKNEGVISVNGGSI SLLAGEAVNLGDIFAKGGNINVRAATIRNQGKLSAG<u>K</u>GNIVLSAGE (SEQ ID NO: 30)

FIG. 48

Vaccine scaffold protein: 1HG8-Vac

<u>Endopolygalacturonase sequence from *fungus Fusarium moniliforme* (PDB#: 1HG8):</u>
residues used to create a for 4-rung, right-handed β-solenoid vaccine scaffold are shown in taller, bold font DPCSVTEYSGLATAVSSCKNIVLNGFQVPTGKQLDLSSLQNDSTVTFKGTTTFATTADNDF NPIVISGSNITITGASGHVIDGNGQAYWDGKGSNSNSNQKPDHFIVVQKTTGNSKITNLNIQN WPVHCFDITGSSQLTISGLILDNRAGDKPNAKSGSLPAAHNTDGFDISSSDHVTLD NNHVYNQDDCVAVTSGTNIVVSNMYCSGGHGLSIGSVGGKS DNVVDGVQFLSSQVVNSQNGCRIKSNSGATGTINNVTYQNI ALTNISTYGVDVQQDYLNGGPTGKPTNGVKISNIKFIKVTGTVASSAQDWFILCGDGSC SGFTFSGNAITGGGKTSSCNYPTNTCPS  (SEQ ID NO: 31)

Sequence of <u>1HG8-Vac: a four-rung, right-handed β-solenoid vaccine scaffold:</u>
MAHHHHHHVG*TENLYFQG*DGFDISSSDHVTLDNNHVYNQDDCVAVTSGTNIVV SNMYCSGGHGLSIGSVGGKSDNVVDGVQFLSSQVVNSQNGCRIKSNSGATGTINNVTYQN IALTNISR̲    (SEQ ID NO: 32)

FIG. 49

SEQUENCE LISTING

```
<160> NUMBER OF SEQ ID NOS: 35

<210> SEQ ID NO 1
<211> LENGTH: 157
<212> TYPE: PRT
<213> ORGANISM: Artificial Sequence
<220> FEATURE:
<223> OTHER INFORMATION: Synthetic Construct

<400> SEQUENCE: 1

Met Lys Ile Asp Ala Ile Val Gly Arg Asn Ser Ala Lys Asp Ile Arg
1               5                   10                  15

Thr Glu Glu Arg Ala Arg Val Gln Leu Asn Gly Val Val Thr Ala Ala
                20                  25                  30

Ala Leu His Gly Gly Ile Arg Ile Ser Asp Gln Thr Thr Asn Ser Val
            35                  40                  45

Glu Thr Val Val Gly Lys Gly Glu Ser Arg Val Leu Ile Gly Asn Glu
        50                  55                  60

Tyr Gly Gly Lys Gly Phe Trp Asp Asn Gly Gly Gly Gly Gly Gly Gly
65                  70                  75                  80

Ala Ala Gly Gly Gly Gly Gly Asn Ser Ala Lys Asp Ile Arg Thr Glu
                85                  90                  95
```

Glu Arg Ala Arg Val Gln Leu Gly Asn Val Val Thr Ala Ala Ala Leu
            100                 105                 110

His Gly Gly Ile Arg Ile Ser Asp Gln Thr Thr Asn Ser Val Glu Thr
        115                 120                 125

Val Val Gly Lys Gly Glu Ser Arg Val Leu Ile Gly Asn Glu Tyr Gly
130                 135                 140

Gly Lys Gly Phe Trp Asp Asn His His His His His
145                 150                 155

<210> SEQ ID NO 2
<211> LENGTH: 256
<212> TYPE: PRT
<213> ORGANISM: Artificial Sequence
<220> FEATURE:
<223> OTHER INFORMATION: Synthetic Construct

<400> SEQUENCE: 2

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 3
<211> LENGTH: 158
<212> TYPE: PRT
<213> ORGANISM: Artificial Sequence
<220> FEATURE:
<223> OTHER INFORMATION: Synthetic Construct

<400> SEQUENCE: 3

Met Lys Ile Asp Ala Ile Val Gly Arg Asn Ser Ala Lys Tyr Ile Asp
1               5                   10                  15

Thr Glu Asp Arg Ala Glu Val Gln Leu Gly Asn Val Val Thr Ala Ala
                20                  25                  30

Ala Leu His Gly Gly Ile Arg Ile Ser Asp Gln Thr Thr Asn Ser Val
            35                  40                  45

Glu Lys Val Asn Gly Lys His Glu Ser Arg Val Arg Leu Ile Gly Asn
        50                  55                  60

Glu Tyr Gly Gly Lys Gly Phe Trp Asp Asn Gly Gly Gly Gly Gly Gly
65                  70                  75                  80

Gly Ala Ala Gly Gly Gly Gly Asn Ser Ala Lys Tyr Ile Asp Thr
                85                  90                  95

Glu Asp Arg Ala Glu Val Gln Leu Gly Asn Val Val Thr Ala Ala Ala
                100                 105                 110

Leu His Gly Gly Ile Arg Ile Ser Asp Gln Thr Thr Asn Ser Val Glu
            115                 120                 125

Lys Val Asn Gly Lys His Glu Ser Arg Val Leu Ile Gly Asn Glu Tyr
        130                 135                 140

Gly Gly Lys Gly Phe Trp Asp Asn His His His His His
145                 150                 155

<210> SEQ ID NO 4
<211> LENGTH: 111
<212> TYPE: PRT
<213> ORGANISM: Artificial Sequence
<220> FEATURE:
<223> OTHER INFORMATION: Synthetic Construct

<400> SEQUENCE: 4

Cys Lys Ala Ser Gly Tyr Ser Phe Thr Ser Tyr Trp Met His Trp Val
1               5                   10                  15

Lys Gln Arg Pro Gly Gln Gly Leu Glu Trp Ile Gly Met Ile Asp Pro
                20                  25                  30

Ser Asp Ser Glu Thr Lys Leu Asn Gln Gln Phe Lys Asp Lys Ala Thr
            35                  40                  45

Leu Thr Val Asp Thr Ser Ser Thr Ala Tyr Met Gln Leu Thr Ser
        50                  55                  60

Pro Thr Ser Glu Asp Ser Val Val Tyr Tyr Cys Ala Arg Gly Lys Met
65                  70                  75                  80

Gly Gly Arg Phe Tyr Phe Asp Tyr Leu Gly Gln Gly Thr Thr Leu Thr
                85                  90                  95

Val Ser Ser Ala Lys Thr Thr Pro Pro Ser Val Tyr Pro Leu Ala
            100                 105                 110

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Tyr Ser Phe Thr Ser Tyr Trp Met His
1               5

<210> SEQ ID NO 6
<211> LENGTH: 17

```
<212> TYPE: PRT
<213> ORGANISM: Artificial Sequence
<220> FEATURE:
<223> OTHER INFORMATION: Synthetic Construct

<400> SEQUENCE: 6

Met Ile Asp Pro Ser Asp Ser Glu Thr Lys Leu Asn Gln Gln Phe Lys
1               5                   10                  15

Asp

<210> SEQ ID NO 7
<211> LENGTH: 96
<212> TYPE: PRT
<213> ORGANISM: Artificial Sequence
<220> FEATURE:
<223> OTHER INFORMATION: Synthetic Construct

<400> SEQUENCE: 7

Ile Thr Cys Lys Ala Ser Gln Asp Val Gly Thr Ala Val Val Trp Tyr
1               5                   10                  15

Gln Gln Lys Pro Gly Gln Ser Pro Lys Leu Leu Ile Tyr Trp Ala Ser
            20                  25                  30

Thr Arg His Thr Gly Val Pro Asp Arg Phe Thr Gly Ser Gly Phe Gly
        35                  40                  45

Thr Asp Phe Thr Leu Thr Ile Ser Asn Val Gln Ser Glu Asp Leu Ala
    50                  55                  60

Asp Tyr Phe Cys Gln Gln Phe Ser Ser Tyr Pro Tyr Thr Phe Gly Gly
65                  70                  75                  80

Gly Thr Lys Leu Glu Ile Lys Arg Ala Asp Ala Ala Pro Thr Val Ser
                85                  90                  95

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Lys Ala Ser Gln Asp Val Gly Thr Ala Val Val
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Trp Ala Ser Thr Arg His Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Gln Gln Phe Ser Ser Tyr Pro Tyr Thr
1               5
```

<210> SEQ ID NO 11
<211> LENGTH: 79
<212> TYPE: PRT
<213> ORGANISM: Artificial Sequence
<220> FEATURE:
<223> OTHER INFORMATION: Synthetic Construct

<400> SEQUENCE: 11

Met Lys Ile Asp Ala Ile Val Gly Arg Asn Ser Ala Lys Asp Ile Arg
1               5                   10                  15

Thr Glu Glu Arg Ala Arg Val Gln Leu Gly Asn Val Val Thr Ala Ala
            20                  25                  30

Ala Leu His Gly Gly Ile Arg Ile Ser Asp Gln Thr Thr Asn Ser Val
        35                  40                  45

Glu Thr Val Val Gly Lys Gly Glu Ser Arg Val Leu Ile Gly Asn Glu
    50                  55                  60

Tyr Gly Gly Lys Gly Phe Trp Asp Asn His His His His His
65                  70                  75

<210> SEQ ID NO 12
<211> LENGTH: 42
<212> TYPE: PRT
<213> ORGANISM: Artificial Sequence
<220> FEATURE:
<223> OTHER INFORMATION: Synthetic Construct

<400> SEQUENCE: 12

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 13
<211> LENGTH: 79
<212> TYPE: PRT
<213> ORGANISM: Artificial Sequence
<220> FEATURE:
<223> OTHER INFORMATION: Synthetic Construct

<400> SEQUENCE: 13

Met Lys Ile Asp Ala Ile Val Gly Arg Asn Ser Ala Val Phe Ile Glu
1               5                   10                  15

Thr Asp Gly Ser Ala Lys Val Gln Leu Gly Asn Val Val Thr Ala Ala
            20                  25                  30

Ala Leu His Gly Gly Ile Arg Ile Ser Asp Gln Thr Thr Asn Ser Val
        35                  40                  45

Val Phe Val Glu Gly Asp Gly Ser Ser Lys Val Leu Ile Gly Asn Glu
    50                  55                  60

Tyr Gly Gly Lys Gly Phe Trp Asp Asn His His His His His
65                  70                  75

<210> SEQ ID NO 14
<211> LENGTH: 79
<212> TYPE: PRT
<213> ORGANISM: Artificial Sequence
<220> FEATURE:
<223> OTHER INFORMATION: Synthetic Construct

<400> SEQUENCE: 14

-continued

Met Lys Ile Asp Ala Ile Val Gly Arg Asn Arg Ala Asp Asp Ile Tyr
1               5                   10                  15

Thr Val Glu His Ala Lys Val Gln Leu Gly Asn Val Val Thr Ala Ala
            20                  25                  30

Ala Leu His Gly Gly Ile Arg Ile Ser Asp Gln Thr Thr Asn Arg Val
        35                  40                  45

Asp Thr Val Tyr Gly Val Gly His Ser Lys Val Leu Ile Gly Asn Glu
    50                  55                  60

Tyr Gly Gly Lys Gly Phe Trp Asp Asn His His His His His
65                  70                  75

<210> SEQ ID NO 15
<211> LENGTH: 73
<212> TYPE: PRT
<213> ORGANISM: Artificial Sequence
<220> FEATURE:
<223> OTHER INFORMATION: Synthetic Construct

<400> SEQUENCE: 15

Val Gln Ile Val Tyr Lys Asp Leu Pro Val Ser Lys Val Thr Ser Lys
1               5                   10                  15

Cys Gly Ser Leu Gly Asn Ile His His Lys Pro Gly Gly Gly Gln Val
            20                  25                  30

Glu Val Lys Ser Glu Lys Leu Asp Phe Lys Asp Arg Val Gln Ser Lys
        35                  40                  45

Ile Gly Ser Leu Asp Asn Ile Thr His Val Pro Gly Gly Gly Asn Lys
    50                  55                  60

Lys Ile Glu Thr His Lys Leu Thr Phe
65                  70

<210> SEQ ID NO 16
<211> LENGTH: 79
<212> TYPE: PRT
<213> ORGANISM: Artificial Sequence
<220> FEATURE:
<223> OTHER INFORMATION: Synthetic Construct

<400> SEQUENCE: 16

Met Lys Ile Asp Ala Ile Val Gly Arg Asn Lys Ala Glu Lys Ile Asp
1               5                   10                  15

Thr Lys Asp Arg Ala Gln Val Lys Leu Gly Asn Val Val Thr Ala Ala
            20                  25                  30

Ala Leu His Gly Gly Ile Arg Ile Ser Asp Gln Thr Thr Asn Lys Val
        35                  40                  45

Glu Lys Val Asp Gly Lys Asp Arg Ser Gln Val Lys Ile Gly Asn Glu
    50                  55                  60

Tyr Gly Gly Lys Gly Phe Trp Asp Asn His His His His His
65                  70                  75

<210> SEQ ID NO 17
<211> LENGTH: 79
<212> TYPE: PRT
<213> ORGANISM: Artificial Sequence
<220> FEATURE:
<223> OTHER INFORMATION: Synthetic Construct

<400> SEQUENCE: 17

Met Lys Ile Asp Ala Ile Val Gly Arg Asn Lys Ala Glu Lys Ile Asp
1               5                   10                  15

Thr Lys Glu Asp Ala Arg Val Gln Leu Gly Asn Val Val Thr Ala Ala

```
                    20                  25                  30

Ala Leu His Gly Gly Ile Arg Ile Ser Asp Gln Thr Thr Asn Lys Val
            35                  40                  45

Glu Lys Val Asp Gly Lys Gly Asp Ser Arg Val Gln Ile Gly Asn Glu
        50                  55                  60

Tyr Gly Gly Lys Gly Phe Trp Asp Asn His His His His His
65                  70                  75
```

<210> SEQ ID NO 18
<211> LENGTH: 140
<212> TYPE: PRT
<213> ORGANISM: Artificial Sequence
<220> FEATURE:
<223> OTHER INFORMATION: Synthetic Construct

<400> SEQUENCE: 18

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 19
<211> LENGTH: 79
<212> TYPE: PRT
<213> ORGANISM: Artificial Sequence
<220> FEATURE:
<223> OTHER INFORMATION: Synthetic Construct

<400> SEQUENCE: 19

```
Met Lys Ile Asp Ala Ile Val Gly Arg Asn Ser Ala Gln Val Ile Asn
1               5                   10                  15

Thr Gly Gly Arg Ala Arg Val Gln Leu Gly Asn Val Val Thr Ala Ala
            20                  25                  30

Ala Leu His Gly Val Ala Thr Ile Ala Glu Gln Thr Thr Asn Ser Val
        35                  40                  45

Gln Val Val Asn Gly Gly Gly Glu Ser Arg Val Leu Ile Gly Asn Glu
    50                  55                  60

Tyr Gly Gly Lys Gly Phe Trp Asp Asn His His His His His
65                  70                  75
```

<210> SEQ ID NO 20
<211> LENGTH: 79
<212> TYPE: PRT
<213> ORGANISM: Artificial Sequence
<220> FEATURE:

<223> OTHER INFORMATION: Synthetic Construct

<400> SEQUENCE: 20

Met Lys Ile Asp Ala Ile Val Gly Arg Asn Ser Ala Lys Asp Ile Lys
1               5                   10                  15

Thr Val Glu Gly Ala Arg Val Gln Leu Gly Asn Val Val Thr Ala Ala
            20                  25                  30

Ala Leu His Gly Gly Ile Arg Ile Ser Asp Gln Thr Thr Asn Ser Val
        35                  40                  45

Glu Thr Val Lys Gly Val Glu Gly Ser Arg Val Leu Ile Gly Asn Glu
    50                  55                  60

Tyr Gly Gly Lys Gly Phe Trp Asp Asn His His His His His His
65                  70                  75

<210> SEQ ID NO 21
<211> LENGTH: 79
<212> TYPE: PRT
<213> ORGANISM: Artificial Sequence
<220> FEATURE:
<223> OTHER INFORMATION: Synthetic Construct

<400> SEQUENCE: 21

Met Lys Ile Asp Ala Ile Val Gly Lys Asn Gln Ala Thr Asp Ile Arg
1               5                   10                  15

Thr Glu Glu Arg Ala Arg Val Gln Leu Gly Asn Val Val Thr Ala Ala
            20                  25                  30

Ala Leu His Gly Gly Ile Arg Ile Ser Asp Gln Thr Lys Asn Gln Val
        35                  40                  45

Thr Thr Val Val Gly Lys Gly Glu Ser Arg Val Leu Ile Gly Asn Glu
    50                  55                  60

Tyr Gly Gly Lys Gly Phe Trp Asp Asn His His His His His His
65                  70                  75

<210> SEQ ID NO 22
<211> LENGTH: 79
<212> TYPE: PRT
<213> ORGANISM: Artificial Sequence
<220> FEATURE:
<223> OTHER INFORMATION: Synthetic Construct

<400> SEQUENCE: 22

Met Lys Ile Asp Ala Ile Val Gly Arg Asn Lys Ala Val Glu Ile Ala
1               5                   10                  15

Thr Glu Glu Arg Ala Arg Val Gln Leu Gly Asn Val Val Thr Ala Ala
            20                  25                  30

Ala Leu His Gly Gly Ile Arg Ile Ser Asp Gln Thr Thr Asn Lys Val
        35                  40                  45

Val Glu Val Ala Gly Lys Gly Glu Ser Arg Val Leu Ile Gly Asn Glu
    50                  55                  60

Tyr Gly Gly Lys Gly Phe Trp Asp Asn His His His His His His
65                  70                  75

<210> SEQ ID NO 23
<211> LENGTH: 323
<212> TYPE: PRT
<213> ORGANISM: Artificial Sequence
<220> FEATURE:
<223> OTHER INFORMATION: Synthetic Construct

<400> SEQUENCE: 23

Met Asn Val Ser Gln Ser Asn Ser Phe Gly Phe Trp Asp Gly Thr Ser
1               5                   10                  15

Thr Gln Ala Glu Ile Thr His Ser Phe Asp His Tyr Ile Gly Ser Ala
            20                  25                  30

Phe Asp Ala Ser Asn Asn Asn Val Ala Val Thr Gly Asn Val Ser Ala
            35                  40                  45

Thr Leu Asn Val Leu Ala Gly Asp Asp Lys Val Ser Ile Asp Gly Asn
50                  55                  60

Val Glu Asp Val Leu Val Ala Ala Asn Val Ala Val Leu Asp Met Gly
65                  70                  75                  80

Thr Gly Asn Asp Gln Leu Tyr Val Ala Gly Asp Val Leu Gly Lys Ile
                85                  90                  95

Asp Ala Gly Thr Gly Asn Asp Glu Ile Tyr Ile Lys Gly Asp Val Ser
            100                 105                 110

Ala Ala Val Asp Ala Gly Thr Gly Asn Asp Glu Val Tyr Ile Gly Gly
            115                 120                 125

Asn Leu Ser Gly Asp Leu Asp Ala Gly Thr Asp Asn Asp Asn Ile Gln
130                 135                 140

Ile Gly Gly Asp Val Asn Ala Ala Leu Asn Ala Gly Thr Gly Asn Asp
145                 150                 155                 160

Asn Leu Ile Ile Gly His Asp Val Ser Gly Ile Val Asn Met Gly Thr
                165                 170                 175

Asp Asn Asp Thr Val Glu Val Gly Arg Thr Ile Asn Ala Ser Gly Lys
            180                 185                 190

Val Leu Leu Asp Thr Gly Asp Ser Leu Leu Val Ser Gly Asp Leu
            195                 200                 205

Phe Gly Glu Val Asp Gly Gly Thr Gly Asn Asp Thr Ile Ile Ile Ala
210                 215                 220

Gly Lys Val Ser Gly Asn Ile Gln Gly Gly Thr Gly Asn Asp Ile Val
225                 230                 235                 240

Arg Val Gln Ser Gln Val Trp Ala Glu Ala Asn Ile Ser Leu Gly Thr
                245                 250                 255

Gly Asp Asp Val Leu Ile Val Glu His Glu Leu His Gly Thr Val Ala
            260                 265                 270

Gly Asn Glu Gly Asp Asp Ser Ile Tyr Leu Lys Phe Tyr Thr Lys Glu
            275                 280                 285

Gln Tyr Asn Asn Asn Ser Asp Leu Arg Asn Arg Val Ala Asn Phe Glu
            290                 295                 300

His Ile Arg Val Ser Asp Gly Val Val Lys Gly Ser Pro Ala Asp Phe
305                 310                 315                 320

Ala Asp Tyr

<210> SEQ ID NO 24
<211> LENGTH: 94
<212> TYPE: PRT
<213> ORGANISM: Artificial Sequence
<220> FEATURE:
<223> OTHER INFORMATION: Synthetic Construct

<400> SEQUENCE: 24

Met Ala His His His His His His Val Gly Thr Glu Asn Leu Tyr Phe
1               5                   10                  15

Gln Gly Asp Leu Lys Val Leu Ala Gly Asp Asp Lys Val Ser Ile Asp
            20                  25                  30

Gly Asn Val Ser Gly Ala Leu Asp Met Gly Thr Gly Asn Asp Gln Leu

```
                35                  40                  45
Tyr Val Ala Gly Asp Val Leu Gly Lys Ile Asp Ala Gly Thr Gly Asn
 50                  55                  60

Asp Glu Ile Tyr Ile Lys Gly Asp Val Ser Ala Ala Val Asp Ala Gly
 65                  70                  75                  80

Thr Gly Asn Asp Glu Val Tyr Ile Gly Gly Asn Leu Ser Lys
                 85                  90

<210> SEQ ID NO 25
<211> LENGTH: 94
<212> TYPE: PRT
<213> ORGANISM: Artificial Sequence
<220> FEATURE:
<223> OTHER INFORMATION: Synthetic Construct

<400> SEQUENCE: 25

Met Ala His His His His His Val Gly Thr Glu Asn Leu Tyr Phe
 1               5                  10                  15

Gln Gly Asp Leu Lys Val Leu Ala Gly Asp Asp Lys Val Ser Ile Asp
                 20                  25                  30

Gly Asn Val Ser Gly Ala Leu Asp Met Gly Thr Gly Asn Asp Gln Leu
             35                  40                  45

Tyr Val Ala Gly Asp Val Leu Gly Lys Ile Asp Ala Gly Thr Gly Leu
 50                  55                  60

Asp Ser Ile Met Ile Lys Gly Asp Val Ser Ala Ala Val Asp Ala Gly
 65                  70                  75                  80

Thr Gly Gln Asp Asn Val Gln Ile Gly Gly Asn Leu Ser Lys
                 85                  90

<210> SEQ ID NO 26
<211> LENGTH: 204
<212> TYPE: PRT
<213> ORGANISM: Artificial Sequence
<220> FEATURE:
<223> OTHER INFORMATION: Synthetic Construct

<400> SEQUENCE: 26

Met Ala His His His His His His Val Gly Thr Asn Thr Gly Gly Val
 1               5                  10                  15

Leu Val Ile Thr Asp Thr Ile Val Lys Ser Gly Gln Thr Tyr Asp
                 20                  25                  30

Gly Lys Gly Ile Lys Ile Ile Ala Gln Gly Met Gly Asp Gly Ser Gln
             35                  40                  45

Ser Glu Asn Gln Lys Pro Ile Phe Lys Leu Glu Lys Gly Ala Asn Leu
 50                  55                  60

Lys Asn Val Ile Ile Gly Ala Pro Gly Cys Asp Gly Ile His Cys Tyr
 65                  70                  75                  80

Gly Asp Asn Val Val Glu Asn Val Val Trp Glu Asp Val Gly Ala Asp
                 85                  90                  95

Ala Leu Thr Val Lys Ser Glu Gly Val Val Glu Val Ile Gly Gly Ser
                100                 105                 110

Ala Lys Glu Ala Ala Asp Lys Val Phe Gln Leu Asn Ala Pro Cys Thr
             115                 120                 125

Phe Lys Val Lys Asn Phe Thr Ala Thr Asn Ile Gly Lys Leu Val Arg
         130                 135                 140

Gln Asn Gly Asn Thr Thr Phe Lys Val Val Ile Tyr Leu Glu Asp Val
145                 150                 155                 160
```

Thr Leu Asn Asn Val Lys Ser Cys Val Ala Lys Ser Asp Ser Pro Val
            165                 170                 175

Ser Glu Leu Trp Tyr His Asn Leu Asn Val Asn Asn Cys Lys Thr Leu
            180                 185                 190

Phe Glu Phe Pro Ser Gln Ser Gln Ile His Gln Tyr
            195                 200

<210> SEQ ID NO 27
<211> LENGTH: 204
<212> TYPE: PRT
<213> ORGANISM: Artificial Sequence
<220> FEATURE:
<223> OTHER INFORMATION: Synthetic Construct

<400> SEQUENCE: 27

Met Ala His His His His His His Val Gly Thr Asn Thr Gly Gly Val
1               5                   10                  15

Leu Val Ile Thr Asp Thr Ile Ile Val Lys Ser Gly Gln Thr Tyr Asp
            20                  25                  30

Gly Lys Gly Ile Lys Ile Ile Ala Gln Gly Met Gly Asp Gly Ser Gln
        35                  40                  45

Ser Glu Asn Gln Lys Pro Ile Phe Lys Leu Glu Lys Gly Ala Asn Leu
    50                  55                  60

Lys Asn Val Ile Ile Gly Ala Pro Gly Cys Asp Gly Ile His Cys Tyr
65                  70                  75                  80

Gly Asp Asn Val Val Glu Asn Val Val Trp Glu Asp Val Gly Ala Asp
            85                  90                  95

Ala Leu Thr Val Lys Ser Glu Gly Val Val Glu Val Ile Lys Gly Asn
            100                 105                 110

Ala Lys His Ala Ala Asp Lys Val Phe Gln Leu Asn Ala Pro Cys Thr
        115                 120                 125

Phe Lys Val Lys Asn Phe Asp Ala Glu Asp Ile Gly Lys Leu Val Arg
    130                 135                 140

Gln Asn Gly Asn Thr Thr Phe Lys Val Val Ile Tyr Leu Glu Lys Val
145                 150                 155                 160

Asn Leu Lys His Val Lys Ser Cys Val Ala Lys Ser Asp Ser Pro Val
            165                 170                 175

Ser Glu Leu Trp Tyr His Asn Leu Asp Val Glu Asp Cys Lys Thr Leu
            180                 185                 190

Phe Glu Phe Pro Ser Gln Ser Gln Ile His Gln Tyr
            195                 200

<210> SEQ ID NO 28
<211> LENGTH: 204
<212> TYPE: PRT
<213> ORGANISM: Artificial Sequence
<220> FEATURE:
<223> OTHER INFORMATION: Synthetic Construct

<400> SEQUENCE: 28

Met Ala His His His His His His Val Gly Thr Asn Thr Gly Gly Val
1               5                   10                  15

Leu Val Ile Thr Asp Thr Ile Ile Val Lys Ser Gly Gln Thr Tyr Asp
            20                  25                  30

Gly Lys Gly Ile Lys Ile Ile Ala Gln Gly Met Gly Asp Gly Ser Gln
        35                  40                  45

Ser Glu Asn Gln Lys Pro Ile Phe Lys Leu Glu Lys Gly Ala Asn Leu
    50                  55                  60

```
Lys Asn Val Ile Ile Gly Ala Pro Gly Cys Asp Gly Ile His Cys Tyr
 65                  70                  75                  80

Gly Asp Asn Val Val Glu Asn Val Val Trp Glu Asp Val Gly Ala Asp
                 85                  90                  95

Ala Leu Thr Val Lys Ser Glu Gly Val Val Glu Val Ile Gly Gly Asp
            100                 105                 110

Ala Glu Asp Ala Ala Asp Lys Val Phe Gln Leu Asn Ala Pro Cys Thr
        115                 120                 125

Phe Lys Val Lys Lys Phe Asn Ala Lys His Ile Gly Lys Leu Val Arg
130                 135                 140

Gln Asn Gly Asn Thr Thr Phe Lys Val Val Ile Tyr Leu Glu Asp Val
145                 150                 155                 160

Asp Leu Glu Asp Val Lys Ser Cys Val Ala Lys Ser Asp Ser Pro Val
                165                 170                 175

Ser Glu Leu Trp Tyr His Lys Leu Asn Val Lys His Cys Lys Thr Leu
            180                 185                 190

Phe Glu Phe Pro Ser Gln Ser Gln Ile His Gln Tyr
        195                 200

<210> SEQ ID NO 29
<211> LENGTH: 373
<212> TYPE: PRT
<213> ORGANISM: Artificial Sequence
<220> FEATURE:
<223> OTHER INFORMATION: Synthetic Construct

<400> SEQUENCE: 29

Ser Gly Leu Gln Gly Met Asp Val Val His Gly Thr Ala Thr Met Gln
 1               5                  10                  15

Val Asp Gly Asn Lys Thr Ile Ile Arg Asn Ser Val Asp Ala Ile Ile
                 20                  25                  30

Asn Trp Lys Gln Phe Asn Ile Asp Gln Asn Glu Met Val Gln Phe Leu
            35                  40                  45

Gln Glu Asn Asn Asn Ser Ala Val Phe Asn Arg Val Thr Ser Asn Gln
        50                  55                  60

Ile Ser Gln Leu Lys Gly Ile Leu Asp Ser Asn Gly Gln Val Phe Leu
 65                  70                  75                  80

Ile Asn Pro Asn Gly Ile Thr Ile Gly Lys Asp Ala Ile Ile Asn Thr
                 85                  90                  95

Asn Gly Phe Thr Ala Ser Thr Leu Asp Ile Ser Asn Glu Asn Ile Lys
            100                 105                 110

Ala Arg Asn Phe Thr Phe Glu Gln Thr Lys Asp Lys Ala Leu Ala Glu
        115                 120                 125

Ile Val Asn His Gly Leu Ile Thr Val Gly Lys Asp Gly Ser Val Asn
130                 135                 140

Leu Ile Gly Gly Lys Val Lys Asn Glu Gly Val Ile Ser Val Asn Gly
145                 150                 155                 160

Gly Ser Ile Ser Leu Leu Ala Gly Gln Lys Ile Thr Ile Ser Asp Ile
                165                 170                 175

Ile Asn Pro Thr Ile Thr Tyr Ser Ile Ala Ala Pro Glu Asn Glu Ala
            180                 185                 190

Val Asn Leu Gly Asp Ile Phe Ala Lys Gly Gly Asn Ile Asn Val Arg
        195                 200                 205

Ala Ala Thr Ile Arg Asn Gln Gly Lys Leu Ser Ala Asp Ser Val Ser
210                 215                 220
```

```
Lys Asp Gly Ser Gly Asn Ile Val Leu Ser Ala Lys Glu Gly Glu Ala
225                 230                 235                 240

Glu Ile Gly Gly Val Ile Ser Ala Gln Asn Gln Ala Lys Gly Gly
                245                 250                 255

Lys Leu Met Ile Thr Gly Asp Lys Val Thr Leu Lys Thr Gly Ala Val
            260                 265                 270

Ile Asp Leu Ser Gly Lys Glu Gly Glu Thr Tyr Leu Gly Gly Asp
            275                 280                 285

Glu Arg Gly Glu Gly Lys Asn Gly Ile Gln Leu Ala Lys Lys Thr Ser
            290                 295                 300

Leu Glu Lys Gly Ser Thr Ile Asn Val Ser Gly Lys Glu Lys Gly Gly
305                 310                 315                 320

Arg Ala Ile Val Trp Gly Asp Ile Ala Leu Ile Asp Gly Asn Ile Asn
                325                 330                 335

Ala Gln Gly Ser Gly Asp Ile Ala Lys Thr Gly Gly Phe Val Glu Thr
                340                 345                 350

Ser Gly His Asp Leu Phe Ile Lys Asp Asn Ala Ile Val Asp Ala Lys
            355                 360                 365

Glu Trp Leu Leu Asp
    370

<210> SEQ ID NO 30
<211> LENGTH: 100
<212> TYPE: PRT
<213> ORGANISM: Artificial Sequence
<220> FEATURE:
<223> OTHER INFORMATION: Synthetic Construct

<400> SEQUENCE: 30

Met Ala His His His His His His Val Gly Thr Glu Asn Leu Tyr Phe
1               5                   10                  15

Gln Gly Lys Glu Ile Val Asn His Gly Leu Ile Thr Val Gly Asp Gly
            20                  25                  30

Ser Val Asn Leu Ile Gly Gly Lys Val Lys Asn Glu Gly Val Ile Ser
        35                  40                  45

Val Asn Gly Gly Ser Ile Ser Leu Leu Ala Gly Glu Ala Val Asn Leu
    50                  55                  60

Gly Asp Ile Phe Ala Lys Gly Gly Asn Ile Asn Val Arg Ala Ala Thr
65                  70                  75                  80

Ile Arg Asn Gln Gly Lys Leu Ser Ala Gly Lys Gly Asn Ile Val Leu
                85                  90                  95

Ser Ala Gly Glu
            100

<210> SEQ ID NO 31
<211> LENGTH: 349
<212> TYPE: PRT
<213> ORGANISM: Artificial Sequence
<220> FEATURE:
<223> OTHER INFORMATION: Synthetic Construct

<400> SEQUENCE: 31

Asp Pro Cys Ser Val Thr Glu Tyr Ser Gly Leu Ala Thr Ala Val Ser
1               5                   10                  15

Ser Cys Lys Asn Ile Val Leu Asn Gly Phe Gln Val Pro Thr Gly Lys
            20                  25                  30

Gln Leu Asp Leu Ser Ser Leu Gln Asn Asp Ser Thr Val Thr Phe Lys
```

```
            35                  40                  45
Gly Thr Thr Thr Phe Ala Thr Thr Ala Asp Asn Asp Phe Asn Pro Ile
 50                  55                  60

Val Ile Ser Gly Ser Asn Ile Thr Ile Thr Gly Ala Ser Gly His Val
 65                  70                  75                  80

Ile Asp Gly Asn Gly Gln Ala Tyr Trp Asp Gly Lys Gly Ser Asn Ser
                 85                  90                  95

Asn Ser Asn Gln Lys Pro Asp His Phe Ile Val Val Gln Lys Thr Thr
            100                 105                 110

Gly Asn Ser Lys Ile Thr Asn Leu Asn Ile Gln Asn Trp Pro Val His
        115                 120                 125

Cys Phe Asp Ile Thr Gly Ser Ser Gln Leu Thr Ile Ser Gly Leu Ile
130                 135                 140

Leu Asp Asn Arg Ala Gly Asp Lys Pro Asn Ala Lys Ser Gly Ser Leu
145                 150                 155                 160

Pro Ala Ala His Asn Thr Asp Gly Phe Asp Ile Ser Ser Ser Asp His
                165                 170                 175

Val Thr Leu Asp Asn Asn His Val Tyr Asn Gln Asp Asp Cys Val Ala
            180                 185                 190

Val Thr Ser Gly Thr Asn Ile Val Val Ser Asn Met Tyr Cys Ser Gly
        195                 200                 205

Gly His Gly Leu Ser Ile Gly Ser Val Gly Gly Lys Ser Asp Asn Val
210                 215                 220

Val Asp Gly Val Gln Phe Leu Ser Ser Gln Val Val Asn Ser Gln Asn
225                 230                 235                 240

Gly Cys Arg Ile Lys Ser Asn Ser Gly Ala Thr Gly Thr Ile Asn Asn
                245                 250                 255

Val Thr Tyr Gln Asn Ile Ala Leu Thr Asn Ile Ser Thr Tyr Gly Val
            260                 265                 270

Asp Val Gln Gln Asp Tyr Leu Asn Gly Gly Pro Thr Gly Lys Pro Thr
        275                 280                 285

Asn Gly Val Lys Ile Ser Asn Ile Lys Phe Ile Lys Val Thr Gly Thr
290                 295                 300

Val Ala Ser Ser Ala Gln Asp Trp Phe Ile Leu Cys Gly Asp Gly Ser
305                 310                 315                 320

Cys Ser Gly Phe Thr Phe Ser Gly Asn Ala Ile Thr Gly Gly Gly Lys
                325                 330                 335

Thr Ser Ser Cys Asn Tyr Pro Thr Asn Thr Cys Pro Ser
            340                 345

<210> SEQ ID NO 32
<211> LENGTH: 121
<212> TYPE: PRT
<213> ORGANISM: Artificial Sequence
<220> FEATURE:
<223> OTHER INFORMATION: Synthetic Construct

<400> SEQUENCE: 32

Met Ala His His His His His His Val Gly Thr Glu Asn Leu Tyr Phe
 1               5                  10                  15

Gln Gly Asp Gly Phe Asp Ile Ser Ser Ser Asp His Val Thr Leu Asp
                 20                  25                  30

Asn Asn His Val Tyr Asn Gln Asp Asp Cys Val Ala Val Thr Ser Gly
             35                  40                  45

Thr Asn Ile Val Val Ser Asn Met Tyr Cys Ser Gly Gly His Gly Leu
```

```
                50                  55                  60

Ser Ile Gly Ser Val Gly Lys Ser Asp Asn Val Asp Gly Val
65                  70                  75                  80

Gln Phe Leu Ser Ser Gln Val Val Asn Ser Gln Asn Gly Cys Arg Ile
                    85                  90                  95

Lys Ser Asn Ser Gly Ala Thr Gly Thr Ile Asn Asn Val Thr Tyr Gln
                100                 105                 110

Asn Ile Ala Leu Thr Asn Ile Ser Arg
        115                 120
```

<210> SEQ ID NO 33
<211> LENGTH: 151
<212> TYPE: PRT
<213> ORGANISM: Artificial Sequence
<220> FEATURE:
<223> OTHER INFORMATION: Synthetic Construct

<400> SEQUENCE: 33

```
Met Lys Ile Asp Ala Ile Val Gly Arg Asn Ser Ala Lys Asp Ile Arg
1               5                   10                  15

Thr Glu Glu Arg Ala Arg Val Gln Leu Gly Asn Val Val Thr Ala Ala
                20                  25                  30

Ala Leu His Gly Gly Ile Arg Ile Ser Asp Gln Thr Thr Asn Cys Val
            35                  40                  45

Glu Thr Val Val Gly Lys Gly Glu Ser Arg Val Leu Ile Gly Asn Glu
        50                  55                  60

Tyr Gly Gly Lys Gly Phe Trp Asp Asn Gly Gly Gly Gly Gly Gly Gly
65                  70                  75                  80

Ala Ala Gly Gly Gly Gly Asn Ser Ala Lys Asp Ile Arg Thr Glu
                85                  90                  95

Glu Arg Ala Arg Val Gln Leu Gly Asn Val Val Thr Ala Ala Ala Leu
                100                 105                 110

His Gly Gly Ile Arg Ile Ser Asp Gln Thr Thr Asn Ser Val Glu Thr
            115                 120                 125

Val Val Gly Lys Gly Glu Ser Arg Val Leu Ile Gly Asn Glu Tyr Gly
        130                 135                 140

Gly Lys Gly Phe Trp Asp Asn
145                 150
```

<210> SEQ ID NO 34
<211> LENGTH: 152
<212> TYPE: PRT
<213> ORGANISM: Artificial Sequence
<220> FEATURE:
<223> OTHER INFORMATION: Synthetic Construct

<400> SEQUENCE: 34

```
Met Lys Ile Asp Ala Ile Val Gly Arg Asn Ser Ala Lys Tyr Ile Asp
1               5                   10                  15

Thr Glu Asp Arg Ala Glu Val Gln Leu Gly Asn Val Val Thr Ala Ala
                20                  25                  30

Ala Leu His Gly Gly Ile Arg Ile Ser Asp Gln Thr Thr Asn Ser Val
            35                  40                  45

Glu Lys Val Asn Gly Lys His Glu Ser Arg Val Arg Leu Ile Gly Asn
        50                  55                  60

Glu Tyr Gly Gly Lys Gly Phe Trp Asp Asn Gly Gly Gly Gly Gly
65                  70                  75                  80
```

```
Gly Ala Ala Gly Gly Gly Gly Asn Ser Ala Lys Tyr Ile Asp Thr
                85                  90                  95

Glu Asp Arg Ala Glu Val Gln Leu Gly Asn Val Val Thr Ala Ala Ala
            100                 105                 110

Leu His Gly Gly Ile Arg Ile Ser Asp Gln Thr Thr Asn Ser Val Glu
        115                 120                 125

Lys Val Asn Gly Lys His Glu Ser Arg Val Leu Ile Gly Asn Glu Tyr
    130                 135                 140

Gly Gly Lys Gly Phe Trp Asp Asn
145                 150

<210> SEQ ID NO 35
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

Gly Lys Met Gly Gly Arg Phe Tyr Phe Asp Tyr
1               5                   10
```

INNOCUOUS, STRUCTURED SCAFFOLDS FOR STRUCTURE-BASED AMYLOID DISEASE VACCINES AND ANTIGENS

SEQUENCE LISTING

The instant application contains a Sequence Listing which has been submitted electronically in ASCII format and is hereby incorporated by reference in its entirety. Said ASCII copy, created on May 3, 2021, is named "51012-036001_Sequence_Listing_05.03.21_ST25" and is 39,937 bytes in size.

FIELD

The present disclosure relates generally to polypeptides which may be used of the treatment of neurological diseases or disorders.

BACKGROUND

Prior attempts, by a large number of researchers and companies, to create vaccines and specific antigens for protein misfolding diseases such as Chronic Wasting Disease (CWD), Bovine Spongiform Encephalopathy (SSE), Creutzfeldt-Jakob Disease (CJD), Alzheimer Disease's (AD), or Parkinson's Disease (PD) relied on full-length proteins or short peptides derived from the disease-causing proteins. These antigens and vaccines were not designed to adopt and maintain a specific structure when used in vivo, in particular they were not designed to adopt a defined beta-structure with specific residues forming a beta-structured protein surface (epitope). Moreover, all of these proteins and peptides (antigens) were defined as contiguous sequences derived from the disease-causing protein or peptide.

SUMMARY

In one aspect there is provided an isolated recombinant polypeptide, comprising or consisting of: a (3-solenoid structured polypeptide comprising amino acids from an innocuous (3-solenoid scaffold polypeptide and a plurality of epitope amino acids from a disease associated polypeptide with exposed side chains that project or are predicted to project to an exterior position of the (3-solenoid domain, said plurality of epitope amino acids define an epitope from the disease associated polypeptide, preferably said plurality of epitope amino acids are every second residue in a β-strand of said (3-solenoid scaffold polypeptide.

In one example, said β-solenoid structured polypeptide comprises one or more β-arcs, comprising a plurality of said epitope amino acids from said disease associated polypeptide from the disease associated polypeptide.

In one example, further comprising a linker domain and a second β-solenoid structured polypeptide, said linker domain positioned between said β-solenoid structured polypeptide and said second β-soienoid structured polypeptide, said second β-solenoid structured polypeptide comprising a β-solenoid scaffold domain and a plurality of epitope amino acids from a disease associated polypeptide with exposed side chains that project or are predicted to project to an exterior position of the β-solenoid domain, said plurality of epitope amino acids define an epitope from the disease associated polypeptide.

In one example, said linker comprises 10 to 16 amino acids.

In one example, said β-solenoid scaffold polypeptide comprises or consists of a β-solenoid sequence from Het-s, Het-2s, pectate lyase 3, Ca2+-dependent beta-helical anti-freeze protein, HMW adhesin, Poly(beta-D-mannuronate) C5 epimerase 4, or endopolygalacturonase.

In one example, said β-solenoid scaffold polypeptide comprises or consists of a polypeptide having a sequence as set forth in SEQ ID NOs: 1, 11, 24, 26, 30, or 32.

In one example, said disease associated polypeptide is PrPSc, microtubule-associated protein tau, α-synucleWn, PrP, Aβ, or β-2-microglobulin.

In one example, said β-solenoid domain polypeptide is left-handed.

In one example, said β-solenoid domain polypeptide is right-handed.

In one example, said β-solenoid domain polypeptide comprises a seven-rung, a four-rung or a two-rung β-solenoid domain.

In one example, further comprising or consisting of a purification domain.

In one example, said purification domain comprises a plurality of His amino acids.

In one aspect there is provided an isolated recombinant polypeptide, comprising of or consisting of the amino acid sequence (SEQ ID NO: 33)
```
MKIDAIVGRNSAKDIRTEERARVQLGNVVTAAALHGGIRISDQTTNSVE

TVVGKGESRVLIGNEYGGKGFWDNGGGGGGGAAGGGGGNSAKDIRTEER

ARVQLGNVVTAAALHGGIRISDQTTNSVETVVGKGESRVLIGNEYGGKG

FWDN
```

In one aspect there is provided an isolated recombinant polypeptide, comprising or consisting of the amino acid sequence (SEQ ID NO: 1)
```
MKIDAIVGRNSAKDIRTEERARVQLGNVVTAAALHGGIRISDQTINSVE

TVVGKGESRVLIGNEYGGKGFWDNGGGGGGGAAGGGGGNSAKDIRTEER

ARVQLGNVVTAAALHGGIRISDQTTNSVETVVGKGESRVLIGNEYGGKG

FWDNHHHHHH.
```

In one aspect there is provided an isolated recombinant polypeptide, comprising of or consisting of the amino acid sequence (SEQ ID NO: 3)
```
MKIDAIVGRNSAKYIDTEDRAEVQLGNVVTAAALHGGIRISDQTTNSVE

KVNGKHESRVLIGNEYGGKGFWDNGGGGGGGAAGGGGGNSAKYIDTEDR

AEVQLGNVVTAAALHGGIRISDQTTNSVEKVNGKHESRVLIGNEYGGKG

FWDNHHHHHH.
```

In one aspect there is provided an isolated recombinant polypeptide, comprising or consisting of the amino acid sequence (SEQ ID NO: 34)
MKIDAIVGRNSAKYIDTEDRAEVQLGNVVTAAALHGGIRISDQTINSVE

KVNGKHESRVLIGNEYGGKGFWDNGGGGGGGAAGGGGGNSAKYIDTEDR

AEVQLGNVVTAAALHGGIRISDQTTNSVEKVNGKHESRVLIGNEYGGKG

FWDN.

In one aspect there is provided an isolated recombinant polypeptide, comprising or consisting of the amino acid sequence set forth in SED ID NOs: 3, 19, 20, 21, 22, 25, 27, or 28.

In one example, said prion related disease or disorder, or said neurodegenerative disease or disorder, or said proteinopathy, is Alzheimer's disease (AD), Parkinson's disease (PD), Lewy Body Dementia (LBD), Multiple System Atrophy (MSA), Huntington's disease (HD), amyotrophic lateral sclerosis (ALS), Creutzfeldt-Jakob disease (CJD), Ataxia Telangiectasia Friedrelch's Ataxia, Multiple Sclerosis (MS), Prion diseases, Spinocerebellar Ataxia (SCA), Spinal Muscular Atrophy (SMA), Traumatic Brain Injury, spongiform encephalopathies (TSE), Creutzfeldt-Jakob disease (CJD), new variant CJD, Kuru, Gerstmann-StrAussler-Scheinker syndrome (GSS), fatal familial Insomnia (FFI), dialysis-related amyloidosis (DRA) in humans, scrapie in sheep and goats, spongiform encephalopathy in cattle, or chronic wasting disease(CWD) in cervids.

In one example, said subject is a human or an animal.

In one example, said prion related disease or disorder, or said neurodegenerative disease or disorder, or said proteinopathy, is Alzheimer's disease (AD), Parkinson's disease (PD), Lewy body dementia (LBD), Multi Systems Atrophy (MSA), Huntington's disease (HD), amyotrophic lateral sclerosis (ALS), Creutzfeldt-Jakob disease (CJD), Ataxia Telangiectasia Friedreich's Ataxia, Multiple Sclerosis (MS), Prion diseases, Spinocerebellar Ataxia (SCA), Spinal Muscular Atrophy (SMA), Traumatic Brain Injury, spongiform encephalopathies (TSE), Creutzfeldt-Jakob disease (CJD), new variant CJD, Kuru, Gerstmann-Sträussler-Scheinker syndrome (GSS), fatal familial insomnia (FFI), dialysis-related amyloidosis (DRA) In humans, scrapie In sheep and goats, spongiform encephalopathy in cattle, or chronic wasting disease(CWD) in cervids.

In one example, said subject is a human or an animal.

BRIEF DESCRIPTION OF THE DRAWINGS

Embodiments of the present disclosure will now be described, by way of example only, with reference to the attached Figures.

FIG. 9 The structure of three HET-s molecules with the amino acid changes of the 14R1 vaccine candidate represented as stick-and-ball side chains and black color. The structure of HET-s is shown as a ribbon diagram (left), and in a space-filling view (right). The HET-s 14R1 modifications were modeled onto the structure of the native HET-s (218-289) prion domain in the prion state. PDB access code: 2RNM, for the HET-s(218-289) structure (Wasmer et al., 2008).

FIG. 15 Primary structure of the 61D8 antibody as determined from cDNA that was prepared from the 61D8-expressing hybridoma cells. The nucleotide sequence was translated into the respective protein sequence and the complementarity determining regions (CDRs) were identified based on the conserved sequences that frame both the heavy and light chain CDRs. As second monoclonal antibody (63G4) that was generated independently from another immunized mouse was found to have the identical primary structure, indicating the prominence of the epitope and the reproducibility of the immune response using the 14R1 antigen.

FIG. 28 Competitive ELISA to test the specificity of the immune response obtained with vaccine candidates α-SC8 and α-SC9. Brain homogenates from three separate patients suffering from Lewy body dementia (LBD), Multi systems atrophy (MSA), and Parkinson's disease (PD) were analyzed using the post-immune serum from mice immunized with α-SC8 and α-SC8. In both cases, the vaccine candidate-induced immune response recognized all disease-associated patient-derived samples, indicating the antigens Induced an immune response against an α-synuclein epitope.

FIG. 32 Vaccine scaffold protein: HET-2s. Duplicated construct containing the prion domain (residues 218-289) of the fungal prion protein HET-s. A glycine rich linker (bold and underlined) connects the two protein halves. A histidine tag at the C-terminus (bold only) facilitates the purification.

FIG. 33 Vaccine scaffold protein: HET-s. Prion domain (residues 218-289) of the fungal prion protein HET-s. A histidine tag at the C-terminus (bold font) facilitates the purification.

FIG. 34 Vaccine candidate: 14R1 (prion disease). (Above) Deer PrP sequence: residues for HET-2s_14R1 in taller, bold font. (Below) Adapted HET-2s sequence for 14R1: residues from deer PrP in taller, bold font.

FIG. 35 Vaccine candidate: AβC3 (Alzheimer's disease). (Above) Aβ(1-42) sequence: residues for HET-s_AβC3 in taller, bold font. (Below) Adapted HET-s sequence for AβC3: residues from Aβ(1-42) in taller, bold font.

FIG. 36 Vaccine candidate: AβC4 (Alzheimer's disease). (Above) Aβ6(1-42) sequence: residues for HET-s_AβC4 in taller, bold font. (Below) Adapted HET-s sequence for AβC4: residues from Aβ(1-42) in taller, bold font.

FIG. 37 Vaccine candidate: TauC3 (Alzheimer's disease & tauopathies). (Above) partial Tau sequence: residues for HET-s_TauC3 in taller, bold font. (Below) Adapted HET-s sequence for TauC3: residues from tau in taller, bold font.

FIG. 38 Vaccine candidate: TauC4 (Alzheimer's disease & tauopathies). (Above) partial Tau sequence: residues for HET-s_TauC4 in taller, bold font. (Below) Adapted HET-s sequence for TauC4: residues from tau in taller, bold font.

FIG. 39 Vaccine candidate: α-SC3 (Parkinson's disease & synucleinopathies). (Above) Alpha-synuclein sequence: residues for HET-s_α-SC3 in taller, bold font. (Below) Adapted HET-s sequence for α-SC3: residues from alpha-synuclein In taller, bold font.

FIG. 40 Vaccine candidate: α-SC6 (Parkinson's disease & synucleinopathies). (Above) Alpha-synuclein sequence: residues for HET-s_α-SC6 in taller, bold font. (Below) Adapted HET-s sequence for α-SC6: residues from alpha-synuclein in taller, bold font.

FIG. 41 Vaccine candidate: α-SC8 (Parkinson's disease & synucleinopathies). (Above) Alpha-synuclein sequence: residues for HET-s_α-SC8 in taller, bold font. (Below) Adapted HET-s sequence for α-SC8: residues from alpha-synuclein in taller, bold font.

FIG. 42 Vaccine candidate: α-SC9 (Parkinson's disease & synucleinopathies). (Above) Alpha-synuclein sequence: residues for HET-s_α-SC9 in taller, bold font. (Below) Adapted HET-s sequence for α-SC9: residues from alpha-synuclein in taller, bold font.

FIG. 43 Vaccine scaffold protein: 3P4G-Vac. (Above) Antifreeze protein sequence from an Antarctic bacterium, *Marinomonas primoryensis* (PDB #: 3P4G). (Below) Sequence of 3P4G-Vac: a four-rung, right-handed n-solenoid vaccine scaffold: Residues that were changed in order to enable the protein to fibrillize in the designed manner are indicated as follows: 1) Histidine tag to facilitate the purification: taller, bold font; 2) TEV cleavage site: taller, italic font; 3) Charged residues to facilitate fibrillization through the formation of salt bridges: taller, bold, underlined font; 4) "SGA" loop connecting the two protein fragments: taller font only.

FIG. 44 Vaccine candidate: 3P4G-C7 (prion disease). (Above) Deer PrP sequence: residues for 3P4G-C7 in taller, bold font. (Below) 3P4G-C7 sequence: residues from deer PrP in taller, bold font.

FIG. 45 Vaccine scaffold protein: PL3-Vac. Pectate lyase sequence from family 3 (PDB: 4Z05): protein used in full-length as a right-handed β-solenoid vaccine scaffold. The whole protein was used as a soluble vaccine scaffold that does not form amyloid fibrils. Structural integrity of the vaccine candidates was determined via circular dichroism spectroscopy.

FIG. 46 Vaccine candidate: PL3C1 (prion disease). (Above) Deer PrP sequence: residues for PL3C1 in taller, bold font. (Below) Adapted PL3-Vac sequence for PL3C1: residues from deer PrP in taller, bold font.

FIG. 47 Vaccine candidate: PL3C2 (prion disease). (Above) Deer PrP sequence: residues for PL3C2 in taller, bold font. (Below) Adapted PL3-Vac sequence for PL3C2: residues from deer PrP in taller, bold font.

FIG. 48 Vaccine scaffold protein: 2ODL-Vac. (Above) HMW1 secretion domain sequence from *Haemophilus influenzae* (PDB #: 2ODL): residues that were selected to create a for 4-rung, right-handed β-solenoid vaccine scaffold are shown in taller, bold font. (Below) Sequence of 2ODL-Vac: a four-rung, right-handed β-solenoid vaccine scaffold. Residues that were changed in order to enable the protein to fibrillize in the designed manner are Indicated as follows: 1) Histidine tag to facilitate the purification: taller, bold font; 2) TEV cleavage site: taller, italic font; 3) Charged residues to facilitate fibrillization through the formation of salt bridges: taller, bold, underlined font; 4) Removal of a charge residue to facilitate fibrillization: tall font only.

FIG. 49 Vaccine scaffold protein: 1HG8-Vac. (Above) Endopolygalacturonase sequence from fungus *Fusarium moniliforme* (PDB #: 1HG8): residues used to create a for 4-rung, right-handed β-solenoid vaccine scaffold are shown in taller, bold font. (Below) Sequence of 1HG8-Vac: a four-rung, right-handed β-solenoid vaccine scaffold. Residues that were changed in order to enable the protein to fibrillize in the designed manner are indicated as follows: 1) Histidine tag to facilitate the purification: taller, bold font; 2) TEV cleavage site: taller, italic font; 3) Charged residues to facilitate fibrillization through the formation of salt bridges: taller, bold, underlined font.

DETAILED DESCRIPTION

Figure 1:
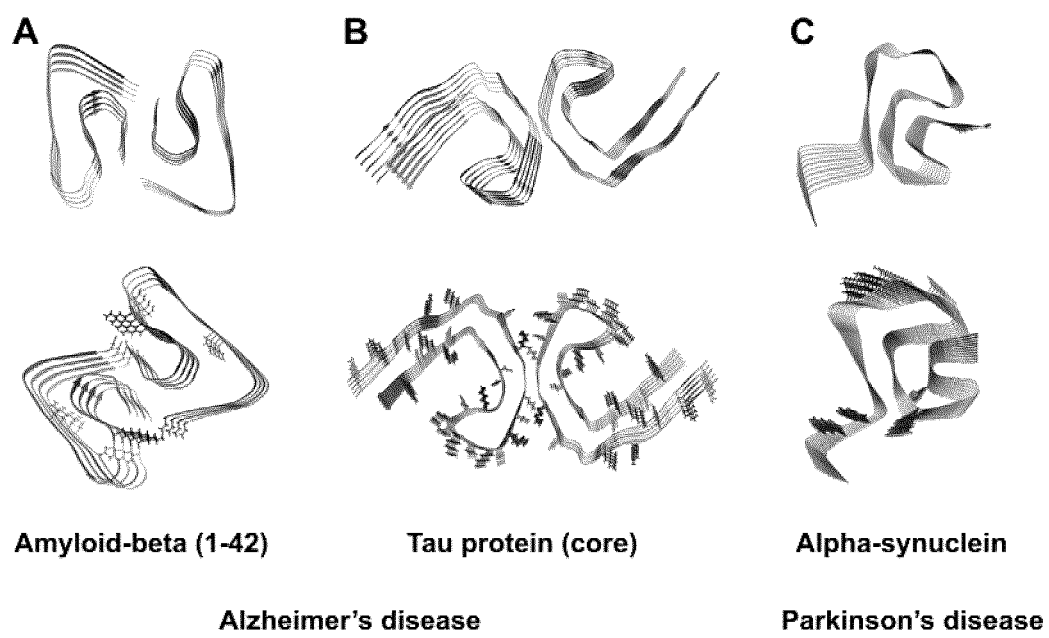
FIG. 1: The structures of misfolded proteins responsible for Alzheimer's disease and Parkinson's disease. Cryo electron microscopy and solid-state NMR spectroscopy allowed to solve the structures of amyloid fibrils formed by the amyloid-beta peptide (residues 1-42) (A), the core of the tau protein (B), and the core of alpha-synuclein (C). In all three cases, the misfolded proteins adopt an in-register, parallel, cross-beta structure, where every molecule sits on top of its predecessor along the fibril axis in exactly the same orientation. The top figures show the cross-section of individual amyloid fibrils in a peptide backbone view, while the bottom figures include some side-chains that alternate in their orientation towards the exterior and interior of the fibrils. (A) Cryo electron microscopy structure of amyloid-beta peptide (1-42), PDB access code: 5OQV (Gremer et al., 2017). (B) Cryo electron microscopy structure of paired helical filaments containing the core of the tau protein, PDB access code: 5O3L (Fitzpatrick et al., 2017). (C) Solid-state NMR spectroscopy structure of core of alpha-synuclein, PDB access code: 2N0A (Tuttle et al., 2016).
Figure 2:
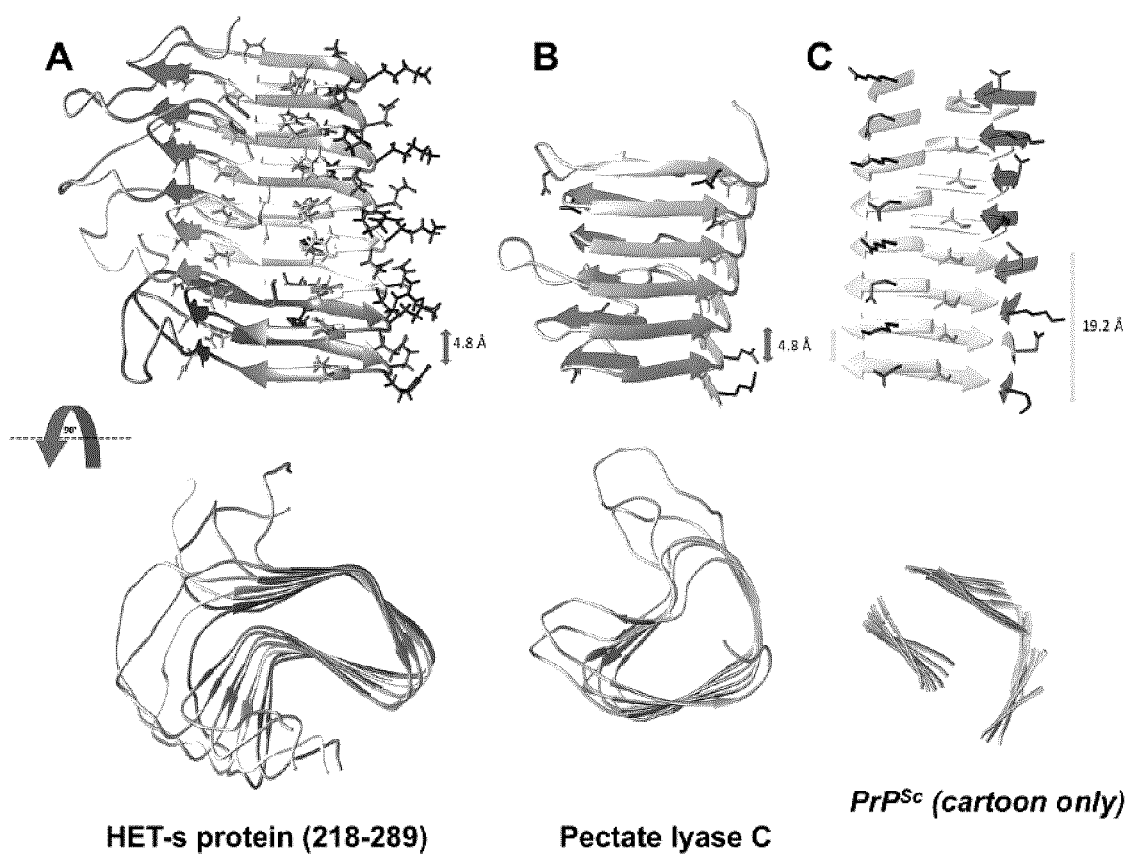
FIG. 2 Structures of scaffold proteins that were used to develop the structure-based antigens/vaccine candidates, and the architecture of the Infectious prion protein for comparison. (A) Solid-state NMR spectroscopy structure of the prion domain of the fungal HET-s prion protein (residues 218-289) in its amyloid fibril/prion state. PDB access code: 2RNM (Wasmer et al., 2008). Outward facing residues that contribute to the stability of the fold are indicated as stick figures (top row). (B) Crystal structure of the beta-solenoid portion of pectate lyase (residues 118 to 285). Outward facing residues that can be manipulated to stabilize the beta-solenoid fold are shown as stick figures (top row). PDB access code: 2PEC (Yoder & Jumak, 1995). (C) Cartoon depicting the overall architecture of the infectious prion protein containing a four-rung beta-solenoid fold. Only the predicted beta-strands are shown, since little to no information is available about the connecting loops (Wille et al., 2009; Vázquez-Fernández et al., 2016).

Generally, the present disclosure provides polypeptides which may be used of the treatment of neurological diseases or disorders.

Many neurodegenerative diseases are linked to intracellular and/or extracellular accumulation of specific protein aggregates, which can be referred to as proteinopathy-induced neurodegeneration or proteinopathy-induced neurodegenerative disease. In many cases, it is thought that the protein aggregates exert toxic effects on the brain, and contribute to disease pathology.

The term "proteinopathy" or "proteinopathic" may refer to a disease, disorder, and/or condition associated with the pathogenic aggregation and/or accumulation of one or more types of proteins, for example, but not limited to α-synuclein, β-amyloid, and/or tau proteins. In some embodiments, a proteinopathy is characterized by an anomaly in one or more of protein production, folding, aggregation, metabolism, or degradation (e.g. autophagy), transportation or trafficking, secretion, etc. In some embodiments, proteinopathies are neurodegenerative diseases. Specific pathologies such as synucleinopathies, tauopathies, amyloidopathies, TDP-43 proteinopathies and others are examples of proteinopathies. Exemplary proteins implicated in proteinopathies Include: α-synuclein in the case of Parkinson's disease, Lewy body disease, and other synucleinopathies; tau and β-amyloid in the case of Alzheimer's disease and certain other neurodegenerative diseases; SOD1 and TDP-43 in the case of amyotrophic lateral sclerosis; huntingtin in the case of Huntington's disease; rhodopsin in the case of retinitis pigmentosa; and proteins involved in lysosomal storage diseases.

In some examples, there is provided Isolated recombinant polypeptide for treating a subject having or suspected of having or at risk of developing a prion related disease or disorder, a neurodegenerative disease or disorder, or a proteinopathy.

The term "neurodegeneration" may refer to the progressive loss of individual or collective structure or function of neurons, up to and including the death of neurons that is associated with many neurodegenerative diseases. For example, "neurodegenerative disease(s)" or "neurodegenerative disorder" can refer to medical conditions that are characterized clinically by their insidious onset and chronic progression. In many Instances, particular parts of the brain, spinal cord, or peripheral nerves functionally fail and the neurons of the dysfunctional region die. Neuroanatomically localizable functional impairment and "neurodegeneration" associate with recognizable syndromes or conditions that are Ideally distinct, although in clinical and even neuropathologic practice substantial overlap exists. Neurodegenerative diseases are often categorized by whether they initially affect cognition, movement, strength, coordination, sensation, or autonomic control.

For example, neurodegenerative diseases such as Alzheimer's disease (AD), Parkinson's disease (PD), Huntington's disease (HD), amyotrophic lateral sclerosis (ALS) and prion diseases are characterized by neural deposits of misfolded aggregated protein.

Non-limiting examples of diseases and/or conditions characterized by proteinopathy-induced neurodegeneration comprise Amyotrophic lateral sclerosis (ALS), Parkinson's disease (PD), Huntington's disease (HD), Alzheimer's disease (AD), Creutzfeldt-Jakob disease (CD), Ataxia Telangiectasia Friedreich's Ataxia, Multiple Sclerosis (MS), Prion diseases, Spinocerebellar Ataxia (SCA), Spinal Muscular Atrophy (SMA), Traumatic Brain Injury.

"Parkinson's disease" refers to any medical condition wherein an individual experiences one or more symptoms associated with Parkinson's disease, such as without limitation one or more of the following symptoms: rest tremor, cogwheel rigidity, bradykinesia, postural reflex impairment, good response to L-dopa treatment, the absence of prominent oculomotor palsy, cerebellar or pyramidal signs, amyotrophy, dyspraxia and/or dysphasia.

"Lewy body dementia" refers to a medical condition that causes changes in memory, thinking, movement and behavior. These changes typically involve difficulties in planning, making decisions, and understanding visual information (seeing and interpreting where objects are in space). They can also involve movement problems, i.e. tremor, slowness, stiffness, and walking/balance problems that are similar to those in Parkinson's disease. Visual hallucinations, fluctuations in attention and alertness; and changes in behavior, personality and mood (depression or anxiety) have also been described.

"Multi systems atrophy" is a medical condition that causes impairments to balance, difficulty with movement, poor coordination, bladder dysfunction, sleep disturbances, as well as poor blood pressure control.

"Amyotrophic lateral sclerosis" or "ALS" refers to a progressive neurodegenerative disease that affects upper motor neurons (motor neurons in the brain) and/or lower motor neurons (motor neurons in the spinal cord) and results in motor neuron death. The term "ALS" includes all of the classifications of ALS known in the art, including, but not limited to classical ALS (affecting both lower and upper motor neurons), Primary Lateral Sclerosis (PLS, affecting only the upper motor neurons), Progressive Bulbar Palsy (PBP or Bulbar Onset, a version of ALS that begins with difficulties swallowing, chewing and speaking), Progressive Muscular Atrophy (PMA, affecting only the lower motor neurons) and familial ALS (a genetic version of ALS).

"Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques (found primarily in the association cortex, limbic system and basal ganglia) and neurofibrillary tangles (found inside neurons throughout affected areas). The major constituent of these plaques is amyloid beta peptide (Aβ), which is the cleavage product of beta amyloid precursor protein (βAPP or APP). APP is a type I transmembrane glycoprotein that contains a large ectopic N-terminal domain, a transmembrane domain and a small cytoplasmic C-terminal tail. The tangles are formed by the microtubule-associated protein tau, which aggregates intracellularly into amyloid fibrils termed paired helical filaments (PHFs).

"Huntington's disease" refers to a fatal neurological disorder characterized clinically by symptoms such as involuntary movements, cognition Impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy.

"Multiple sclerosis" refers to an inflammatory and demyelinating degenerative disease of the human central nervous system (CNS).

"Dialysis-related amyloidosis" is a disease characterized by the accumulation and tissue deposition of amyloid fibrils containing beta2-microglobulin in the bone, periarticular structures, and viscera of patients with chronic kidney disease. Beta2-microglobulin is normally cleared by glomerular filtration in the kidney, with subsequent reabsorption and catabolism in proximal tubules. Clearance of beta2-microglobulin declines in patients with reduced kidney function or patients undergoing dialysis, which leads to plasma accumulation and slow tissue deposition.

"Creutzfeldt-Jakob disease" (CJD) refers to a degenerative, invariably fatal brain disorder. In the early stages of disease, people may have failing memory, behavioral changes, lack of coordination and visual disturbances. As the Illness progresses, mental deterioration becomes pronounced and involuntary movements, blindness, weakness of extremities, and coma may occur. Creutzfeldt-Jakob disease has sporadic, iatrogenic, and familial forms, and a variant of CJD (vCJD).

Prion diseases and disorders are a group of rapidly progressive and untreatable neurodegenerative syndromes, neuropathologically characterized by spongiform change, neuronal cell loss, gliosis, and brain accumulation of abnormal amyloid polypeptide.

Prion disease" refers to one of several rapidly progressive, fatal, and untreatable brain degenerative disorders. These can be considered to be transmissible spongiform encephalopathies (TSE), a group that includes, but without limitation: Creutzfeldt-Jakob disease (CJD), new variant CJD, Kuru, Gerstmann-Sträussler-Scheinker syndrome (GSS), fatal familial insomnia (FFI) in humans, scrapie in sheep and goats, spongiform encephalopathy in cattle (also known as "mad cow disease"), and chronic wasting disease in cervids.

Example of prion diseases of other species include classical bovine spongiform encephalopathy (BSE C-type), atypical forms of bovine spongiform encephalopathy (BSE L-type and BSE H-type), scrapie in sheep, goats and rodents, and chronic wasting disease of cervids. Chronic wasting disease (CWD) of captive and wild cervids (deer, elk, moose, reindeer, and other species) represents another example or an animal prion disease.

Prion diseases share an underlying molecular pathology that involves the conversion of the hosts' normal form of the prion protein, (e.g., $PrP^C$), to a misfolded, aggregated, infectious and pathological form (e.g., PrPs).

The term "$PrP^C$" refers to the native prion protein molecule, which is naturally and widely expressed within the body of the Mammalia. Its structure is highly conserved and is not associated with a disease state.

The term "$PrP^{Sc}$" refers to the conformationally altered form of the $PrP^C$ molecule that is thought to be infectious and is associated with TSE/prion diseases, including vCJD, CJD, kuru, fatal insomnia, GSS, scrapie, BSE, CWD, and other rare TSEs of captive and experimental animals. It has the same amino acid sequence as normal, cellular $PrP^C$, but has converted some of the α-helix to β-sheet and is associated with a disease state.

The term "PrP" refers to prion protein in general

The term "polynucleotide" or "nucleic acid sequence" or "nucleic acid molecule" refers to a DNA or RNA molecule in single or double stranded form. In one example, a polynucleotide comprises a DNA encoding a protein or protein fragment.

The terms "protein" or "polypeptide" are used interchangeably and refer to molecules consisting of a chain of amino acids, without reference to a specific mode of action, size, three-dimensional structure or origin.

The term "variant" refers to an amino acid sequence having conservative amino acid substitutions, non-conservative amino acid substitutions (i.e. a degenerate variant), or a peptide having 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the recited sequence. The term "conservatively modified variants" applies to both amino acid and nucleic acid sequences. With respect to particular nucleic acid sequences, a conservatively modified variant refers to those nucleic acids, which encode identical or conservatively modified variants of the amino acid sequences. Because of the degeneracy of the genetic code, a large number of functionally identical nucleic acids encode any given protein. For instance, the codons GCA, GCC, GCG and (3CU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Accordingly, each silent variation of a nucleic acid, which, encodes a polypeptide described herein is implicit in each described polypeptide sequence and is within the scope of the present invention.

With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, for example, 1, 2, 3, 4, 5, 7, or 10, or more alterations can be made. Conservatively modified variants typically provide similar biological activity as the unmodified polypeptide sequence from which they are derived. For example, generation of immune response, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids, which are well known in the art.

The term "percent sequence identity" or "homology" refers to the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or the like.

The isolated recombinant polypeptides described herein may be used as immunogenic compounds and/or compositions.

The term "Immunogenic" or "immunogenicity" relates to the ability of a substance to stimulate or elicit an immune response. Immunogenicity is measured, for example, by determining the presence of antibodies specific for the substance. The presence of antibodies is detected by methods known in the art, for example using an ELISA or HAI assay.

As used herein, "immunogenic polypeptide" refers to a polypeptide which comprises an allele-specific motif, an epitope or other sequence such that the polypeptide will bind an MHC molecule and induce an immune response, such as a cytotoxic T lymphocyte ("CTL") response, and/or a B cell response (for example, antibody production), and/or a T-helper lymphocyte response against the antigen from which the immunogenic polypeptide is derived. The term "antigen presentation" means the expression of antigen on the surface of a cell in association with major histocompatibility complex class I or class II molecules (MHC-1 or MHC-1I) of animals or with the HLA-I and HLA-II of humans.

An "immunogenic composition" refers to a composition comprising an immunogenic polypeptide, or a nucleic acid molecule or vector encoding an immunogenic polypeptide that Induces a measurable CTL response against the Immunogenic polypeptide, or induces a measurable B cell response (such as production of antibodies) against the immunogenic polypeptide. In some examples it may refer to isolated, nucleic acids encoding an antigen, such as a nucleic acid that can be used to express the antigen (and thus be used to elicit an immune response against the polypeptide). For in vitro use, an immunogenic composition may comprise or consist of the isolated polypeptide or polynucleotide molecule encoding the polypeptide. For in vivo use, the immunogenic composition will typically include the polypeptide or polynucleotide molecule in a pharmaceutically acceptable carrier and may also include other agents, such as an adjuvant.

An "isolated" biological component, such as a polypeptide or polynucleotide may been substantially separated or purified away from other biological components, such as other biological components in which the component naturally occurs, such as other chromosomal and extrachromosomal DNA, RNA, and proteins. Proteins, peptides and nucleic acids that have been "Isolated" Include proteins purified by standard purification methods. The term also encompassed proteins or peptides prepared by recombinant expression in a host cell as well as chemically synthesized proteins, peptides and nucleic acid molecules. Isolated does not require absolute purity, and can include protein, peptide, or nucleic acid molecules that are at least 50% pure, such as at least 75%, 80%, 90%, 95%, 98%, 99%, or even 99.9% purity.

The term "antibody" refers to an immunoglobulin, antigen-binding fragment, or derivative thereof, which specifically binds and recognizes an analyte (antigen), an antigenic fragment thereof, or a dimer or multimer of the antigen. The term "antibody" is used herein in the broadest sense and encompasses various antibody structures, including but not limited to monoclonal antibodies, polyclonal antibodies, multi-specific antibodies (e.g., bi-specific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')2; diabodies; linear antibodies; single-chain antibody molecules (e.g. scFv); and multi-specific antibodies formed from antibody fragments. Antibody fragments include antigen binding fragment either produced by the modification of whole antibodies or those synthesized de novo using recombinant DNA methodologies.

The term "monoclonal antibody" refers to an antibody produced by a single clone of β-lymphocytes or by a cell into which nucleic acid encoding the light and heavy chains of a single antibody have been transfected, or a progeny thereof. Monoclonal antibodies are produced by methods known to those of skill in the art, for Instance by making hybrid antibody-forming cells from a fusion of myeloma cells with immune spleen cells. These fused cells and their progeny are termed "hybridomas." In some examples monoclonal antibodies are isolated from a subject. Monoclonal antibodies can have conservative amino acid substitutions which have substantially no effect on antigen binding or other immunoglobulin functions.

The term "antigen" refers to a compound, composition or substance that can stimulate the production of antibodies or a T cell response in an animal, including compositions that are Injected or absorbed into an animal. An antigen reacts with the products of specific humoral or cellular immunity, including those induced by heterologous or synthesized antigens, such as the disclosed herein. An antigen can Include one or more epitopes.

A "neutralizing antibody" refers to an antibody which reduces the infectious titer of an infectious agent by binding to a specific antigen on the infectious agent. In some examples the infectious agent is a virus. In some examples, an antibody that is specific for HA and neutralizes the infectious titer of influenza virus. A "broadly neutralizing antibody" is an antibody that binds to and Inhibits the function of related antigens, such as antigens that share at least 65%, 75%, 85%, 90%, 95%, 96%, 97%, 98% or 99% identity antigenic surface of antigen. With regard to an antigen from a pathogen, such as a virus, the antibody can bind to and inhibit the function of an antigen from more than one class and/or subclass of the pathogen.

The term "epitope" refers to an antigenic determinant. These are particular chemical groups or peptide sequences on a molecule that are antigenic, such that they elicit a specific immune response, for example, an epitope is the region of an antigen to which B and/or T cells respond.

A "chimeric polynucleotide" or "recombinant polynucleotide" refers to a polynucleotide which is not normally found in nature in a species A "nucleic acid construct" or "vector" refers to a polynucleotide molecule can be used to deliver exogenous DNA into a host cell. Vectors can comprise further genetic elements to facilitate their use in molecular cloning, such as e.g. selectable markers, multiple cloning sites and the like.

The term "introducing" as used herein in the context of a cell or organism refers to presenting the nucleic acid molecule to the organism and/or cell in such a manner that the nucleic acid molecule gains access to the interior of a cell. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into cells in a single transformation event or in separate transformation events.

Thus, the term "transformation" as used herein refers to the introduction of a heterologous nucleic acid into a cell. Transformation of a cell may be stable or transient.

The term "transient transformation" as used herein in the context of a polynucleotide refers to a polynucleotide that may be introduced into the cell and does not Integrate into the genome of the cell.

The term "stably introducing" or "stably introduced" as used herein in the context of a polynucleotide introduced into a cell refers to a polynucleotide that may be stably Incorporated into the genome of the cell, and thus the cell is stably transformed with the polynucleotide.

As used herein, the terms "contacting" refers to a process by which, for example, a compound may be delivered to a cell. The compound may be administered in a number of ways, including, but not limited to, direct introduction into a cell (i.e., intracellularly) and/or extracellular Introduction into a cavity, Interstitial space, or into the circulation of the organism.

A "cell" or "host cell" refers to an individual cell or cell culture that can be or has been a recipient of any recombinant vector(s), isolated polynucleotide, or polypeptide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the Invention. A host cell which comprises a recombinant vector of the invention is a recombinant host cell.

The term "subject", as used herein, refers to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

The term "treatment", "treat", or "treating" as used herein, refers to obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment.

The term "amelioration" or "ameliorates" as used herein refers to a decrease, reduction or elimination of a condition, disease, disorder, or phenotype, including an abnormality or symptom.

The term "symptom" of a disease or disorder (e.g., cancers) is any morbid phenomenon or departure from the normal in structure, function, or sensation, experienced by a subject and Indicative of disease.

A "treatment regimen" as used herein refers to a combination of dosage, frequency of administration, or duration of treatment, with or without addition of a second medication.

For example, a subject with cancer can be treated to prevent progression or alternatively a subject in remission can be treated with a compound or composition described herein to prevent recurrence.

In another example, a subject with a cancer can be treated to provide cellular or biological responses, a complete response, a partial response, a stable disease (without progression or relapse), or a response with a later relapse of the patient from or as a result of the treatment.

As used herein, the term "therapeutically effective amount" refers to an amount that is effective for preventing, ameliorating, or treating a disease or disorder.

As used herein, "adjuvant" means a vehicle used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages).

As used herein, the term "administration" refers to the introduction of a composition into a subject by a chosen route. Administration can be local or systemic. For example, if the chosen route is intravenous, the composition (such as a composition including a disclosed immunogen) is administered by introducing the composition into a vein of the subject. Exemplary routes of administration Include, but are not limited to, oral, injection (such as subcutaneous, intramuscullar, intradermal, intraperitoneal, and intravenous), sublingual, rectal, transdermal (for example, topical), intranasal, vaginal, and inhalation routes.

A compound or composition may be administered alone or in combination with other treatments, either simultaneously or sequentially, dependent upon the condition to be treated.

Compounds and/or compositions comprising compounds disclosed herein may be used in the methods described herein in combination with additional/alternate treatments or treatment regimes, as would be known to the skilled worker.

Method of the invention are conveniently practiced by providing the compounds and/or compositions used in such method in the form of a kit. Such kit preferably contains the composition. Such a kit preferably contains instructions for the use thereof.

To gain a better understanding of the invention described herein, the following examples are set forth. It should be understood that these examples are for Illustrative purposes only. Therefore, they should not limit the scope of this Invention in anyway.

Examples

The Structure of PrP$^{Sc}$:

Here, we provide a short overview on what is known about the structure of PrP$^{Sc}$, its proteolytically truncated variant (PrP 27-30), and related molecular species, for more detailed information see (Wile & Requena, 2018). Fourier-transform infrared (FTIR) spectroscopy provided the first experimental evidence that the N-terminally truncated PrP 27-30 contains predominantly β-structure (Caughey et al., 1991; Pan et al., 1993). Electron crystallography analyses on 2D crystals of PrP 27-30 and an engineered variant of only 106 residues, PrP$^{Sc}$106, suggested the presence of a β-solenoid fold as a key feature of the Infectious conformer (Wile et al., 2002; Govaerts et al., 2004). Subsequently, X-ray fiber diffraction determined the molecular height of PrP 27-30 in amyloid fibrils to be 19.2 Å, corresponding to the height of 4 β-strands (19.2 Å=4×4.8 Å) (Wile et al., 2009). In addition, the diffraction data confirmed that the core of PrP 27-30 adopts a β-solenoid fold, consisting of 4-stacked β-rungs. The repeating unit size of 19.2 Å was also found in the diffraction patterns that were obtained from PrPSc106 amyloid fibrils (Wan et al., 2015). Recently, cryo-EM and subsequent three-dimensional (3D) reconstructions demonstrated that PrP 27-30 amyloid fibrils can be formed by two Intertwined protofilaments. Furthermore, the cryo-EM analysis corroborated that the structure of PrP 27-30 consists of a 4-rung β-solenoid (Vázquez-Fernández et al., 2016).

PrP$^{Sc}$ has a β-sheet core that is assumed to be water-inaccessible with individual β-strands that are connected by short turns and loops (Smirnovas at al., 2011), although it is still unknown which residues are in each β-strand and which ones are facing outward or Inward with respect to the β-solenoid core (Silva et al., 2015; Wile & Requena, 2018). A proposed model, based on mass spectrometry of proteinase K-resistant fragments obtained from PrP 27-30, suggested which amino acids may be located in β-strands or connecting loops (Vázquez-Fernández et al., 2012; Silva et al., 2015). By combining experimental data and computational techniques the first physically-plausible, atomic resolution model of PrP$^{Sc}$ based on a four-rung beta-solenoid architecture was built (Spagnolli et al., 2018). The structure of PrP$^{Sc}$ has a high degree of stability, which provides resistance against denaturation and decontamination, but not all of the factors contributing to this stability are fully understood. It is clear that the highly-ordered hydrogen bonds that run up and down the β-sheets are essential for the structure and stability of the PrP$^{Sc}$ β-solenoid fold (Smirnovas et al., 2011). However, van-der-Waals forces, hydrophobic and electrostatic Interactions, as well as aromatic side-chain stacking also contribute to its stability, as it has been demonstrated in other amyloids (Tsemekhman et al., 2007) and β-solenoid proteins (Kobe & Kajava, 2000).

The Structure of the HET-s Prion Domain:

HET-s is a known functional prion of the filamentous fungus Podospora anserina and it is involved in regulating heterokaryon incompatibility among different mating types (Coustou et al., 1997; Wickner, 1997). The prion domain of HET-s (HET-s(218-289)) Is able to form amyloid fibrils and it becomes protease resistant in the process (Dos Reis et al., 2002). Its structure, which has been solved by ssNMR, consists of a left-handed, 2-rung β-solenoid (FIG. 1B) (Wasmer et al., 2008; van Melckebeke et al., 2010). The β-solenoid rungs are connected by a flexible loop of 15 residues (Ritter et al., 2005). There are eight β-strands per molecule, and each β-solenoid rung has four β-strands connected by short loops. The first two β-strands are connected by a short, 2-residue s-arc, changing the orientation of the peptide backbone by ~90°; the second and third n-strands are connected by a 3-residue β-arc, changing the orientation by ~150°, and, lastly, the third and fourth β-strands are connected by a single glycine residue (Wasmer et al., 2008).

HET-s(218-289) has a triangular hydrophobic core formed by the first three β-strands of each β-solenoid rung, which also includes two buried polar amino acids (T233 and S273) and two asparagine ladders consisting of N226/N262 and N243/N279 (Wasmer et al., 2008). The fourth β-strand is pointing away from the β-solenoid core, forming part of the loop that connects the first and the second rungs of the β-solenoid structure. The β-strands of the second β-solenoid rung stack on top of the β-strands of the first rung, forming four Intramolecular β-sheets. These β-sheets can connect with the β-strands of the next HET-s(218-289) molecule through intermolecular hydrogen bonds/β-sheet contacts (Wasmer et al., 2008). HET-s(218-289) contains polar and charged amino acids that are exposed on the surface of the β-solenoid structure, where three salt bridges are formed between the residues K229, E234 and R236 from the first-rung and the residues E265, K270, and E272 from the second β-rung (van Melckebeke et al., 2010). The HET-s (1-227) N-terminal domain consists of nine α-helices and two short β-strands (Balguerie et al., 2003; Greenwald et al., 2010). Overall, HET-s(218-289) has an amino acid composition that is very different to the yeast prions which are Q/N rich (Liebman & Chernoff, 2012).

In addition to the characterization via ssNMR, HET-s (218-289) has also been analyzed by cryo-EM (Mizuno et al., 2011) and X-ray fiber diffraction (Wan et al., 2012; Wan & Stubbs, 2014). In the latter studies, meridional reflections at ~4.8 Å and ~9.6 Å confirmed that HET-s(218-289) adopts a 2-rung A-solenoid structure with clear similarities to the structure of PrPSc (Wille et al., 2009; Wan et al., 2012).

The Characterization of the β-Solenoid Fold in General:

A-solenoid proteins are characterized by a polypeptide chain that folds into more or less regular "solenoidal windings", while the canonical β-helical proteins follow a more stringent helical geometry (Kajava & Steven, 2006a). β-solenoid proteins contain between three to well above 100 β-rungs (Kajava & Steven, 2006b). Each β-rung contains two to four β-strands and they are connected by tight turns, β-arcs (two to six residues), or longer loops. Overall, the β-rungs have a length between 12 and 30 amino acids. A β-rung corresponds to a complete turn of the amino acid backbone to where the next β-rung begins with an axial rise of 4.8±0.2 Å (Kajava & Steven, 2006a; Kajava et al., 2010). The β-rungs that form the β-solenoid structure are connected by hydrogen bonds to the β-rungs above and below, forming a hydrophobic core with solvent-exposed side-chains on the surface (Kajava & Steven, 2006a; Hennetin et al., 2006). A distinctive feature of β-solenoid proteins is the stacking of identical residues on the same position in subsequent β-rungs (Jenkins & Pickersgill, 2001; Kajava & Steven, 2006a). Such "ladders" are usually comprised of polar residues, with asparagine being the most commonly followed by serine and threonine, but aromatic residues can also form separate ladders that are stabilized by aromatic stacking (Yoder et al., 1993; Henrissat et al., 1995; Kajava & Steven, 2006a; Hennetin et al., 2006).

β-solenoid proteins can be classified into right- or left-handed polymers, depending on the direction in which the polypeptide chain winds around the axis (Kobe & Kajava, 2000). In addition, β-solenoid proteins can display a twist, which is determined by an angular offset between individual β-rungs (Yoder et al., 1993; Kobe & Kajava, 2000. The shape of a β-solenoid cross-section is defined by the β-arcs connecting each β-strand, with the most frequent shapes being generally triangular, rectangular, or oval (Kajava & Steven, 2006a). The short β-arcs that connect individual β-strands are mainly formed by non-polar and uncharged polar residues (Kajava et al., 2010), but longer loops can also connect subsequent β-rungs, while retaining the overall shape of the β-solenoid. Lastly, the N- and C-termini of β-solenoid proteins generally have polymerization-inhibiting caps, which contain polar and charged amino acids and protect the hydrophobic core from solvent exposure (Bryan et al., 2011; Kondo et al., 2012).

The β-arcs that connect the individual β-strands in a β-helix or β-solenoid structure (Kajava et al., 2010) are structurally similar to the more conventional β-turns, which traditionally contain four amino acids and result in a 180° turn of the peptide chain. The n-arcs in the HET-s(218-289) prion domain and other f-solenoid proteins often contain only one to three amino acids and effect turns by 90° to 150° (Wasmer et al., 2008). The structural constraints of these turns have been described in great detail and the bonding angle and distances are well characterized (Iengar et al., 2006; de Brevern, 2016).

Structure-Based, Rationally Designed Vaccine Candidates for Protein Folding Diseases:

Described herein is a vaccine or antigen (in one example a prophylactic vaccine) targeting the misfolded protein conformation that is responsible for diseases such as the prion diseases, Alzheimer's and Parkinson's disease, as well as related diseases requires antigens that adopt a disease-relevant conformation. To date, none of the vaccine candidates under study have been designed to use structure-based, rationally designed epitopes to elicit immune responses specific for the disease-causing protein conformation.

Vaccine Candidates Targeting the Infectious Prion Protein of Chronic Wasting Disease and Other Prion Diseases:

Chronic Wasting Disease (CWD) prions are spreading among cervids by an oral Infection route, other prion diseases also have demonstrated oral Infections as well established routes of infection. This peripheral infection mode opens CWD the other prion diseases to a potential intervention through vaccination (Hedlin et al., 2012; Mabbott, 2015). The development of CWD vaccines has been attempted in a large number of studies that relied on recombinant or chemically synthesized forms of PrP. Since the cellular prion protein (PrP$^C$) is present throughout the nervous system, it was difficult to obtain a good immune response against this self-antigen. Moreover, since these vaccine candidates were based on short peptides or non-infectious forms of the prion protein, they provided limited protection against CWD at best (Pilon et al., 2013; Goñi et al., 2015; Thuermer, 2015). By using the insights we gained on the structure of PrP$^{Sc}$ (Wille & Requena, 2018), we translated our knowledge into more specific vaccine candidates capable of providing better protection against CWD prions.

Since the structure of PrP$^{Sc}$ is based on a β-solenoid structure, we used proteins that natively adopt a β-solenoid fold, such as Het-s, antifreeze protein, HMW adhesin, endopolygalacturonase, and constructs derived thereof. The proteins of choice have no sequence homology or evolutionary relationship to PrP, which means that they are not infectious (despite having a β-solenoid structure) nor do they act as self-antigens in mammals. The α-solenoid structures come in left- and right-handed varieties, which also applies to the structure of PrP$^{Sc}$. At the moment, we are not certain if the structure of PrP$^{Sc}$ is based on a left- or right-handed fold. Therefore, we used both left- and right-handed scaffold proteins to design our vaccine candidates. Based on its beneficial properties, we have created a left-handed four-rung β-solenoid variant of the fungal Het-s protein (termed "Het-2s") and three new right-handed, four-rung β-solenoids (termed "3P4G-Vac, 2ODL-Vac, 1HG8-Vac"), established a recombinant expression and purification system, and verified their ability to fold into it a β-solenoidal structure.

For both the left- and right-handed β-solenoid constructs, we retained residues that project their side chains into the interior of the β-solenoid fold, since they are essential to stabilize the core of the β-solenoid structure. Residues that project their side chains out to the exterior can be changed more freely, since their effects on the stability of the β-solenoid fold are limited (Choi et al., 2008 & 2009; Daskalov et al., 2014; Wan & Stubbs, 2014). Incidentally, these exterior facing residues are also the ones that determine the antigenic profile of these molecules, as they constitute the surface that is recognized by the immune system. Therefore, we targeted/mutated only every second residue within the β-strands that constitute one surface of the β-solenoid fold. The corners of the β-solenoid fold are defined as β-arks comprising one to three amino acids (lengar et al., 2006; Wasmer et al., 2008; de Brevern, 2016) or longer loops that can accommodate sequence stretches that cannot form proper β-strands (Choi et al., 2008 & 2009). These β-arks and loops have been observed for both the left- and right-handed β-solenoid folds (Choi et al., 2008 & 2009), and are assumed to also extend to PrP$^{Sc}$ (Silva et al., 2015; Spagnolli et al., 2018). Therefore, we were able to insert PrP-based sequence motives in these corners (β-arks) adjacent to the targeted β-strands more freely, increasing the likelihood to create a sufficiently large, PrP$^{Sc}$-specific epitope/surface in the targeted scaffold molecules.

The changes necessary to create vaccine candidates required many simultaneous changes to the sequence of the scaffold proteins. The most economical method to accomplish these wholesale changes was by exchanging gene fragments to modify Individual β-strands and the adjacent corners or β-arks (as necessary). By using, for example, gBlocks (integrated DNA Technologies, Inc.; IDT) or synthetic genes (Bio Basic Inc.) it was straightforward to effect those changes in the sequences of the scaffold proteins. The modular assembly of the β-solenoid proteins allowed us to create permutations between different rung designs, which will speed up the process of constructing Individual vaccine candidates.

For each of these constructs, we expressed the protein in *E. coli* and purified the recombinant protein in its denatured or native state based on a His-tag located at the N- or C-terminus. The pure protein was refolded in vitro, which induced fibril formation. The fibrillization was checked by negative stain electron microscopy and the presence of ample amyloid fibrils indicated a successful refolding. Only vaccine candidates that were able to fibrillize in vitro were screened in Prnp$^{-/-}$ and wild-type mice, since only these constructs were able to adopt their designated fold and exposed the newly created epitopes/surface mimics as designed. Constructs based on PL3 were screened in Prnp$^{-/-}$ and wild-type mice when their structure adopted the native structure as detected by circular dichroism.

Vaccine Candidates Targeting Disease-Causing Protein Conformers for Other Neurodegenerative Diseases:

Recent insights into the structures of pathogenic amyloids that are known to cause diseases such as Alzheimer's and Parkinson's disease (e.g. A8(1-42) fibrils, tau PHFs, and α-synuclein fibrils), which have been recently solved by solid-state NMR spectroscopy (ssNMR) (Tuttle et al., 2016;) and cryo-EM (Wäiti et al., 2016; Fitzpatrick et al., 2017; Gremer et al., 2017; Guerrero-Ferreira et al., 2018; Li et al., 2018a; Li et al., 2018b)), provide novel targets for the development of structure-based, rationally designed vaccine candidates. These high-resolution structures in-register parallel help to define specific surface epitopes of the disease-causing/disease-related conformers. The approach that was devised to develop vaccine candidates to target PrP$^{Sc}$ (see above) was also employed to create vaccine candidates to mimic the disease-causing conformers of these other proteins.

Rational Design of β-Soienoid-Structured Scaffold Proteins as Innocuous Carriers for Disease-Specific Epitopes:

Proteins that have a natural tendency to fibrillize into amyloid fibrils, such as the fungal HET-s(218-289) prion domain, are easy to use as epitope carriers. No further modifications are needed to induce fibrillization as this protein/protein domain is prone to adopt a polymeric structure when in the β-solenoid state. Individual and discontinuous amino acid changes can be made to convert surface-facing residues into a mimic for disease-specific states of other proteins. The β-solenoid fold accepts many amino acid substitutions, as long as a general charge balance and steric compatibility is maintained. No changes are necessary for residues that face the interior of the β-solenoid fold, as these residues will not be visible to the immune system when a properly folded antigen is used. Moreover, these residues, which are predominantly hydrophobic in nature, are necessary to maintain the stability of the β-solenoid fold. Maintaining the proper β-solenoid structure is a prerequisite to achieving structure-specificity of the antigen.

A-solenoid-structured proteins that do not form amyloid fibrils under normal conditions can be modified to polymerize into this quaternary structure through a series of targeted amino acid changes (Peralta et al., 2015). The easiest approach is to select several β-solenoid rungs (a minimum of two is needed) from a β-solenoid-structured protein and add structurally targeted salt bridges near the N- and C-termini that induce directed attractions between individual protein molecules. It is advisable to select complete β-solenoid rungs to facilitate the face-to-face stacking of the Individual protein monomers. Direct stacking of the protein molecules will then allow inter-molecular hydrogen-bond formation between adjacent β-strands, thereby stabilizing a continuous β-solenoid structure along the fibril axis (Peralta et al., 2015). Once the formation of amyloid fibrils has been proven, for example through negative stain electron microscopy, it is straightforward to introduce the desired surface residues as described above.

Materials & Methods:

Construction of a Four-Rung, Left-Handed β-Solenoid Vaccine Scaffold-HET-2s:

The base protein used to construct HET-2s is the fungal prion protein HET-s from the filamentous fungus *Podospora anserina*. A linker sequence consisting of 12 glycines and 2 alanines was used to connect two copies of amino acid residues 218-289 of HET-s, resulting in a left-handed, four-rung β-solenoid protein scaffold. The length of the linker sequence may be variable, but preferably 10-16 amino acids in length. The amino acid sequence was codon optimized for recombinant *Escherichia coli* (*E. coli*) protein expression, the necessary gene fragments ordered as g-Blocks (IDT, Coramile, IA) and amplified via PCR before being cloned into a pET-17b vector (EMD Millipore, Billerica, MA) via NotI/XhoI restriction sites. The resulting DNA sequence was verified via Sanger sequencing (University of Alberta, Molecular Biology Service Unit). Scaffold proteins range in molecular mass between ~16.3 and ~15.9 kDa.

Construction of a Four-Rung, Right-Handed β-Solenoid Vaccine Scaffold β-Solenoid Proteins:

All constructs to create a four-rung, right-handed β-solenoid protein scaffold were designed using the UCSF ChimeraX software and any existing capping motifs were predicted using the RaptorX software (Bryan et al., 2011; Peng and Xu, 2011) to enhance the formation of aggregates (Bryan et al., 2011). A four-rung β-solenoid portion of six different proteins was selected (pentapeptide repeat protein AlbG, pectate lyase 3, cytoskeletal bactofilin BacA, $Ca^{2+}$-dependent beta-helical antifreeze protein, HMW adhesin, Poly(beta-D-mannuronate) C5 epimerase 4, and endopolygalacturonase). Afterwards, point mutations were introduced in order to form salt bridges to stabilize the interface between protein monomers and between the N- and C-termini of monomers. A Tobacco Etch Virus (TEV) cleavage site was introduced after the 6×His-tag to facilitate its removal and to enable the formation of a salt bridge between the N- and C-termini. The coding sequences were optimized for their expression in *E. coli*, and BamHI/HindIII restriction sites were used for cloning into pET-28b(+) expression vectors (Novagen, Germany) and NdeI/BamHI restriction sites were used for cloning into pET-21a(+) expression vectors (Novagen, Germany). Of these six chosen proteins, three were able to form amyloid fibrils in vitro (Ca2+-dependent beta-helical antifreeze protein, HMW adhesin, and endopolygalacturonase), thus providing us with three different four-rung, right-handed β-solenoid vaccine scaffolds (3P4G-Vac, 2ODL-Vac, and 1HG8-Vac) as the basis to develop structure-based vaccines as demonstrated with 3P4G-C7.

Consruction of β-Solenoid Vaccine Scaffolds 3P4G-Vac, 2ODL-Vac, and 1HG8-Vac

Using the UCSF ChimeraX software four rungs of the β-solenoid structure from the antifreeze protein from Antarctic bacterium, *Marinomonas primoryensis* (PDB #: 3P4G) were selected. An extended loop was removed to tighten up the folded protein and replaced with a short, three-amino acid flexible linker (SGA). Furthermore, two charged residues were inserted into the N-terminus and another charged residue was inserted into the C-terminus to create two salt bridges to induce polymerization of the resulting β-solenoid scaffold protein (Peralta et al., 2015). The resulting right-handed, β-solenoid vaccine scaffold was named 3P4G-Vac.

The same approach was used for the HMW1 secretion domain from *Haemophilus influenzae* (PDB #: 2ODL), except that two loop sequences were removed to create a tighter protein structure. Moreover, one charged residue was inserted at the N- and C-termini each to create two salt bridges. To prevent charge repulsion, one charged residue at the C-terminus was replaced with an uncharged amino acid. The resulting right-handed, β-solenoid vaccine scaffold was named 2ODL-Vac.

The endopolygalacturonase from the fungus *Fusarium moniliforme* (PDB #: 1HG8) was subjected to the same procedure, but only one charged residue needed to be added at the C-terminus to create a polymerization-competent β-solenoid protein. The resulting right-handed, β-solenoid vaccine scaffold was named 1HG8-Vac.

Construction of PrP-Directed Vaccine Candidates 14R1 Based on HET-28:

Vaccine candidates were designed for HET-2s with a 14 amino acid linker length connecting the two HET-s (218-289) prion domains, and codon optimized and constructed identically to the scaffold protein. HET-2s was drawn and visualized as a cartoon model, and alternating surface residues on β-strands β1b and β3b were chosen as targets to be modified. Residue placement was loosely based on a published threading for the structure of $PrP^{Sc}$ (Silva et al., 2015) and general β-sheet confirmation and stability (Jenkins & Pickersgill, 2001). Care was taken to ensure proper β-solenoid formation, resulting in the formation of salt bridges to ensure stability of the folded protein. The current vaccine candidate has a repetitive nature; i.e. rungs I & II are identical to III & IV, respectively, due to the previously mentioned salt bridge construction. Residues chosen were based on cervid PRNP sequences ranging from residues ~89-232.

Construction of PrP-Directed Vaccine Candidate 3P40-C7 Based on 3P4G:

Vaccine candidate 3P4G-C7 for PrP was designed based on one of the new four-rung β-solenoid scaffolds obtained from the Ca2+-dependent beta-helical antifreeze protein from *Marinomonas primoryensis*. The antifreeze protein (PDB access code: 3P4G) has several β-solenoid rungs, from which a portion containing a four-rung β-solenoid structure was selected and some residues were replaced in order to form two salt bridges to enable the protein to polymerize into amyloid fibrils. One salt bridge between the N- and C-termini to prompt the formation of amyloid fibrils, and the other in the first beta-solenoid rung to stabilize the fold. The exposed residues from deer PRNP sequence were selected at different regions and introduced in this 3P4G, four rung, right-handed β-solenoid scaffold protein. Once the residues were mutated and visualized using UCSF ChimeraX software, the coding sequence was optimized for *E. coli* expression and the synthetic gene was synthetized and cloned into pET-28a(+) expression vector (Novagen, Germany) using NcoI/HindIII restriction sites.

Construction of PrP-Directed Vaccine Candidates PL3C1, PL3C2 Based on PL3:

Vaccine candidates PL3C1 and PL3C2 for PrP were designed based on Pectate Lyase belonging to polysaccharide lyase family 3 (PL3) from *Caldicellulosiruptor bescii*. The PL3 protein (PDB access code: 4Z05) has seven, right-handed β-solenoid rungs, and while it does not form amyloid fibrils it has an atomic structure similar to $PrP^{Sc}$ based on the structural architecture of a β-solenoid protein.

In addition, the protein is soluble, which could be an advantage for the immunization process and for developing of antibodies with engineered antigens based on PL3. Similar to our approach to create vaccine candidates with fibrillar scaffold n-solenoid proteins, some residues from the PrP sequence were selected and introduced in regular, soluble PL3. Once the residues were mutated and visualized using UCSF ChimeraX software, the coding sequence was optimized for *E. coli* expression and the synthetic gene was synthetized and cloned into pET-28b(+) expression vector (Novagen, Germany) using NcoI/HindIII restriction sites.

Construction of Aβ-Directed Vaccine Candidates AβC3, AβC4 Based on HET-s:

Vaccine candidates for Aβ were designed based on the prion domain (residues 218-289) of the fungal prion protein HET-s from *Podospora anserine*. The HET-s structure was downloaded from the Protein Data Bank (PDB access code: 2RNM) and visualized in UCSF ChimeraX software, then taking into account the A8(1-42) fibril structure (PDB access code: 5OQV) solved by cryo-EM (Gremer et al., 2017). Surface exposed residues of Aβ(1-42) were placed into the HET-s structure in order to mimic an epitope which is usually 5-8 amino acids. It is important to mention that residues mutated in the first rung of HET-s were the same mutated in the second rung, this was done in order to mimic the Aβ(1-42) fibril structure which is a parallel in-register fold. Once the residues were mutated using UCSF ChimeraX software, the coding sequences were optimized for *E. coli* expression and the synthetic genes were synthetized and cloned into pET-21a(+) expression vector (Novagen, Germany) by NdeI/BamHI restriction sites.

Construction of α-Synuclein-Directed Vaccine Candidates α-S3, α-S6, α-S8, and α-S9 Based on HET-s:

α-synuclein-directed vaccine candidates were also designed on the basis of the HET-s prion domain (residues 218-289) (PDB access code: 2RNM). Surface exposed residues from the high-resolution structures of α-synuclein (PDB access code: 2N0 Å, 6CU7 and 6CU8) determined by ssNMR and X-ray fiber diffraction (Tuttle et al., 2016) were selected and placed into the HET-s(218-289) construct using UCSF ChimeraX software. In this design the residues mutated in the first rung were the same mutated in the second rung of HET-s, this was also in order to mimic the α-synuclein fibril structure that is parallel in-register. The coding sequence was optimized for *E. coli* expression and the synthetic gene was synthetized and cloned into pET-21a (+) expression vector (Novagen, Germany) by NdeI/BamHI restriction sites.

Construction of Tau-Directed Vaccine Candidate TauC3, TauC4 Based on HET-s:

The vaccine candidates targeting the tau protein were also based on the HET-s prion domain (residues 218-289) (PDB access code: 2RNM). Taking into account the tau paired helical filament structure (PDB access code: 5O3L) obtained by cryo-EM (Fitzpatrick et al., 2017), surface exposed residues were selected and placed into HET-s(218-289) construct using UCSF ChimeraX software, then the coding sequences were optimized for *E. coli* expression and the synthetic genes were synthetized and cloned into pET-21a (+) expression vector (Novagen, Germany) by restriction sites NdeI/BamHI. These constructs were also designed as a parallel in-register fold, therefore both rungs of HET-s were mutated identically to mimic the misfolded tau protein.

Expression and Purification of HET-2s, 14R1:

All HET-s-based constructs and vaccines candidates were purified identically. The purification protocol was adapted from (Wan, dissertation, 2014). Sequence verified plasmids were heat-shock transformed into BL21(DE3) chemically competent cells (Life Technologies, Carlsbad, CA) using ampicillin (Sigma-Aldrich, St. Louis, MO) (100 μg/mL) for antibiotic selection. Transformed cells were then grown in 300 mL ZYM-5052 autoinduction media (Teknova Inc, Hollister, CA) at 350 rpm in 2.8 L Fernbach flasks for roughly 24 hours at 37° C.

Following growth, the cells were pelleted by centrifugation at 5000×g for 15 minutes, then resuspended at 3 mL/g cell pellet in resuspension buffer (50 mM Tris-HCl pH 8.0, 100 mM NaCl, 0.1 mM PMSF, 5 mM EDTA). The mixture was then digested with 10 mg of recombinant human lysozyme (Lysobac, InVitria, Fort Collins, CO) per gram of pellet at room temperature while stirred for 20 minutes. The suspension is then sonicated on a Sonifier 250 (Branson Ultrasonics, Danbury, CT) at 5s on and 5s off cycles for 10 minutes at 80% output at 4° C., and then centrifuged at 6000×g and pelleted as described before. The pellet was then resuspended in wash buffer (50 mM Tris-HCl pH 80, 100 mM NaCl, 0.5% Trition-X100) and sonicated as previously described. Following sonication MgCl2 was added for a final concentration of 10 mM. The solution was then digested with lysozyme again, along with 500 U of benzonase (Sigma-Aldrich, St. Louis, MO), then pelleted and resuspended in resuspension buffer three more times. The inclusion bodies solution was then pelleted and stored at −20° C. until further purification.

Inclusion bodies were purified via a C-terminus 6x-histidine tag. Pelleted inclusion bodies were resuspended at 3 mL/g in denaturation buffer (20 mM Tris-HCl pH 8.0, 6M guanidium hydrochloride) and stirred for 30 minutes at room temperature, then ultracentrifuged at 50,000×g for 45 minutes at 4° C. The clarified solution was then purified using a Ni-nitrolotriacetic acid (NTA) column (QIAGEN, Venlo, Netherlands), binding proteins with a 6x-his tail. The column was equilibrated and washed with one and three bed volumes, respectively, of denaturation buffer and immobilized protein was eluted with elution buffer (50 mM citric acid pH 2.0, 6M guanididium hydrochloride). Eluted proteins were buffer exchanged into 500 mM acetic acid using Zeba spin desalting columns (Thermo Fisher Scientific, Waltham, MA). The desalted sample was then fibrillized by Increasing the pH to 7.5 using 3 M tris and stored at room temperature with 1 mM sodium azide.

Transformation, Expression and Purification of HET-s, AβC3, AβC4, TauC3, TauC4, α-SC3, α-SCO, α-SCS, α-SC9 and Four-Rung, Right-Handed β-Solenoid Scatfold Proteins, 20DL-Vac and 1HG8-Vac:

All vaccine candidate constructions and the scaffold construction were transformed, expressed and purified identically. Approximately ~100 ng of plasmid DNA were added to 50 μL of *E. coli* BL21(DE3) chemically competent cells (Life Technologies, Carlsbad, CA) and placed on ice for 20 min, then a heat shock at 42° C. for 30 seconds was performed and immediately the reaction was placed on ice for 2 minutes. Subsequently, 250 μL of Super Optimal broth with Catabolite repression (SOC) media was added and the cells were grown at 37° C. In agitation at 250 rpm for 60 min. 40 μL of the transformation was spread onto prewarmed plates containing 100 μg/mL ampicillin (Sigma-Aldrich, St. Louis, MO) as antibiotic selection and incubate at 37° C. overnight.

Colonies were picked and cultured in 5 mL of Luria-Bertani media containing 100 μg/mL ampicillin at 37° C., 250 rpm, overnight. Next day plasmid DNA was Isolated for each transformant colony using QIAprep Spin Miniprep Kit (QIAGEN, Venlo, Netherlands) as the manufacturer's instructions. Each plasmid DNA was sent for Sanger sequencing and the positive colonies were stored in 20% glycerol stock at −70° C. A small amount of the glycerol stock was scraped to pre-inoculate 25 mL of LB media at 37° C., 250 rpm, overnight, then a 2 L flask containing 500 mL of 2YT media (1.6% tryptone, 1.0% yeast extract and 0.5% NaCl, pH 7.0) was inoculated and incubated at 37° C. and 250 rpm until an optical density (OD) of 0.6-0.8 at 600 nm was reached. Then the culture was cooled down to 25° C., then it was induced for protein expression by adding Isopropyl β-D-1-thiogalactopyranoside to a final concentration of 1 mM and the culture was grown overnight.

Following induction, the cells were harvested at 11,000 rpm, 4° C. for 10 min, then they were frozen for at least 30 min and later the pellet was resuspended in 20 ml of IB buffer (100 mM Tris-HCl, pH 8.0, 0.5% Triton X-100), containing 1 mg/mL lysozyme and 1×EDTA-free protease inhibitor tablets. Pellet was homogenized and incubated at room temperature for 30 min and then it was sonicated for 7 cycles (1 minute on and 1 minute off), at output voltage 50 with a 50% duty cycle. Subsequently, 3 U/mL benzonase per each mL of the original culture were added and the homogenate was incubated for another 20 minutes, then it was centrifuged at 11,000 rpm, 4° C. for 30 min. The supernatant was discarded meanwhile the pellet was homogenized in IB buffer, containing 1 mg/mL lysozyme, and 1×protease Inhibitor tablet, then it was Incubated for 20 min at room temperature and the homogenate was sonicated for 5 cycles and centrifuged under the same conditions as described above. The resulting pellet was washed twice with IB buffer and centrifuged at 11,000 rpm, 4° C. for 30 min, and a final wash step using 100 mM Tris-HCl, pH8.0 buffer was performed. The pellet contained our inclusion bodies was stored at −20° C.

The inclusion bodies were solubilized by the addition of protein solubilization buffer (6M Guanidine hydrochloride, 20 mM sodium phosphate, 0.5 M NaCl and 10 mM Imidazole, pH 8.0) and stirred at room temperature for 45 min, subsequently it was clarified by ultracentrifugation at 45,000 rpm for 35 min at 4° C. The vaccine candidate proteins were then purified by using an biologic duoflow™ chromatography system (Bio-Rad Laboratories, Hercules, USA) enclosed in a 4° C. fridge as following: A HisTrap™ HP column (GE Healthcare Life Sciences, Piscataway, NJ, USA) was equilibrated using 30 ml of equilibrium buffer (8M Urea, 20 mM Sodium Phosphate, 0.5M NaCl, and 10 mM imidazole, pH 8.0) or until the absorbance at 280 nm achieved a stable baseline measurement, then the clarified lysate was loaded into the HisTrap™ HP column and the column was washed by 25 mL of equilibrium buffer, then Immediately other wash step was done with the equilibrium buffer but containing 20 mM imidazole, then a linear gradient from 20 mM to 500 mM imidazole (the other component was the same as the equilibrium buffer) was started to elute the bound candidate vaccine proteins. The peaks of candidate vaccines of interest were automatically collected through BioFrac™ Fraction Collector (Bio-Rad Laboratories, Hercules, USA) when the absorbance was above of 0.05 at 280 nm. Fractions containing our pure vaccine candidates' proteins were desalted using HiTrap® Desalting Columns (GE Healthcare Life Sciences, Piscataway, NJ, USA), firstly the column was equilibrated using 10 mL of 175 mM acetic acid, ~pH 2.8, then the fractions were loaded into HiTrap® desalting column and the protein was buffer-exchanged passing 20 mL of 175 mM acetic acid, ~pH 2.8. The peaks of candidate vaccines of Interest were automatically collected as mentioned above. Once the samples were desalted, the pH was increased to 7.5 by ~200 μL 3M Tris and sodium azide was added to a final concentration of 1 mM. They were placed at room temperature to prompt its fibrillation.

Transformation, Expression and Purification of Four-Rung Right-Handed β-Solenoid Vaccine Scaffold Protein 3P4G-Vac, and Vaccine Candidate 3P4G-VacC7:

The transformation and expression for four-rung, right-handed β-solenoid vaccine scaffold 3P4G-Vac and vaccine candidate 3P4G-C7 was conducted as described above at 25° C. using 100 μg/mL kanamycin.

Following induction, the cells were harvested at 11,000 rpm, 4° C. for 10 min, then they were frozen for at least 30 min and later the pellet was resuspended in 20 mL of resuspension buffer (50 mM Tris, 0.5M NaCl, pH 7.5, 2% (v/v) glycerol, 2 mM CaCl2 and 20 mM imidazole, pH 8.0) containing 0.5% Triton X-100, 1 mg/mL lysozyme and 1× EDTA-free protease inhibitor tablets. The pellet was homogenized and incubated at room temperature for 30 min and then it was sonicated for 7 cycles (1 minute on and 1 minute off), at output voltage 50 with a 50% duty cycle. Subsequently, 3 U/mL benzonase per ml of the original culture were added and the homogenate was incubated for another 20 minutes, then it was centrifuged at 11,000 rpm, 4° C. for 30 min. The supernatant was recovered and it was clarified by ultracentrifugation at 45,000 rpm for 30 min at 4° C. Then the protein was purified by using a biologic Duoflow™ chromatography system (Bio-Rad Laboratories, Hercules, USA) at 4° C. as follows: A HisTrap™ HP column (GE Healthcare Life Sciences, Piscataway, NJ, USA) was equilibrated using 30 ml of equilibrium buffer (50 mM Tris, 0.5M NaCl, pH 7.5, 2% (v/v) glycerol, 2 mM CaCl2) and 20 mM imidazole, pH 8.0) or until the absorbance at 280 nm achieved a stable baseline measurement, then the clarified lysate was loaded into the HisTrap™ HP column and the column was washed by 25 mL of equilibrium buffer, following by a linear gradient from 20 mM to 500 mM imidazole (the other component was the same as the equilibrium buffer) was started to elute the bound candidate vaccine protein. The peaks of interest protein were automatically collected through BioFrac™ Fraction Collector (Bio-Rad Laboratories, Hercules, USA) when the absorbance was above of 0.05 at 280 nm. Fractions containing the pure proteins were concentrated using an Amicon® Ultra-4 Centrifugal Filter Unit with a molecular weight cut-off of 3000 Da.

Then the concentrated fractions containing our pure proteins, four-rung, right-handed β-solenoid scaffold protein 3P4G-Vac and the vaccine candidate 3P4G-C7 were loaded into PD10 Desalting Columns (GE Healthcare Life Sciences, Piscataway, NJ, USA). First, the column was equilibrated using 25 mL of 100 mM Tris-HCl, 0.5 M NaCl, pH 7.4, then 2.5 mL of the protein concentrated was loaded into the desalting column, then 3P4G-Vac, and 3P4G-C7 were eluted using 3.5 mL of 100 mM Tris-HCl, 0.5 M NaCl, the first 0.5 mL were discarded and the proteins were collected in a total volume of 3 mL. Then sodium azide was added to a final concentration of 1 mM, and the pure proteins were placed at room temperature to prompt its fibrillation.

Transformation, Expression and Purification of PL3 and Vaccine Candidates PL3C1, PL3C2:

The scaffold protein PL3 and the vaccine candidates PL3C1 and PL3C2 were expressed in E. coli BL21(DE3). The cultures were incubated at 25° C. in 500 mL of 2YT media containing 0.1% glucose supplemented with 100 μg/mL kanamycin with continuous shaking at 250 rpm until the culture reached an absorbance at 600 nm of 0.6-0.8, then Isopropyl-s-d-thiogalactosidase was added to achieve a final concentration of 1 mM and culture was maintained under the same temperature and agitation conditions for 16 hours.

The cells were harvested at 11,000 rpm, 4° C. for 10 min and frozen for 30 min. The pellet of PL3, PL3C1, and PL3C2 was resuspended in 20 ml of resuspension buffer (100 mM Tris-HCl, 0.5 M NaCl, pH 7.4). Then Triton X-100 was added to reach 0.5% final concentration, as well as 1 mg/mL lysozyme and 1×EDTA-free protease Inhibitor tablets. The pellet was homogenized and incubated at room temperature for 30 min and then sonicated for 7 cycles (1 minute on and 1 minute off), at output voltage 50 with a 50% duty cycle. Subsequently, 3 U/mL benzonase per mL of the original culture were added and the homogenate was incubated for another 20 minutes, then it was centrifuged at 11,000 rpm, 4° C. for 30 min. The supernatant was recovered and clarified by ultracentrifugation at 45,000 rpm for 30 min at 4° C., then the protein was purified by using an biologic Duoflow™ chromatography system (Bio-Rad Laboratories, Hercules, USA) enclosed at 4° C. as follows: A HisTrap™ HP column (GE Healthcare Life Sciences, Piscataway, NJ, USA) was equilibrated using 30 mL of equilibrium buffer (100 mM Tris, 0.5 M NaCl, pH 8.0) or until the absorbance at 280 nm achieved a stable baseline measurement, then the clarified lysate was loaded into the HisTrap™ HP column and the column then was washed by 25 mL of equilibrium buffer, followed by a linear gradient from 0 mM to 500 mM imidazole (the other components were the same as the equilibrium buffer) was used to elute the bound vaccine candidate protein. The peaks of interest protein were automatically collected through a BioFrac™ Fraction Collector (Bio-Rad Laboratories, Hercules, USA) when the absorbance was above of 0.05 at 280 nm.

Fractions containing the pure proteins were concentrated using an Amicon® Ultra-4 Centrifugal Filter Unit with a molecular weight cut-off of 3000 Da. Once fractions were concentrated, then PL3, PL3C1, and PL3C2 were loaded into HiLoad Superdex 75 PG column (GE Healthcare Life Sciences, Piscataway, NJ, USA) previously equilibrated with 250 mL of size exclusion buffer (50 mM sodium phosphate, 150 mM NaCl, pH 7.4) in order to conduct a size exclusion molecular chromatography, then the protein was eluted by using 125 mL size exclusion chromatography buffer. The fractions containing the pure protein were automatically collected through BioFrac™ Fraction Collector (Bio-Rad Laboratories, Hercules, USA) when the absorbance was above of 0.05 at 280 nm. Then sodium azide was added to a final concentration of 1 mM and the samples stored at −20° C.

Quality Control Analyses (SDS PAGE, Negative Stain EM):

Purified samples were subject to both sodium dodecyl sulfate-polyacrylamide gel electrophoresis (SDS-PAGE) and negative staining transmission electron microscopy (TEM) to Insure purity and presence of fibrils. The protein concentration was determined by either bicinchoninic acid protein assay (BCA assay) (Thermo Fisher Scientific, Waltham, MA) or absorbance at 280 nm (A280) if the sample was Insoluble or soluble, respectively.

5× in house SDS sample buffer with β-mercaptoethanol is added to samples and boiled for 5 min at 95° C. Samples are then loaded on NuPAGE 12% Bis-Tris protein gels (Thermo Fisher Scientific, Waltham, MA) and electrophoresed at 200 V for 35 min. Gels are then washed and stained and visualized with Bio-safe Coomassie stain (Bio-Rad Laboratories, Hercules, CA).

To check fibril formation, purified samples were imaged and visualized via negative staining TEM. 200 or 400 square mesh carbon-coated copper grids (Electron Microscopy Sciences, Hatfield, PA) are glow discharged at 15 mA, 0.39 mBar for 1 min. 5 μL of ~1 mg/mL sample is absorbed onto the grid for 30 sec and then washed with 2 drops (50 μL) ammonium acetate (100 and 10 mM) and stained with 2 drops (50 μL) of 2% filtered uranyl acetate (Electron Microscopy Sciences, Hatfield, PA). Grids were then blotted dry with filter paper and stored at room temperature. Grids were visualized by a Tecnai F20 TEM (FEI Company, Hillsboro, OR) operating at 200 kV using a bottom-mounted Eagle 4k×4k charge-coupled device (CCD) camera (FEI Company, Hillsboro, OR).

Circular dichroism was performed just for vaccine candidates based on the soluble scaffold protein PL3 in order to determine if after mutations the protein secondary structure was not affected. The spectrum was a recorded from 200 nm to 300 nm for 0.5 mg/mL protein in 50 mM sodium phosphate, 150 mM NaCl, pH 7.4, using a 1 cm cell at room temperature. Spectra were collected at a scan rate proportional to high voltage using a Chirascan™ Circular Dichroism Spectrometer instrument.

Immunization of Indicator Mice With HET-2s, 14R1, AβC3, AβC4, TauC3, TauC4, α-SC3, α-SC6, α-SC8, α-SC9, PL3C1, and PL3C2:

For the animal tests, all experimental protocols were in accordance with the Canadian Council on Animal Care and were approved by the Animal Care and Use Committee at the University of Alberta (AUP00000424).

Vaccine candidates showing good fibrillization, and therefore adopting the proper β-solenoid fold, were used to immunize Prnp$^{-/-}$ and Prnp$^{+/+}$ (FVB wild-type) mice. Sample concentrations were determined as described previously and buffer exchanged into PBS pH 7.4, At day zero, mice between ~8-12 weeks of age of both genders were intraperitoneally (IP) inoculated with a priming dose of 100 μg of sonicated immunogen in 100 μL of inoculum of 50/50 Freund's complete adjuvant (FCA) (Sigma-Aldrich, St. Louis, MO). Subsequent biweekly boosters consisted of 50 μg immunogen in 100 μL of inoculum of 50/50 Freund's incomplete adjuvant (FIA) (Sigma-Aldrich, St. Louis, MO) IP Injected for a total of 3 boosters. Blood was drawn before the Immunizations started (pre-immune sera) and every two weeks after each boost, the post-immune sera were collected two weeks after the last boost. As a control, we intracranially (IC) inoculated 14R1 in FVB wild-type mice, to determine if the vaccine candidate could cause disease and it is currently ongoing.

Indirect and Competitive ELISAs for 14R1:

Indirect enzyme-linked immunosorbent assays (ELISAs) were used to determine titres of post-immune sera while competition ELISAs were used to determine specificity of post-immune sera to Infectious CWD brain homogenates. All steps were performed at room temperature unless otherwise specified. High-binding 96 well UltraCruz microplate strips (Santa Cruz Biotechnology Inc., Santa Cruz, CA) were coated with 0.5 μg of sonicated antigen in PBS and Incubated while rotating overnight. The plates were then blocked with 5% skim milk in TBST (0.1% tween 20) for 1 hour or overnight at 4° C. and washed with TBST. Post-immune sera were then serially diluted in PBS and incubated for 1 hour. For competition ELISAs, post-immune sera was added to CWD+ brain homogenates in non-binding microplates (Greiner Bio-One, Kremsmünster, Austria), Incubated for 1 hour, then transferred back to the original plates and Incubated for 1 hour. After washing with TBST, secondary HRP-goat anti-mouse at 1:5000 dilution in 5% skim milk TBS was added and incubated for 30 min and washed again afterwards. 3,3',5,5'-Tetramethylbenzidine (TMB) substrate (SurModics, Eden Prairie, MN) is added and incubated for 30 min in dark before addition of 2 M sulphuric acid to stop reaction. Absorbance at 450 nm is then read within 5 min.

Indirect ELISAs for AβC3, AβC4, TauC3, TauC4, α-SC3, α-SC6, α-SC8, α-SC9, P3C1, and PL3C2:

Indirect ELISAs were used to determine titers of pre- and post-Immune sera of mice immunized with the engineered protein antigens. All antigens were diluted in PBS to reach a concentration of 5 mg/mL and sonicated for 10 seconds at minimum output voltage, while PL3C1 and PL3C2 were not sonicated since they are soluble proteins. High-binding 96 well UltraCruz microplate strips (Santa Cruz Biotechnology Inc., Santa Cruz, CA) were coated with 0.5 μg of antigen by adding 100 μL of the antigen diluted at 5 mg/mL and the plates were incubated overnight in gentle agitation at 4° C. Then the plates were blocked with 3% BSA for 1 hour at room temperature and washed three times with PBS containing 0.1% tween 20, then immune sera were serially diluted in 1% BSA at different dilutions. Later, the antisera dilutions were added to the plate and incubated in the dark for 2 hours using gentle agitation. Subsequently, three more washes were performed as described previously. Then 100 μL of secondary HRP-goat anti-mouse at 1:5000 dilution in 5% skim milk in PBS were added to each well and incubated for 30 min and the plate was washed five times. 100 μL of 3,3',5,5'-Tetramethylbenzidine (TMB) substrate (SurModics, Eden Prairie, MN) was added in the dark until the color was developed then the reaction was stopped by addition of 2 M sulphuric acid. Absorbance at 450 nm was recorded.

Competitive ELISAs for α-SC3, α-SC6, α-SC8, α-SC9, U3C1, and PL3C2:

Competitive ELISAs were used to determine the specificity of polyclonal antibodies in post-immune sera to both prion-infected brain homogenates and alpha-synucleinopathy brain homogenates, respectively. High-binding 96 well UltraCruz microplate strips (Santa Cruz Biotechnology Inc., Santa Cruz, CA) were coated with 0.5 μg of sonicated antigen in PBS and incubated overnight at 4° C. with constant shaking. The plates were then blocked with 3% BSA for 1 hour at room temperature and washed three times with PBS containing 0.1% tween 20. Then 50 ug of total protein of brain homogenates from three different α-synucleinopathies (Lewy body dementia, Multiple system atrophy, Parkinson's disease) or any of the prion diseases were added to different wells and incubated using gentle agitation at room temperature for 5 minutes. Brain homogenates from healthy controls were added to different wells as negative controls. Then 50 μL of anti-serum at 1:10,000 to 1:500,000 dilution were added and the plates were incubated in the dark at room temperature for 1 hour using gentle agitation. Subsequently, the plates were washed as described above, then 100 μL of secondary HRP-goat anti-mouse at 1:5,000 dilution in 5% skim milk in PBS were added and incubated in the dark at room temperature using gentle agitation for 1 h. Finally, the plate was washed live times as mentioned above and 3,3',5,5'-Tetramethylbenzidine (TMB) substrate (SurModics, Eden Prairie, MN) was added for developing color. Once color was developed 50 μL of 2 M sulphuric acid was added to stop reaction. Absorbance at 450 nm was recorded within 5 min.

Table of Sequences

TABLE 1

Figure 3:
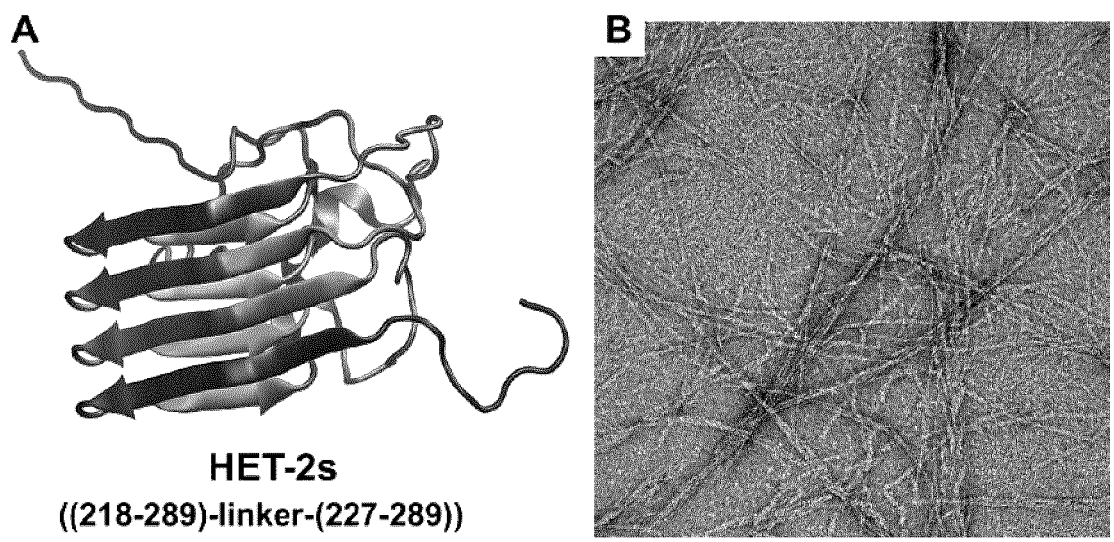
FIG. 3 Construction of a (HET-s)-based scaffold for the design of structure-based antigens/vaccine candidates. H structure of White-tailed deer PrP covering residues 128-228 (PDB access code 4yxh (Baral et al., 2015)) and was extended to include unfolded parts of the molecule that could not be crystallized (residues 93-127 and 229-233) through molecular dynamics simulations.
Figure 5:
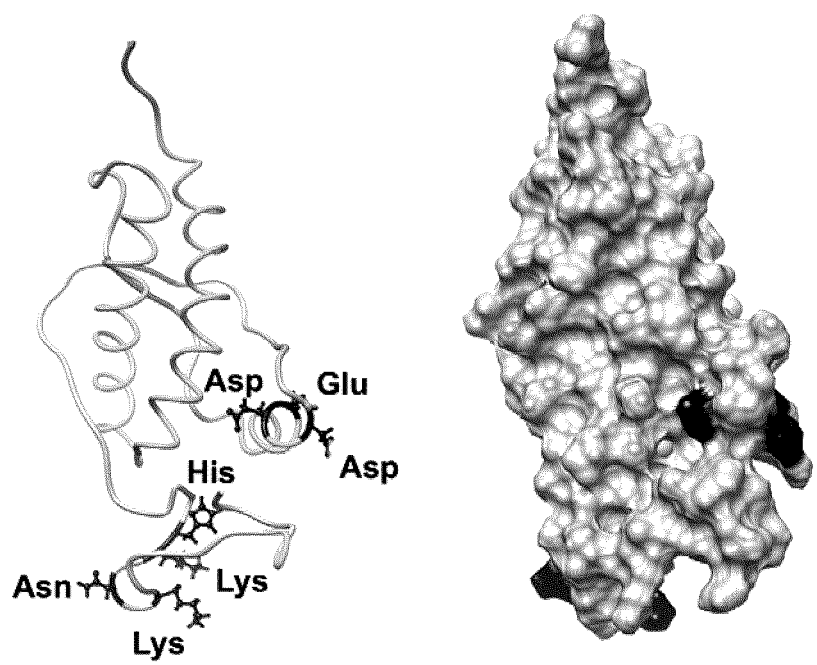
Figure 6:
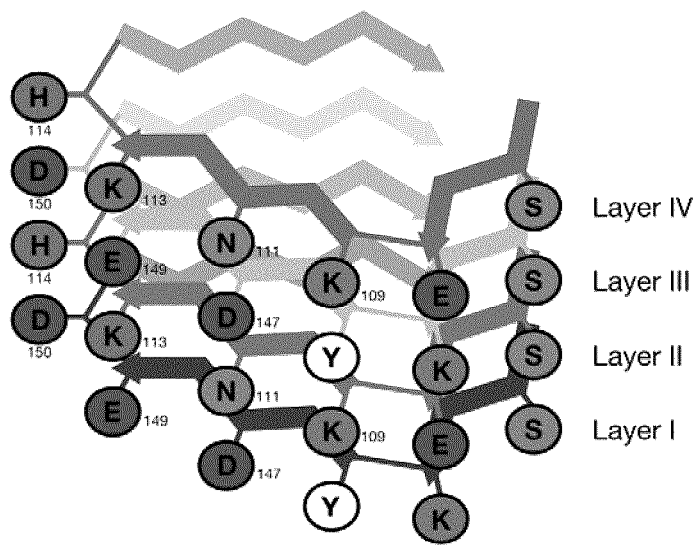
FIG. 6 Schematic of the first vaccine candidate (14R1) based on the HET-2s construct with select amino acids replaced with residues originating from White-tailed Deer PrP. The four beta-solenoid layers of HET-2s are shown as simple zigzag lines with outward facing residues represented in one-letter code (top). Amino acids that were replaced with the respective residues from PrP are labelled with the PrP-based amino acid numbering. The primary structure of HET-2s with residues originating from White-tailed Deer PrP indicated in a taller font (bottom).
Figure 7:
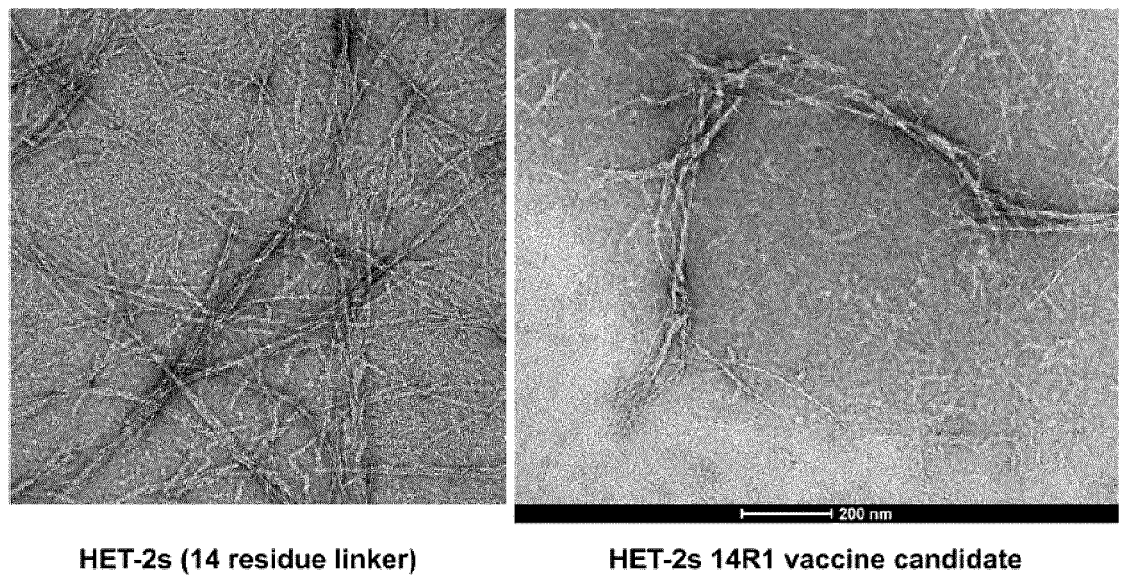
FIG. 7 Negative stain electron micrographs of unmodified HET-2s (left) and HET-2s 14R1 vaccine candidate (right). Both proteins were expressed in E. coli, purified using a C-terminal histidine tag, and fibrillized in vitro. The fact that HET-2s 14R1 forms amyloid fibrils indistinguishable from those of the unmodified HET-2s proves that the HET-2s 14R1 construct folds in a correct manner adopting a four-rung beta-solenoid fold. Fibrils from both constructs are Indistinguishable from those of unmodified HET-s(218-289) (Mizuno et al., 2011). The in vitro fibrillization serves as a quality control step, indicating that the modified residues in HET-2s 14R1 adopt a beta-strand configuration, as designed.
Figure 8:
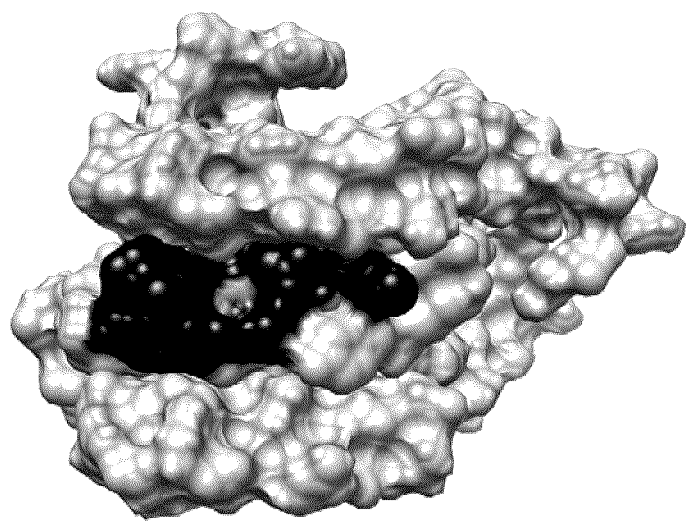
FIG. 8 Space filling representation of three HET-s molecules stacked vertically with the fibril axis running from top to bottom in the plane of the paper. The middle HET-s molecule is shown with the 14R1 amino acid modifications indicated in black. The top and bottom HET-s molecules are unchanged, representing the surface of the native HET-s (218-289) prion domain In the prion state. PDB access code: 2RNM, for the HET-s(218-289) structure (Wasmer et al., 2008).
Figure 10:
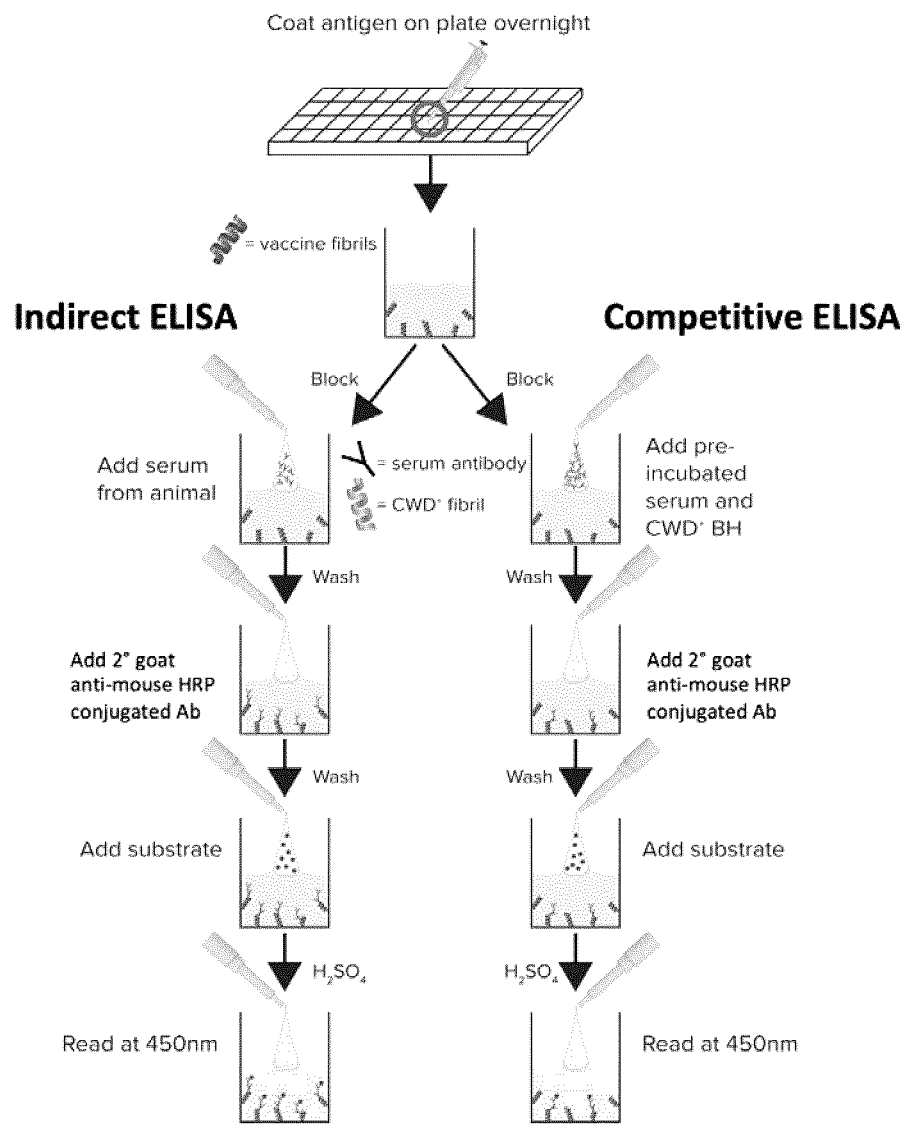
FIG. 10 Experimental schemes for indirect and competitive ELISAs that were used to quantify the immune response of indicator mice challenged with the HET-2s 14R1 vaccine candidate. The indirect ELISA was used to determine the overall immune response after the HET-2s 14R1 challenge, while the competitive ELISA allowed to quantify the portion of the immune reaction that was targeted against the infectious conformer of the prion protein.
Figure 11:
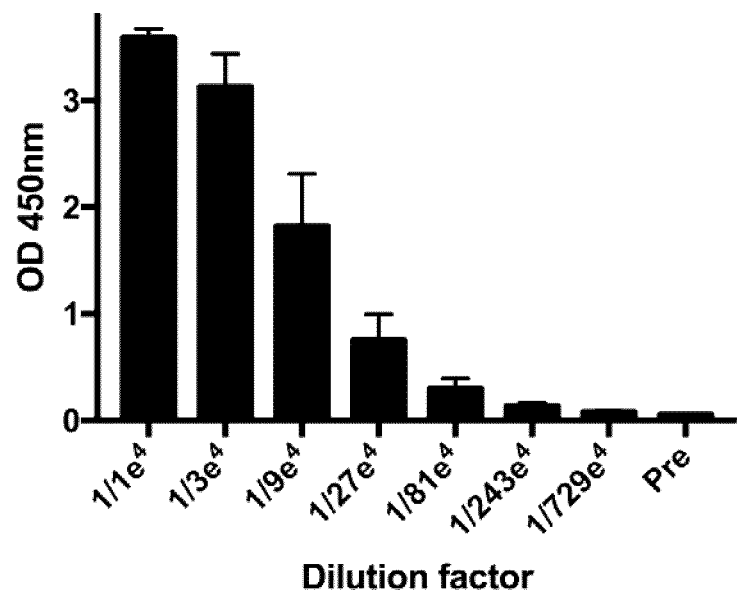
FIG. 11 Titration of the antigen response serum against the HET-2s 14R1 vaccine candidate after the third immunization booster. A serial dilution of the original antigen was used in an indirect ELISA to quantify the immune response.
Figure 12:
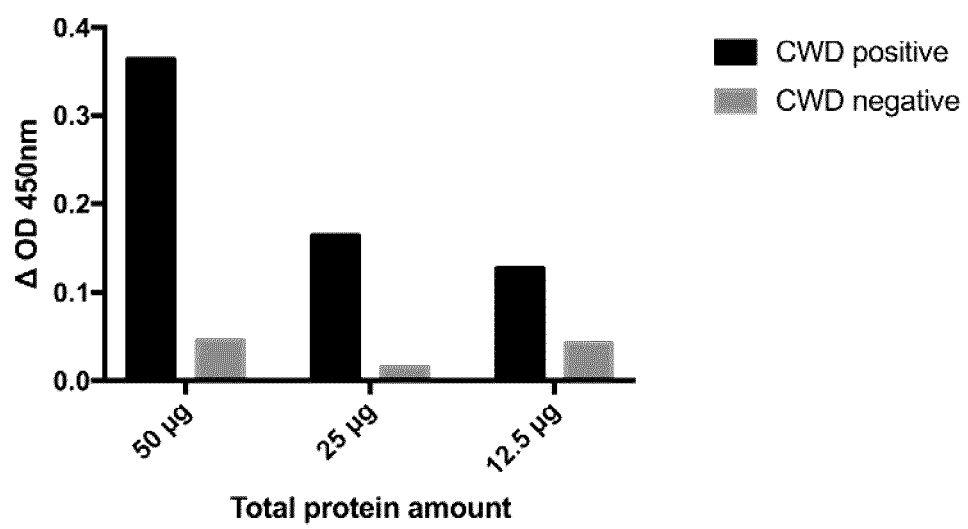
FIG. 12 Titration of a fixed amount of antiserum from a HET-2s 14R1 Immunized mouse against different amounts of brain homogenate from uninfected control animals (CWD negative) and from CWD-infected animals (CWD positive). The raw data were processed by subtracting the absorbance obtained with brain homogenate from a $Pmp^{-/-}$ animal. The values for the CWD negative samples correspond to the background level of the assay, while the CWD positive samples give a strongly positive, dose-dependent signal, suggesting that the antiserum recognizes specifically the infectious conformer of the prion protein.
Figure 13:
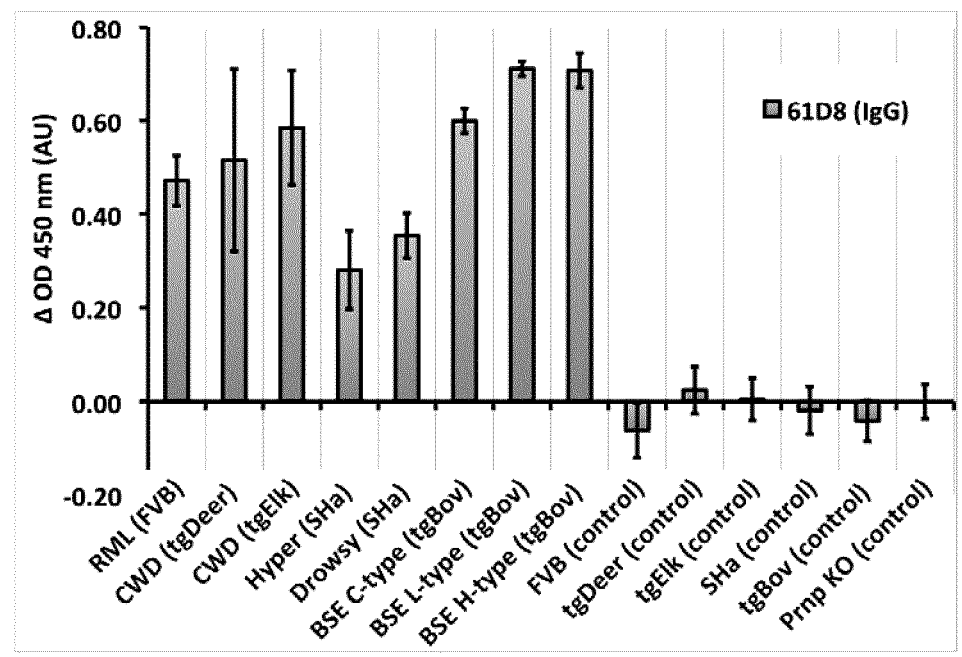
FIG. 13 Competitive ELISA results obtained with the monoclonal antibody 61D8 (IgG) testing crude brain homogenates obtained from prion-infected mouse, transgenic mouse, or hamster brains as well as uninfected control brain homogenates. The monoclonal antibody 61D8 was generated from the 14R1-immunized mice using standard hybridoma technology (Milstein et al., 1978). Consistently, the prion-infected brain homogenates produced a clear difference in ELISA signal (plotted as Δ OD 450 nm) as compared to the non-infected control samples. In detail, 61D8 recognized prions from different isolates: sheep scrapie (RML), chronic wasting disease (CWD), transmissible mink encephalopathy (Hyper & Drowsy), and bovine spongiform encephalopathy (BSE all three Isolates: C-type, L-type, H-type). Twelve other monoclonal antibodies (IgG & IgM) that were generated from the same immunization experiments were found to have the same specificity for native $PrP^{Sc}$ as 61D8. Based on their original plate location, the other IgG clones were designated: 63G4, 1B1, 2A4, 7B6.2, and 17A7.9. Similarly, the IgM clones were designated: M18, 16D5, M63, 40D4, 58E6, M6, and M63.
Figure 14:
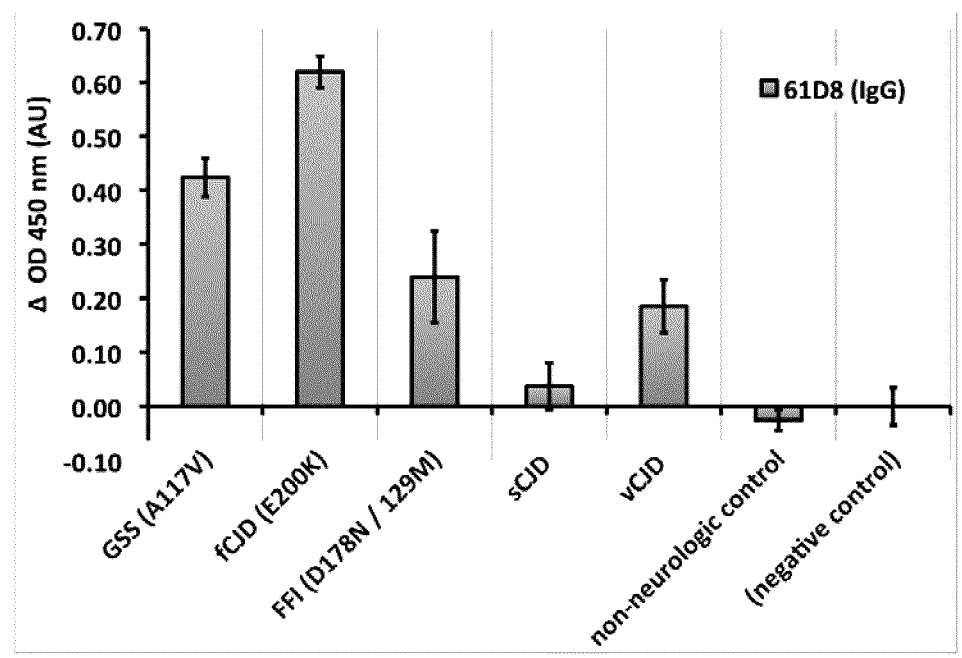
FIG. 14 Competitive ELISA results obtained with the monoclonal antibody 61D8 (IgG) testing crude brain homogenates obtained from patient-derived, prion-infected and non-neurologic control brain homogenates. Consistently, the prion-infected brain homogenates produced a clear difference in ELISA signal (plotted as Δ OD 450 nm) as compared to the non-neurologic control samples. In detail, 61D8 recognized prions from human isolates based on Gerstmann-Strgussler-Scheinker syndrome (GSS A117V mutation), familial Creutzfeldt-Jakob disease (fCJD E200K mutation), fatal familial insomnia (FFI D178N mutation on the codon 129M background), sporadic Creutzfeldt-Jakob disease (sCJD), and variant Creutzfeldt-Jakob disease (vCJD, which is bovine spongiform encephalopathy transmitted to humans).
Figure 16:
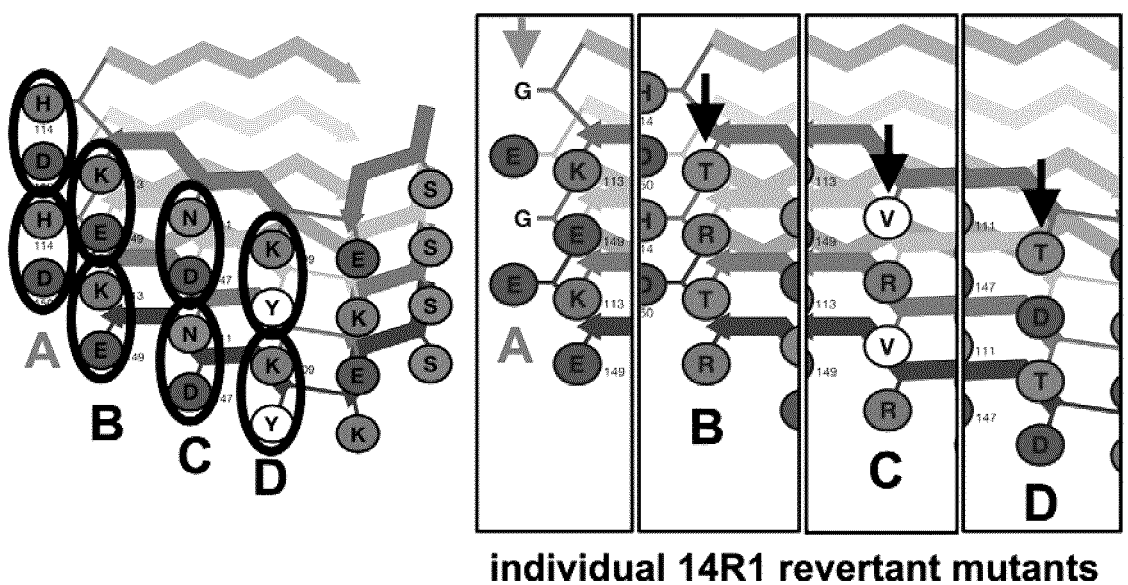
FIG. 16 Revertant mutants of the 14R1 antigen/vaccine candidate to determine the precise epitope of 61D8 and other 14R1-derived antibodies. For each of the constructs two of the amino acids originally inserted to mimic the structure of $PrP^{Sc}$ were reverted to the original HET-s sequence (Wasmer et al., 2008). Since 14R1 is based on a duplicated version of HET-s(218-289), the reversion mutations were applied to both halves of 14R1 (not shown). Constructs A through D reverted amino acids along vertical columns. For the time being, construct A did not produce any successful clones, and could not be tested in the following experiments. In construct B the residues were changed to unrelated amino acids, since lysine and glutamate are the natural residues at these positions in HET-s.
Figure 17:
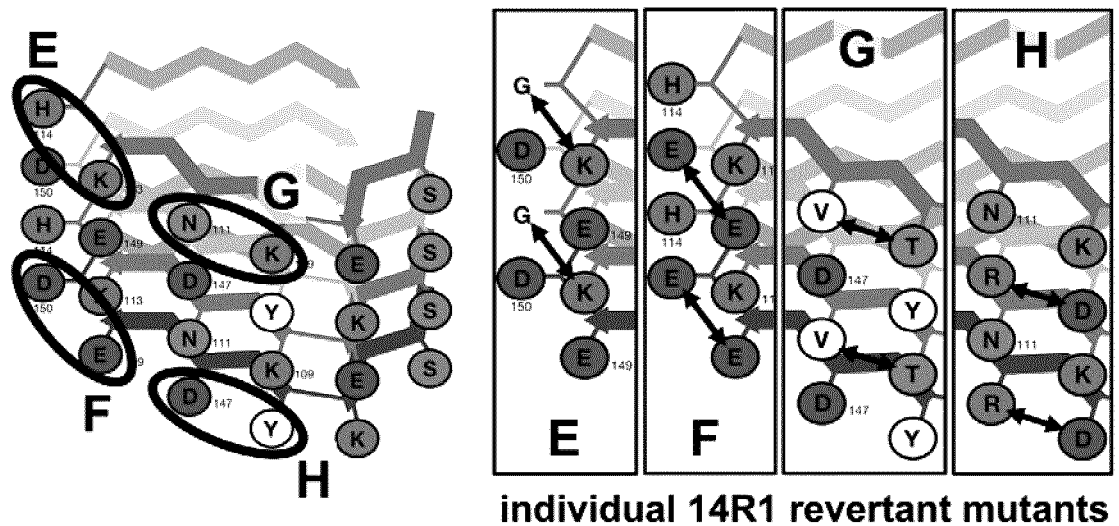
FIG. 17 Revertant mutants of the 14R1 antigen/vaccine candidate to determine the precise epitope of 61D8 and other 14R1-derived antibodies. For each of the constructs two of the amino acids originally inserted to mimic the structure of PrP$^{Sc}$ were reverted to the original HET-s sequence. Since 14R1 is based on a duplicated version of HET-s(218-289), the reversion mutations were applied to both halves of 14R1 (not shown). Constructs E through H reverted amino acids along horizontal rows. In constructs E and F only one residue was changed as the others were identical between 14R1 and the original HET-s(218-289).
Figure 18:
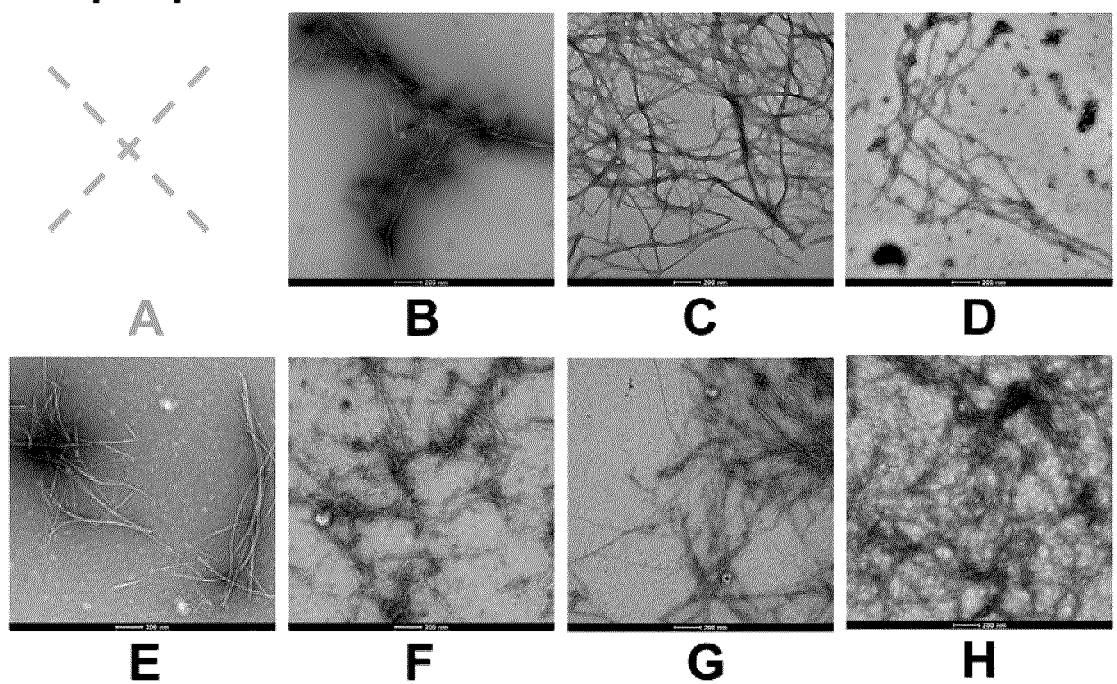
FIG. 18 Negative stain electron micrographs of 14R1 revertant mutants B through H. It is important to note that all constructs form fibrils morphologically identical to unmodified HET-s fibrils (Mizuno et al., 2011), which indicates the proper β-solenoid fold of the recombinantly produced proteins.
Figure 19:
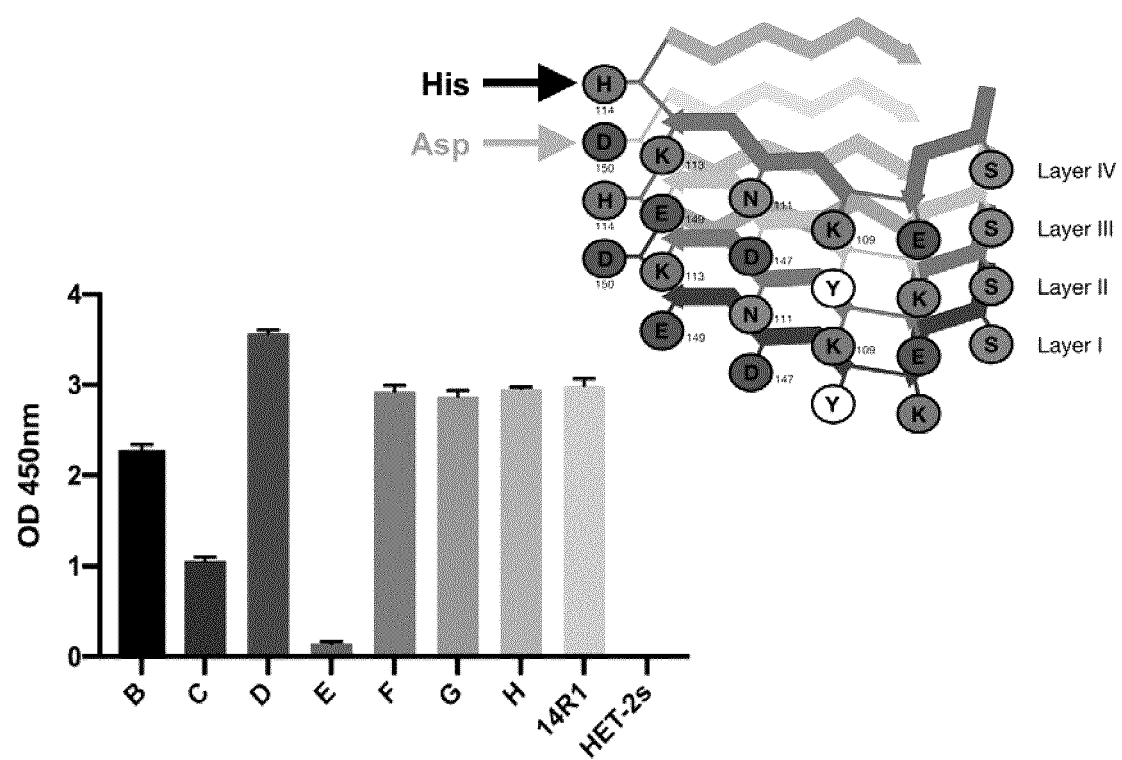
FIG. 19 Epitope mapping using the 14R1 revertant mutants to identify the amino acids that form the core 61D8 epitope. The ELISA results Indicate that most revertant mutants (B, D, F. G. and H) of 14R1 are equally well recognized by the 61D8 antibody as 14R1 itself. In contrast, the revertant mutant "E" shows a ~30 fold reduction in 61D8 binding, which demonstrates the importance of the His residue at the s-ark for the binding of 61D8. The Asp residue underneath the His, on the equivalent β-ark one rung lower, can be replaced by a Glu as demonstrated by the "G" revertant mutant. Removal of the negative charge at this position (data not shown) abolishes the antibody binding revealing its role as part of the 61D8 PrPSc-specific antibody epitope.
Figure 20:
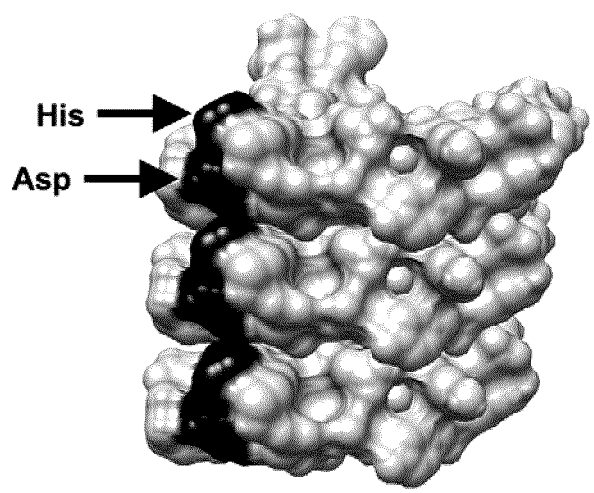
FIG. 20 Modeled structure of the 14R1 vaccine candidate, Indicating the key residues of the 61D8 epitope. Three HET-s(218-289) prion domains are shown stacked into an amyloid fibril (Wasmer et al., 2008), representing 1.5 molecules of the HET-2s 14R1 construct, which contains a duplicated set of HET-s(218-289). The residues that form the core epitope of 61D8 are indicated in black.
Figure 21:
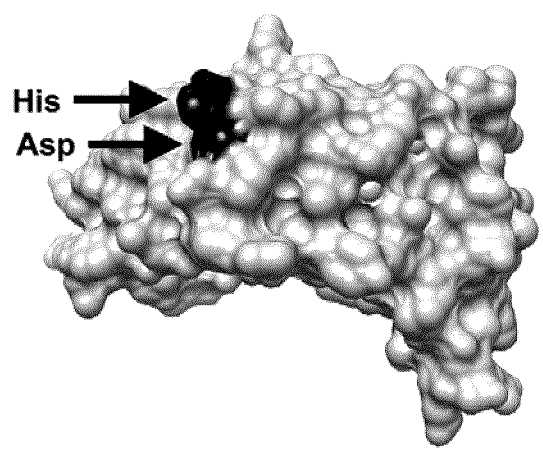
FIG. 21 Model of the structure of PrP$^{Sc}$ with the 61D8 epitope residues highlighted in black. The residues of the 61D8 epitope occupy two, stacked β-solenoid corners (β-arks) in the four-rung β-solenoid fold of the PrP$^{Sc}$ molecule. The PrP$^{Sc}$ model was developed Independently to include all available experimental data on the structure of PrP$^{Sc}$ (Spagnolli et al., 2018), and was found to fit the predictions that lead to the development of the 14R1 vaccine candidate.
Figure 22:
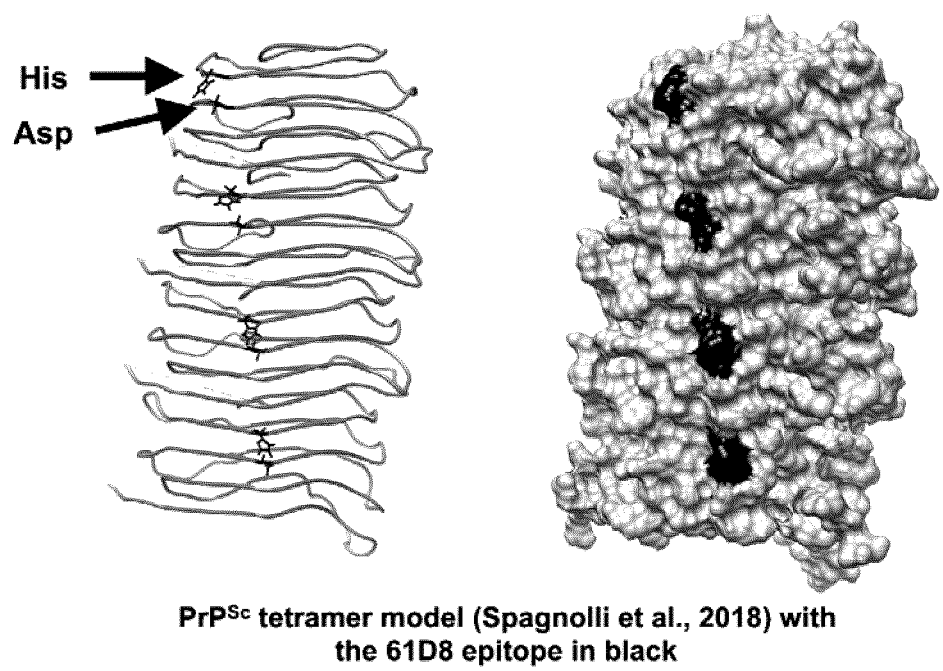
FIG. 22 Model of a PrP$^{Sc}$ fibril with four molecules of PrP$^{Sc}$ stacked on top of each other and the 61D8 epitope residues highlighted in black. A ribbon diagram (left) and a space-filling view (right) indicate the repeating nature of the PrP$^{Sc}$ fibril. The residues of the 61D8 epitope occupy two, stacked β-solenoid corners (s-arks) in the four-rung β-solenoid fold of the PrP$^{Sc}$ molecule. The PrP$^{Sc}$ model was developed independently to include all available experimental data on the structure of PrP$^{Sc}$ (Spagnolli et al., 2018), and was found to fit the predictions that lead to the development of the 14R1 vaccine candidate.
Figure 23:
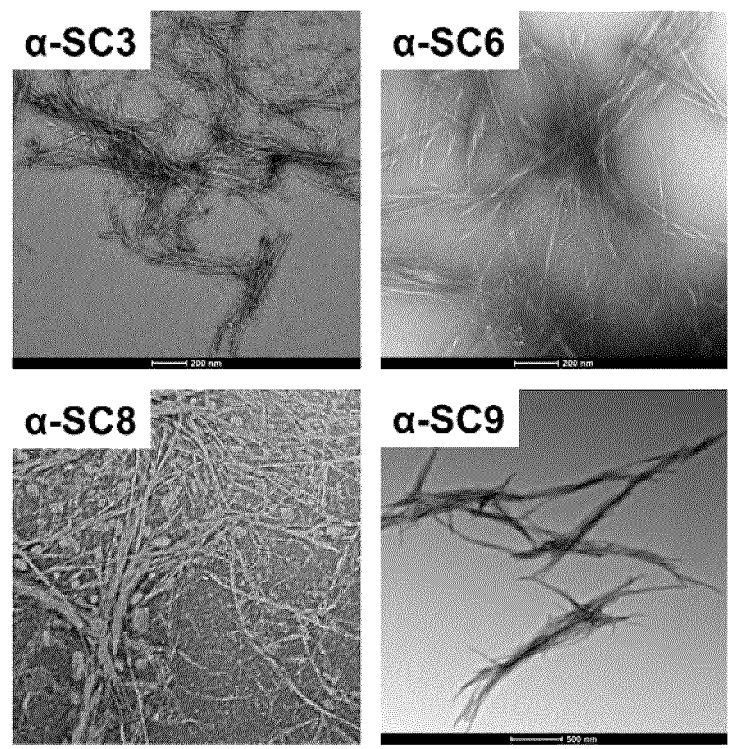
FIG. 23 Negative stain electron micrographs of vaccine candidates targeting Parkinson's disease and other synucleinopathies based on the HET-s(218-289) protein scaffold. Recombinantly generated vaccine candidates were purified, fibrillized in vitro, and analyze via negative stain electron microscopy for the formation of the typical HET-s amyioid fibril morphology (Mizuno et al., 2011). Formation of the characteristic HET-s amyloid fibrils ensures that the rationally-designed antigen structure has been formed as predicted.
Figure 24:
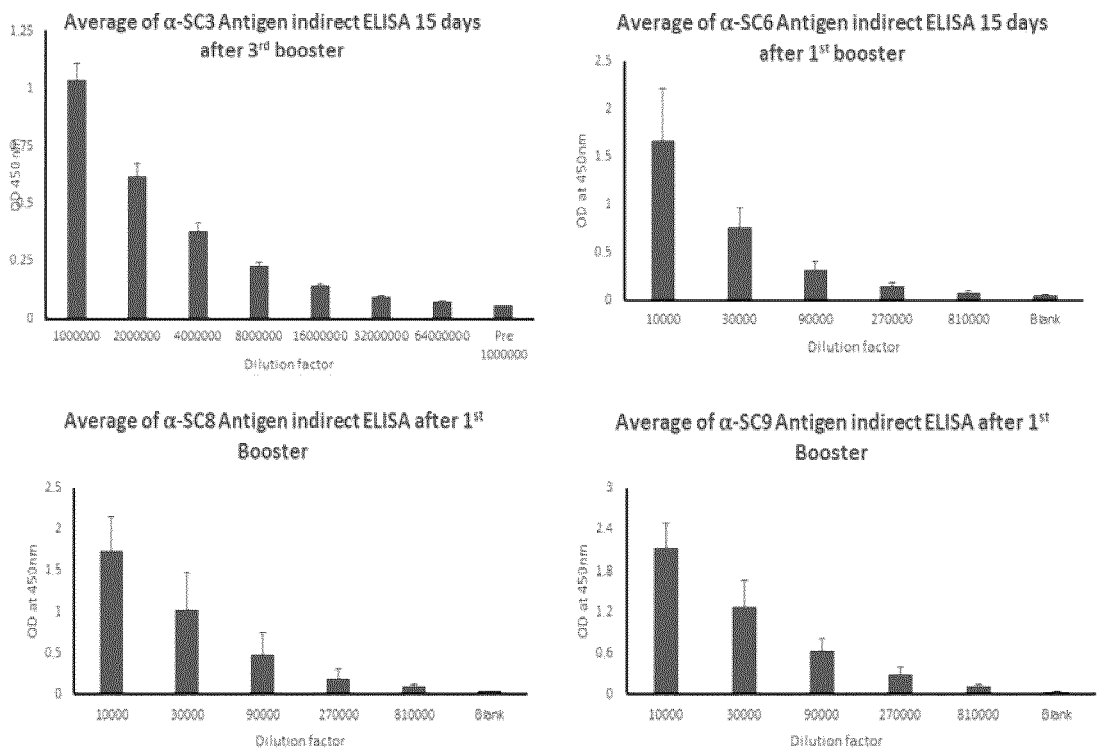
FIG. 24 Titration of the antigen response serum against the HET-s α-SC3, α-SC6, α-SC8, and α-SC9 vaccine candidates after the third or first Immunization booster, respectively. A serial dilution of the antiserum was used in indirect ELISAs on plates coated with the original antigen to quantify the immune responses.
Figure 25:
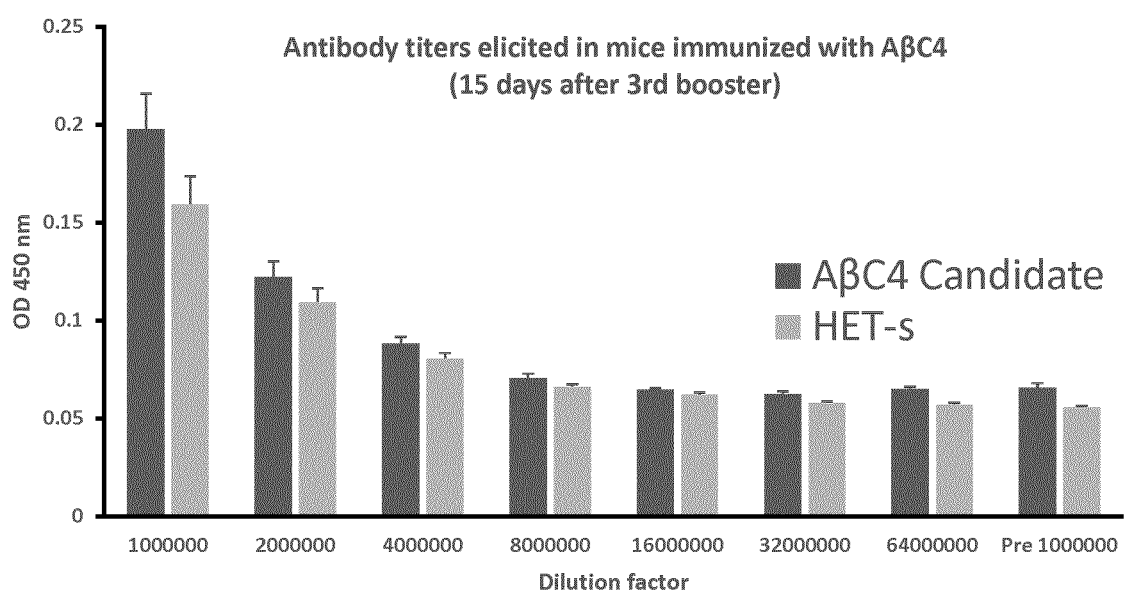
FIG. 25 Titration of the antigen response serum against the HET-s AβC4 vaccine candidate and unmodified HET-s after the third immunization booster. A serial dilution of the antiserum was used in indirect ELISAs on plates coated with the original antigen to quantify the immune responses. The immune response against the HET-s AβC4 antigen was moderately stronger than against unmodified HET-s, Indicating the immunogenic strength of the inserted Aβ surface residues.
Figure 26:
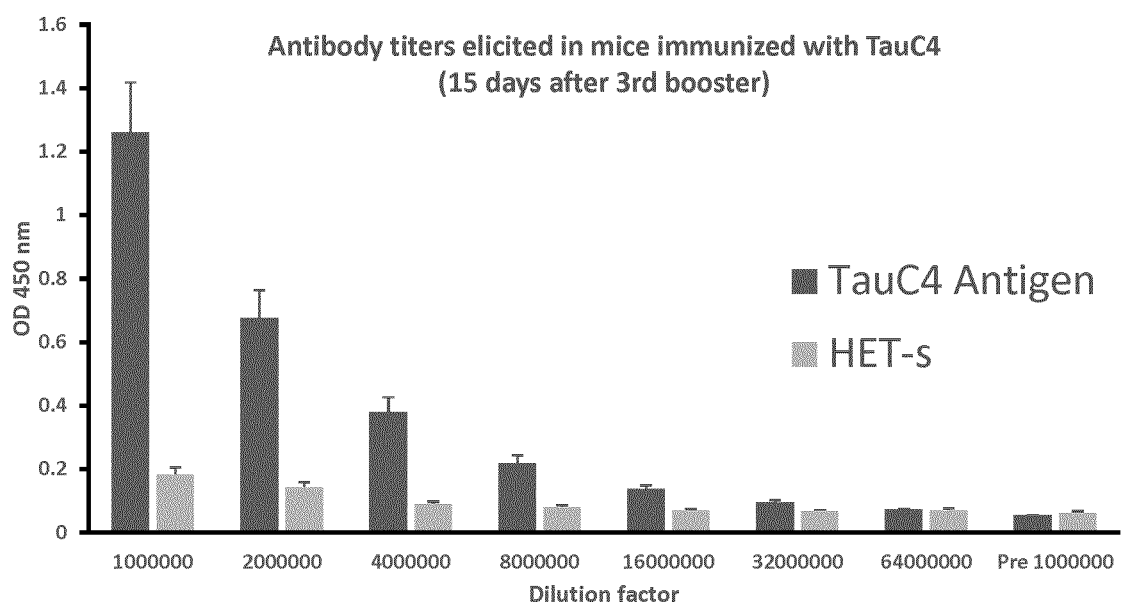
FIG. 26 Titration of the antigen response serum against the HET-s TauC4 vaccine candidate and unmodified HET-s after the third Immunization booster. A serial dilution of the antiserum was used in indirect ELISAs on plates coated with the original antigen to quantify the immune responses. The immune response against the HET-s TauC4 antigen was substantially stronger than against unmodified HET-s, indicating the antigenic efficiency of the inserted Tau surface residues.
Figure 27:
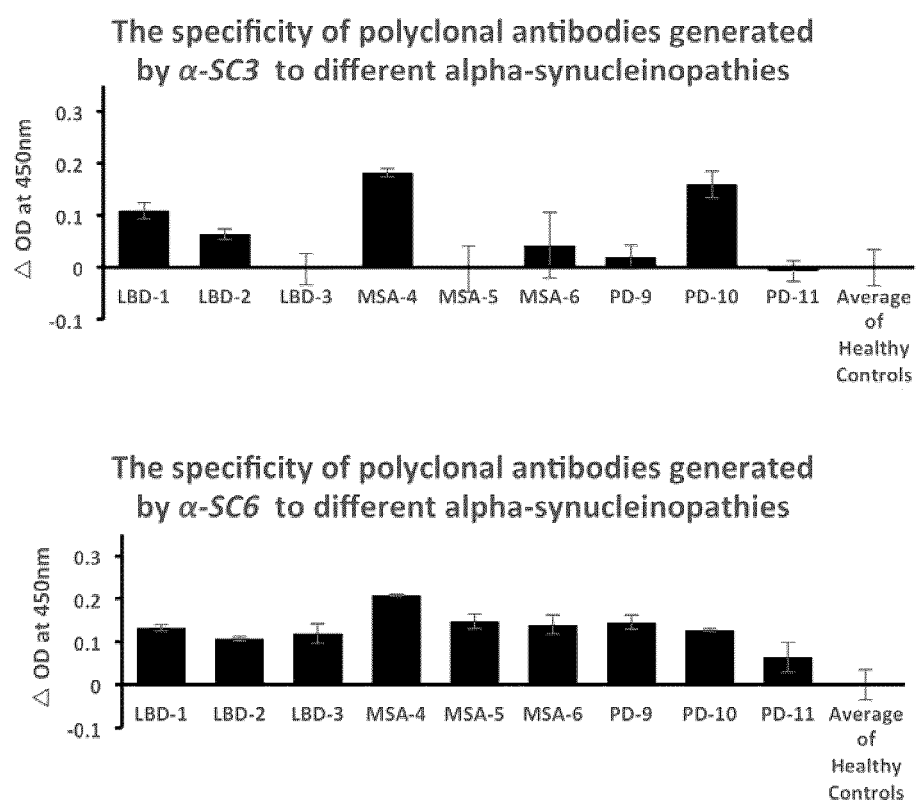
FIG. 27 Competitive ELISA to test the specificity of the immune response obtained with vaccine candidates α-SC3 and α-SC6. Brain homogenates from three separate patients suffering from Lewy body dementia (LBD), Multi systems atrophy (MSA), and Parkinson's disease (PD) were analyzed using the post-immune serum from mice immunized with α-SC3 and α-SC6. The α-SC3-induced immune response resulted in a heterogeneous response were some samples were recognized, while others gave only background readings. In contrast, the α-SC6-induced immune response recognized all disease-associated patient-derived samples, indicating that α-SC6 targeted a more ubiquitously found α-synuclein epitope. The difference in immune responses demonstrates that the design of candidate vaccines and the structures on which they are based are very important, since the α-SC3 construct was based on the structure reported by Tuttle et al., 2016 while the α-SC6 was based on the structure reported by Guerrero-Ferreira et al., 2018.
Figure 29:
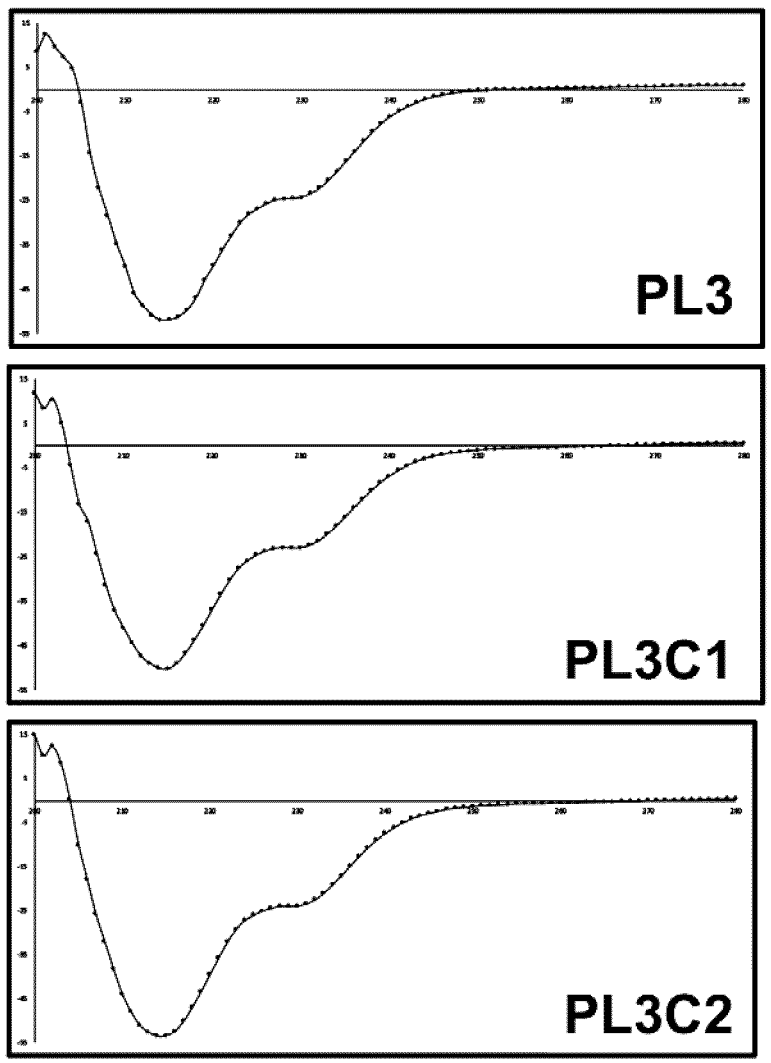
FIG. 29 Circular dichroism spectroscopy measurements indicate that the soluble vaccine scaffold PL3 and the two vaccine candidates PL3C1 and PL3C2 adopt a β-sheet rich conformation. The insertion of the PrP-derived amino acids did not affect the protein folding in any noticeable way.
Figure 30:
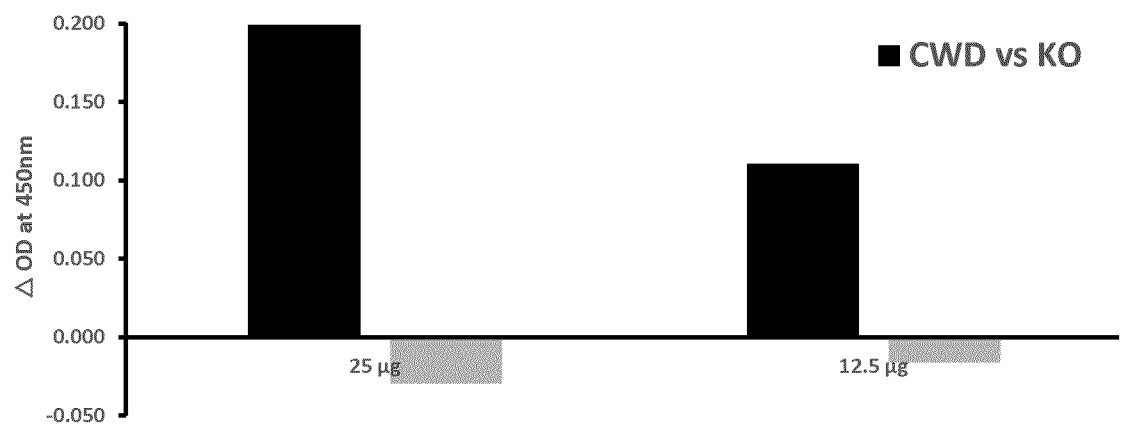
FIG. 30 Titration of a fixed amount of antiserum from a PL3C1 immunized mouse against different amounts of brain homogenate from an uninfected control animal and from a CWD-infected animal (CWD). The raw data were processed by subtracting the absorbance obtained with a brain homogenate from a Pmp$^{-/-}$ animal. The values for the uninfected control sample correspond to the background level of the assay, while the CWD positive samples give a strongly positive, dose-dependent signal, suggesting that the antiserum recognizes specifically the infectious conformer of the prion protein.
Figure 31:
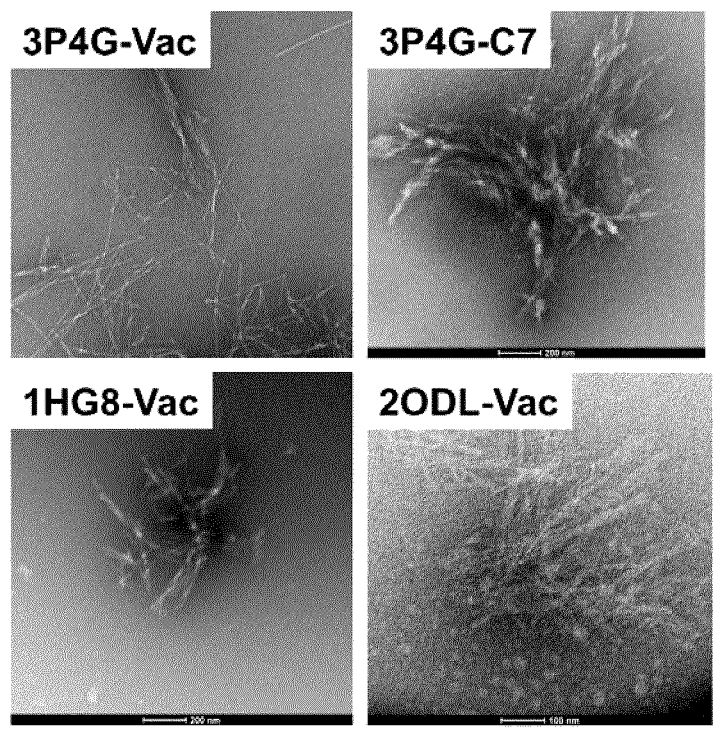
FIG. 31 Negative stain electron micrographs of three right-handed β-solenoid vaccine scaffolds (3P4G-Vac; 1HG8-Vac, and 2ODL-Vac) that were designed to span four-rungs of β-solenoid structure and fibrillize into amyloid fibrils in vitro to mimic the structure of PrP$^{Sc}$. Furthermore, a first vaccine candidate (3P4G-C7) based on the 3P4G-Vac scaffold was engineered to display amino acids from PrP, which are predicted to be exposed in the PrP$^{Sc}$ conformation.

| SEQ ID | SEQUENCE | Location |
| --- | --- | --- |
| 1 | MKIDAIVGRNSAKDIRTEERARVQLNGVVTAAALHGGIRI SDQTTNSVETVVGKGESRVLIGNEYGGKGFWDNGGGG GGGAAGGGGGNSAKDIRTEERARVQLGNVVTAAALHG GIRISDQTTNSVETVVGKGESRVLIGNEYGGKGFWDNH HHHHH | FIG 3, 32 |
| 2 | MVKSHIGSWILVLFVAMWSDVGLCKKRPKPGGGWNTG GSRYPGQGSPGGNRYPPQGGGGWGQPHGGGWGQP HGGGWGQPHGGGWGQPHGGGGWGQGGTHSQWNK PSKPKTNMKHVAGAAAAGAVVGGLGGYMLGSAMSRPLI HFGNDYEDRYYRENMYRYPNQVYYRPVDQYNNQNTFV HDCVNITVKQHTVTTTTKGENFTETDIKMMERVVEQMCI TQYQRESQAYYQRGASVILFSSPPVILLISFLIFLIVG | 4, 34, 44, 46, 47 |
| 3 | MKIDAIVGRNSAKYIDTEDRAEVQLGNVVTAAALHGGIRI SDQTTNSVEKVNGKHESRVRLIGNEYGGKGFWDNGGG GGGGAAGGGGGNSAKYIDTEDRAEVQLGNVVTAAALH GGIRISDQTTNSVEKVNGKHESRVLIGNEYGGKGFWDN HHHHHH | 6, 34 |
| 4 | CKASGYSFTSYWMHWVKQRPGQGLEWIGMIDPSDSET KLNQQFKDKATLTVDTSSSTAYMQLTSPTSEDSVVYYCA RGKMGGRFYFDYLGQGTTLTVSSAKTTPPSVYPLA | 15 |
| 5 | YSFTSYWMH | 15 |
| 6 | MIDPSDSETKLNQQFKD | 15 |
| 7 | ITCKASQDVGTAVVWYQQKPGQSPKLLIYWASTRHTGV PDRFTGSGFGTDFTLTISNVQSEDLADYFCQQFSSYPYT FGGGTKLEIKRADAAPTVS | 15 |
| 8 | KASQDVGTAVV | 15 |
| 9 | WASTRHT | 15 |
| 10 | QQFSSYPYT | 15 |

TABLE 1-continued

| SEQ ID | SEQUENCE | Location |
|---|---|---|
| 11 | MKIDAIVGRNSAKDIRTEERARVQLGNVVTAAALHGGIRI SDQTTNSVETVVGKGESRVLIGNEYGGKGFWDNHHHH HH | 33 |
| 12 | DAEFRHDSGYEVHHQKLVFFAEDVGSNKGAIIGLMVGG WVIA | 35, 36 |
| 13 | MKIDAIVGRNSAVFIETDGSAKVQLGNVVTAAALHGGIRI SDQTTNSVVFVEGDGSSKVLIGNEYGGKGFWDNHHHH HH | 35 |
| 14 | MKIDAIVGRNRADDIYTVEHAKVQLGNVVTAAALHGGIRI SDQTTNRVDTVYGVHSKVLIGNEYGGKGFWDNHHHH HH | 36 |
| 15 | VQIVYKDLPVSKVTSKCGSLGNIHHKPGGGQVEVKSEKL DFKDRVQSKIGSLDNITHVPGGGNKKIETHKLTF | 37, 38 |
| 16 | MKIDAIVGRNKAEKIDTKDRAQVKLGNVVTAAALHGGIRI SDQTTNKVEKVDGKDRSQVKIGNEYGGKGFWDNHHHH HH | 37 |
| 17 | MKIDAIVGRNKAEKIDTKEDARVQLGNVVTAAALHGGIRI SDQTTNKVEKVDGKGDSRVQIGNEYGGKGFWDNHHHH HH | 38 |
| 18 | MDVFMKGLSKAKEGVVAAAEKTKQGVAEAAGKTKEGVL YVGSKTKEGVVHGVATVAEKTKEQVTNVGGAVVTGVTA VAQKTVEGAGSIAAATGFVKKDQLGKNEEGAPQEGILED MPVDPDNEAYEMPSEEGYQDYEPEA | 39, 40, 41, 42 |
| 19 | MKIDAIVGRNSAQVINTGGRARVQLGNVVTAAALHGVAT IAEQTTNSVQVVNGGGESRVLIGNEYGGKGFWDNHHH HHH | 39 |
| 20 | MKIDAIVGRNSAKDIKTVEGARVQLGNVVTAAALHGGIRI SDQTTNSVETVKGVEGSRVLIGNEYGGKGFWDNHHHH HH | 40 |
| 21 | MKIDAIVGKNQATDIRTEERARVQLGNVVTAAALHGGIRI SDQTKNQVTTVVGKGESRVLIGNEYGGKGFWDNHHHH HH | 41 |
| 22 | MKIDAIVGRNKAVEIATEERARVQLGNVVTAAALHGGIRI SDQTTNKVVEVAGKGESRVLIGNEYGGKGFWDNHHHH HH | 42 |
| 23 | MNVSQSNSFGFWDGTSTQAEITHSFDHYIGSAFDASNN NVAVTGNVSATLNVLAGDDKVSIDGNVEDVLVAANVAVL DMGTGNDQLYVAGDVLGKIDAGTGNDEIYIKGDVSAAVD AGTGNDEVYIGGNLSGDLDAGTDNDNIQIGGDVNAALNA GTGNDNLIIGHDVSGIVNMGTDNDTVEVGRTINASGKVL LDTGDDSLLVSGDLFGEVDGGTGNDTIIIAGKVSGNIQG GTGNDIVRVQSQVWAEANISLGTGDDVLIVEHELHGTVA GNEGDDSIYLKFYTKEQYNNNSDLRNRVANFEHIRVSDG VVKGSPADFADY | 43 |
| 24 | MAHHHHHHVGTENLYFQGDLKVLAGDDKVSIDGNVSGA LDMGTGNDQLYVAGDVLGKIDAGTGNDEIYIKGDVSAAV DAGTGNDEVYIGGNLSK | 43 |
| 25 | MAHHHHHHVGTENLYFQGDLKVLAGDDKVSIDGNVSGA LDMGTGNDQLYVAGDVLGKIDAGTGLDSIMIKGDVSAAV DAGTGQDNVQIGGNLSK | 44 |
| 26 | MAHHHHHHVGTNTGGVLVITDTIIVKSGQTYDGKGIKIIA QGMGDGSQSENQKPIFKLEKGANLKNVIIGAPGCDGIHC YGDNVVENVVWEDVGADALTVKSEGVVEVIGGSAKEAA DKVFQLNAPCTFKVKNFTATNIGKLVRQNGNTTFKVVIYL EDVTLNNVKSCVAKSDSPVSELWYHNLNVNNCKTLFEF PSQSQIHQY | 45 |
| 27 | MAHHHHHHVGTNTGGVLVITDTIIVKSGQTYDGKGIKIIA QGMGDGSQSENQKPIFKLEKGANLKNVIIGAPGCDGIHC YGDNVVENVVWEDVGADALTVKSEGVVEVIKGNAKHAA | 46 |

TABLE 1-continued

| SEQ ID | SEQUENCE | Location |
|---|---|---|
|  | DKVFQLNAPCTFKVKNFDAEDIGKLVRQNGNTTFKVVIY LEKVNLKHVKSCVAKSDSPVSELWYHNLDVEDCKTLFEF PSQSQIHQY | |
| 28 | MAHHHHHHVGTNTGGVLVITDTIIVKSGQTYDGKGIKIIA QGMGDGSQSENQKPIFKLEKGANLKNVIIGAPGCDGIHC YGDNVVENVVWEDVGADALTVKSEGVVEVIGGDAEDAA DKVFQLNAPCTFKVKKFNAKHIGKLVRQNGNTTFKVVIYL EDVDLEDVKSCVAKSDSPVSELWYHKLNVKHCKTLFEF PSQSQIHQY | 47 |
| 29 | SGLQGMDVVHGTATMQVDGNKTIIRNSVDAIINWKQFNI DQNEMVQFLQENNNSAVFNRVTSNQISQLKGILDSNGQ VFLINPNGITIGKDAIINTNGFTASTLDISNENIKARNFTFE QTKDKALAEIVNHGLITVGKDGSVNLIGGKVKNEGVISVN GGSISLLAGQKITISDIINPTITYSIAAPENEAVNLGDIFAKG GNINVRAATIRNQGKLSADSVSKDGSGNIVLSAKEGEAEI GGVISAQNQQAKGGKLMITGDKVTLKTGAVIDLSGKEGG ETYLGGDERGEGKNGIQLAKKTSLEKGSTINVSGKEKGG RAIVWGDIALIDGNINAQGSGDIAKTGGFVETSGHDLFIK DNAIVDAKEWLLD | 48 |
| 30 | MAHHHHHHVGTENLYFQGKEIVNHGLITVGDGSVNLIGG KVKNEGVISVNGGSISLLAGEAVNLGDIFAKGGNINVRAA TIRNQGKLSAGKGNIVLSAGE | 48 |
| 31 | DPCSVTEYSGLATAVSSCKNIVLNGFQVPTGKQLDLSSL QNDSTVTFKGTTTFATTADNDFNPIVISGSNITITGASGH VIDGNGQAYWDGKGSNSNSNQKPDHFIVVQKTTGNSKI TNLNIQNWPVHCFDITGSSQLTISGLILDNRAGDKPNAKS GSLPAAHNTDGFDISSSDHVTLDNNHVYNQDDCVAVTS GTNIVVSNMYCSGGHGLSIGSVGGKSDNVVDGVQFLSS QWVNSQNGCRIKSNSGATGTINNVTYQNIALTNISTYGVD VQQDYLNGGPTGKPTNGVKISNIKFIKVTGTVASSAQDW FILCGDGSCSGFTFSGNAITGGGKTSSCNYPTNTCPS | 49 |
| 32 | MAHHHHHHVGTENLYFQGDGFDISSSDHVTLDNNHVYN QDDCVAVTSGTNIVVSNMYCSGGHGLSIGSVGGKSDNV VDGVQFLSSQVVNSQNGCRIKSNSGATGTINNVTYQNIA LTNISR | 49 |
| 33 | MKIDAIVGRNSAKDIRTEERARVQLGNVVTAAALHGGIRI SDQTTNCVETWGKGESRVLIGNEYGGKGFWDNGGGG GGGAAGGGGNSAKDIRTEERARVQLGNVVTAAALHG GIRISDQTTNSVETWGKGESRVLIGNEYGGKGFWDN | Claims |
| 34 | MKIDAIVGRNSAKYIDTEDRAEVQLGNWTAAALHGGIRI SDQTTNSVEKVNGKHESRVRLIGNEYGGKGFWDNGGG GGGGAAGGGGGNSAKYIDTEDRAEVQLGNVVTAAALH GGIRISDQTTNSVEKVNGKHESRVLIGNEYGGKGFWDN | Claims |
| 35 | GKMGGRFYFDY | FIG 15 |

REFERENCES

Balguerie, A.; Dos Reis, S.; Ritter, C.; Chaignepain, S.; Coulary-Salin, B.; Forge, V.; Bathany, K.; Lascu, I.; Schmitter, J. M.; Risk, R.; et al. (2003). Domain Organization and Structure-Function Relationship of the HET-S Prion Protein of *Podospora Anserina*. EMBO J. 22, 2071-2081.

Bryan, A. W., Stamer-Kreinbrink, J. L., Hosur, R., Clark, P. L., & Berger, B. (2011). Structure-based prediction reveals capping motifs that inhibit β-helix aggregation. Proceedings of the National Academy of Sciences U.S.A. 108(27), 11099-11104.

Caughey, B. W.; Dong, A.; Bhat, K. S.; Ernst, D.; Hayes, S. F.; Caughey, W. S. (1991). Secondary structure analysis of the scrapie-associated protein PrP 27-30 in water by infrared spectroscopy. Biochemistry 30, 7672-7680.

Choi J H, Govaerts C, May B C, Cohen F E (2008). Analysis of the sequence and structural features of the left-handed beta-helical fold. Proteins, 73:150-160.

Choi J H, May B C, Govaerts C, Cohen F E (2009). Site-directed mutagenesis demonstrates the plasticity of the beta helix: implications for the structure of the misfolded prion protein. Structure, 17:1014-1023.

Coustou, V.; Deleu, C.; Saupe, S.; Begueret, J. (1997). The Protein Product of the Het-S Heterokaryon Incompatibility Gene of the Fungus *Podospora anserina* Behaves as a Prion Analog. Proc. Nati. Acad. Sci. USA 94, 9773-9778.

Daskalov A, Gantner M, Wälti M A, Schmidlin T, Chi C N, Wasmer C, Schütz A, Ceschin J, Clavé C, Cescau S, Meier B, Riek R, Saupe S J (2014). Contribution of specific residues of the β-solenoid fold to HET-s prion function, amyloid structure and stability. PLoS Pathogens, 10:e1004158.

de Brevern A. G. (2016). Extension of the classical classification of β-turns. Sci Rep. 6, e33191.

Dos Reis, S.; Coulary-Salin, B.; Forge, V.; Lascu, I.; Bêgueret, J.; Saupe, S. J. (2002). The HET-S Prion Protein of the Filamentous Fungus *Podospora anserina* Aggregates in Vitro into Amyloid-like Fibrils. J. Biol. Chem. 277, 5703-5706.

Fitzpatrick, A. W. P., Falcon, B., He, S., Murzin, A. G., Murshudov, G., Garringer, H. J., Crowther, R. A., Ghetti, B., Goedert, M., Scheres, S. H. W. (2017). Cryo-EM Structures of Tau Filaments from Alzheimer's Disease. Nature 547, 185-190.

Flores-Fernãndez, J. M., Rathod, V., and Wille, H. (2018). Comparing the folds of prions and other pathogenic amyloids. Pathogens, 7, e50.

Goñi F, Mathiason C K, Yim L, Wong K, Hayes-Klug J, Nails A, Peyser D, Estevez V, Denkers N, Xu J, Osborn D A, Miller K V, Warren R J, Brown D R, Chabalgoity J A, Hoover E A, Wisniewski T (2015). Mucosal immunization with an attenuated Salmonella vaccine partially protects white-tailed deer from chronic wasting disease. Vaccine 33:726-733.

Govaerts, C.; Wille, H.; Prusiner, S. B.; Cohen, F. E. (2004). Evidence for Assembly of Prions with Left-Handed β-Helices into Trimers. Proc. Nati. Aced. Sci. USA 101, 8342-8347.

Greenwald, J.; Buhtz, C.; Ritter, C.; Kwiatkowski, W.; Choe, S.; Maddelein, M.-L.; Ness, F.; Cescau, S.; Soragni, A.; Leitz, D.; et al. (2010). The Mechanism of Prion Inhibition by HET-S. Mol. Cell 38, 889-899.

Gremer, L., Schölzel, D., Schenk, C., Reinartz, E., Labahn, J., Ravelli, R. B. G., Tusche, M., Lopez-Iglesias, C., Hoyer, W., Heise, H., et al. (2017). Fibril Structure of Amyloid-β(1-42) by Cryoelectron Microscopy. Science 358, 116-119.

Guerrero-Ferreira, R.; Nicholas, M. I.; Mona, T. D.; Ringler, P.; Lauer, M. E.; Riek, R.; Britschgi, M.; Stahlberg, H. (2018). Cryo-EM structure of alpha-synuclein fibrils. bioRxiv 2018, 276436.

Hedlin P, Taschuk R, Potter A, Griebel P, Napper S (2012). Detection and control of prion diseases in food animals. ISRN Veterinary Science 2012:254739.

Hennetin, J.; Jullian, B.; Steven, A. C.; Kajava, A. V. (2006). Standard Conformations of β-Arches in β-Solenoid Proteins. J. Mol. Biol. 358, 1094-1105.

Henrissat, B.; Heffron, S. E.; Yoder, M. D.; Lietzke, S. E.; Jumak, F. (1995). Functional Implications of Structure-Based Sequence Alignment of Proteins in the Extracellular Pectate Lyase Superfamily. Plant Physiol. 107, 963-976.

Iengar P., Joshi N. V., Balaram P. Conformational and sequence signatures in beta helix proteins. Structure, 3, 529-542.

Jenkins, J. & R. Pickersgill (2001). The architecture of parallel β-helices and related folds. Progress in Biophysics and Molecular Biology 77(2), 111-175.

Kajava, A. V. & Steven, A. C. (2006a). β-Rolls, β-Helices, and Other β-Solenoid Proteins. Adv. Protein Chem. 73, 55-96.

Kajava, A. V. & Steven, A. C. (2006b). The Turn of the Screw: Variations of the Abundant β-Solenoid Motif in Passenger Domains of Type V Secretory Proteins. J. Struct. Biol. 155, 306-315.

Kajava, A. V.; Baxa, U.; Steven, A. C. (2010). Beta Arcades: Recurring Motifs in Naturally Occurring and Disease-Related Amyloid Fibrils. FASEB J. 24, 1311-1319.

Kobe, B. & Kajava, A. V. (2000). When Protein Folding Is Simplified to Protein Coiling: The Continuum of Solenoid Protein Structures. Trends Biochem. Sci. 25, 509-515.

Kondo, H.; Hanada, Y.; Sugimoto, H.; Hoshino, T.; Garnham, C. P.; Davies, P. L.; Tsuda, S. (2012). Ice-Binding Site of Snow Mold Fungus Antifreeze Protein Deviates from Structural Regularity and High Conservation. Proc. Natl. Acad. Sci. USA 109, 9360-9365.

Li B, Ge P, Murray K A, Sheth P, Zhang M, Nair G, Sawaya M R, Shin W S, Boyer D R, Ye S, Eisenberg D S, Zhou Z H, Jiang L (2018a). Cryo-EM of full-length α-synuclein reveals fibril polymorphs with a common structural kernel. Nat Commun. 9, e3609.

Li Y, Zhao C, Luo F, Liu Z, Gui X, Luo Z, Zhang X, Li D, Liu C, Li X (2018b). Amyloid fibril structure of α-synuclein determined by cryo-electron microscopy. Cell Res, 9, 897-903.

Liebman, S. W. & Chemoff, Y. O. (2012). Prions in Yeast. Genetics 191, 1041-1072.

Mabbott N A (2015). Prospects for safe and effective vaccines against prion diseases. Expert Review of Vaccines 14:1-4.

Milstein C, Adetugbo K, Cowan N J, Kohler G, Secher D S (1978). Expression of antibody genes in tissue culture: structural mutants and hybrid cells. Nati Cancer Inst Monogr, 48, 321-330.

Mizuno, N.; Baxa, U.; Steven, A. C. (2011). Structural Dependence of HET-S Amyloid Fibril Infectivity Assessed by Cryoelectron Microscopy. Proc. Natl. Acad. Sci. USA 108, 3252-3257.

Pan, K. M.; Baldwin, M.; Nguyen, J.; Gasset, M.; Serban, A.; Groth, D.; Mehlhorn, I.; Huang, Z.; Fletterick, R. J.; Cohen, F. E. (1993). Conversion of α-Helices into β-Sheets Features in the Formation of the Scrapie Prion Proteins. Proc. Natl. Acad. Sci. USA 90, 10962-10966.

Peng, J., & Xu, J. (2011). RaptorX: exploiting structure information for protein alignment by statistical inference. Proteins: Structure, Function, and Bioinformatics 79(S10), 161-171.

Peralta M D, Karsai A, Ngo A, Sierra C, Fong K T, Hayre N R, Mirzaee N, Ravikumar K M, Kluber A J, Chen X, Liu G Y, Toney M D, Singh R R, Cox D L (2015). Engineering amyloid fibrils from β-solenoid proteins for biomaterials applications. ACS Nano, 9, 449-463.

Pilon J L, Rhyan J C, Wolfe L L, Davis T R, McCollum M P, O'Rourke K I, Spraker T R, VerCauteren K C, Miller M W, Gidlewski T, Nichols T A, Miller L A, Nol P (2013). Immunization with a synthetic peptide vaccine fails to protect mule deer (*Odocoileus hemionus*) from chronic wasting disease. Journal of Wildlife Diseases 49:694-698.

Ritter, C.; Maddelein, M.-L.; Siemer, A. B.; Lührs, T.; Ernst, M.; Meier, B. H.; Saupe, S. J.; Riek, R. (2005). Correlation of Structural Elements and Infectivity of the HET-S Prion. Nature 435, 844-848.

Silva, C. J., Vâzquez-Fernãndez, E.; Onisko, B.; Requena, J. R. (2015). "Proteinase K and the structure of PrPSc: The good, the bad and the ugly." Virus Research 207: 120-126.

Smirnovas, V.; Baron, G. S.; Offerdahl, D. K.; Raymond, G. J.; Caughey, B.; Surewicz, W. K. (2011). Structural Organization of Brain-Derived Mammalian Prions Examined by Hydrogen-Deuterium Exchange. Nat. Struct. Mol. Biol. 18, 504-506.

Spagnolli, G, Rigoli, M, Orioli, S, Sevillano, A M, Faccioli, P, Wille, H, Biasini, E, and Requena, JR (2018). Full atomistic model of prion structure and conversion. bioRxiv. http://dx.doi.org/10.1101/505271.

Thuermer Jr. A M (2015). WyoFile: http://www.wyofile.com/chronic-wasting-disease-vaccine-fails-elk-test Tsemekhman, K.; Goldschmidt, L.; Eisenberg, D. S.; Baker, D. (2007). Cooperative Hydrogen Bonding in Amyloid Formation. Protein Sci. 16, 761-764.

Tuttle, M. D., Comellas, G., Nieuwkoop, A. J., Covell, D. J., Berthold, D. A., Kloepper, K. D., Courtney, J. M., Kim, J. K., Barclay, A. M., Kendall, A., at al. (2016). Solid-State NMR Structure of a Pathogenic Fibril of Full-Length Human α-Synuclein. Nat. Struct. Mol. Biol. 23, 409-415.

van Melckebeke, H.; Wasmer, C.; Lange, A.; Ab, E.; Loquet, A.; Böckmann, A.; Meier, B. H. (2010). Atomic-Resolution Three-Dimensional Structure of HET-S(218-289) Amyloid Fibrils by Solid-State NMR. J. Am. Chem. Soc. 132, 13765-13775.

Vâzquez-Fernândez, E.; Alonso, J.; Pastrana, M. A.; Ramos, A.; Stitz, L.; Vidal, E.; Dynin, I.; Petsch, B.; Silva, C. J.; Requena, J. R. (2012). Structural Organization of Mammalian Prions as Probed by Limited Proteolysis. PLoS ONE 7, e50111.

Vâzquez-Fernândez, E.; Vos, M. R.; Afanasyev, P.; Cebey, L.; Sevillano, A. M.; Vidal, E.; Rosa, I.; Renault, L.; Ramos, A.; Peters, P. J.; at al. (2016). The Structural Architecture of an Infectious Mammalian Prion Using Electron Cryomicroscopy. PLoS Pathog. 12, e1005835.

Wälti, M. A.; Ravotti, F.; Arai, H.; Glabe, C. G.; Wall, J. S.; Böckmann, A.; Güntert, P.; Meier, B. H.; Risk, R. (2016). Atomic-resolution structure of a disease-relevant Aβ(1-42) amyloid fibril. Proc. Natl. Acad. Sci. USA 113, E4976-E4984.

Wan, W.; Wille, H.; Stöhr, J.; Baxa, U.; Prusiner, S. B.; Stubbs, G. (2012). Degradation of fungal prion HET-s(218-289) induces formation of a generic amyloid fold. Biophys. J. 102, 2339-2344.

Wan, W. (2014). Structure and assembly of the fungal prion-forming domain HET-s(218-289). Dissertation, Vanderbilt University, Nashville, TN, USA.

Wan, W. & Stubbs, G. (2014). Fungal Prion HET-S as a Model for Structural Complexity and Self-Propagation in Prions. Proc. Natl. Acad. Sci. USA 111, 5201-5206.

Wan, W.; Wille, H.; Stöhr, J.; Kendall, A.; Bian, W.; McDonald, M.; Tiggelaar, S.; Watts, J. C.; Prusiner, S. B.; Stubbs, G. (2015). Structural Studies of Truncated Forms of the Prion Protein PrP. Biophys. J. 108, 1548-1554.

Wasmer, C.; Lange, A.; Melckebeke, H. Van; Siemer, A. B.; Riek, R.; Meier, B. H. (2008). Amyloid Fibrils of the HET-s(218-289) Prion Form a B Solenoid with a Triangular Hydrophobic Core. Science 319, 1523-1527.

Wickner, R. B. (1997). A New Prion Controls Fungal Cell Fusion Incompatibility. Proc. Natl. Acad. Sci. USA 94, 10012-10014.

Wille, H.; Michelitsch, M. D.; Guenebaut, V.; Supattapone, S.; Serban, A.; Cohen, F. E.; Agard, D. A.; Prusiner, S. B. (2002). Structural Studies of the Scrapie Prion Protein by Electron Crystallography. Proc. Natl. Acad. Sci. USA 99, 3563-3568.

Wille, H.; Bian, W.; McDonald, M.; Kendall, A.; Colby, D. W.; Bloch, L.; Ollesch, J.; Borovinskiy, A. L.; Cohen, F. E.; Prusiner, S. B.; et al. (2009). Natural and Synthetic Prion Structure from X-Ray Fiber Diffraction. Proc. Natl. Acad. Sci. USA 106, 16990-16995.

Wille, H. & Requena, J. R. (2018). The Structure of PrP$^{Sc}$ Prions. Pathogens 7, e20.

Yoder, M. D.; Lietzke, S. E.; Jumak, F. (1993). Unusual Structural Features in the Parallel β-Helix in Pectate Lyases. Structure 1, 241-251.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are Indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. An isolated recombinant polypeptide comprising or consisting of: a β-solenoid structured polypeptide comprising amino acids from an innocuous β-solenoid scaffold polypeptide and a plurality of epitope amino acids from a disease associated polypeptide, wherein said plurality of epitope amino acids occur at every second residue in a β-strand of said β-solenoid structured polypeptide and comprise exposed side chains that project or are configured to project to an exterior position of a β-solenoid domain of the β-solenoid structured polypeptide.

2. The isolated recombinant polypeptide of claim 1, wherein said β-solenoid structured polypeptide comprises one or more β-arcs comprising a plurality of said epitope amino acids from said disease associated polypeptide.

3. The isolated recombinant polypeptide of claim 1, wherein said β-solenoid scaffold polypeptide comprises a β-solenoid sequence from Het-s, Het-2s, pectate lyase 3, Ca2+-dependent beta-helical antifreeze protein, high molecular weight (HMW) adhesin, Poly(beta-D-mannuronate) C5 epimerase 4, or endopolygalacturonase.

4. The isolated recombinant polypeptide of claim 2, wherein said β-solenoid scaffold polypeptide comprises a polypeptide having a sequence as set forth in any one of SEQ ID NOs: 1, 11, 24, 26, 30, and 32.

5. The isolated recombinant polypeptide of claim 1, wherein said disease associated polypeptide is scrapie prion protein (PrP$^{Sc}$), microtubule-associated protein tau, α-synuclein, prion protein (PrP), Aβ, or β-2-microglobulin.

6. The isolated recombinant polypeptide of claim 1, wherein said β-solenoid domain polypeptide is left-handed.

7. The isolated recombinant polypeptide of claim 1, wherein said β-solenoid domain polypeptide is right-handed.

8. The isolated recombinant polypeptide of claim 1, wherein said β-solenoid domain polypeptide comprises a seven-rung, a four-rung or a two-rung β-solenoid domain.

9. The isolated recombinant polypeptide of claim 1, comprising the amino acid sequence set forth in any one of SEQ ID NOs: 3, 19, 20, 21, 22, 25, 27, and 28.

10. A method of treating a subject having or suspected of having or at risk of developing a prion related disease or disorder, a neurodegenerative disease or disorder, or a proteinopathy, comprising administering an immunogenic composition comprising an isolated recombinant polypeptide according to claim 1, a pharmaceutically acceptable excipient, and, optionally, an adjuvant.

11. The method of claim 10, wherein said prion related disease or disorder, or said neurodegenerative disease or disorder, or said proteinopathy, is Alzheimer's disease (AD), Parkinson's disease (PD), Lewy Body Dementia (LBD), Multiple System Atrophy (MSA), Huntington's disease (HD), amyotrophic lateral sclerosis (ALS), Creutzfeldt-Jakob disease (CJD), Ataxia Telangiectasia Friedreich's Ataxia, Multiple Sclerosis (MS), Prion diseases, Spinocerebellar Ataxia (SCA), Spinal Muscular Atrophy (SMA), Traumatic Brain Injury, spongiform encephalopathies (TSE), Creutzfeldt-Jakob disease (CJD), new variant CJD, Kuru, Gerstmann-StrAussler-Scheinker syndrome (GSS), fatal familial insomnia (FFI), dialysis-related amyloidosis (DRA) in humans, scrapie in sheep and goats, spongiform encephalopathy in cattle, or chronic wasting disease(CWD) in cervids.

12. The method of claim 10, wherein said subject is a human or an animal.

13. The method of claim 10, wherein the isolated recombinant polypeptide comprises the amino acid sequence set forth in SEQ ID NO: 34.

14. The method of claim 10, wherein the isolated recombinant polypeptide comprises the amino acid sequence set forth in any one of SEQ ID NOs: 3, 19, 20, 21, 22, 25, 27, and 28.

* * * * *

UNITED STATES PATENT AND TRADEMARK OFFICE
CERTIFICATE OF CORRECTION

| | | |
|---|---|---|
| PATENT NO. | : 12,098,173 B2 | Page 1 of 1 |
| APPLICATION NO. | : 17/057418 | |
| DATED | : September 24, 2024 | |
| INVENTOR(S) | : Holger Wille et al. | |

It is certified that error appears in the above-identified patent and that said Letters Patent is hereby corrected as shown below:

In the Claims

Column 70, Claim 11, Lines 42-44 replace "amyotrophic lateral sclerosis (ALS), Creutzfeldt-Jakob disease (CJD), Ataxia Telangiectasia Friedreich's Ataxia" with --amyotrophic lateral sclerosis (ALS), Creutzfeldt-Jakob disease (CJD), Ataxia Telangiectasia, Friedreich's Ataxia--;
Line 48 replace "Gerstmann-StrAussler-Scheinker" with --Gerstmann-Sträussler-Scheinker--.

Signed and Sealed this
Twenty-first Day of January, 2025

Coke Morgan Stewart
*Acting Director of the United States Patent and Trademark Office*